US012751929B2

(12) United States Patent
Dong et al.

(10) Patent No.: US 12,751,929 B2
(45) Date of Patent: Oct. 6, 2026

(54) ENGINEERED CELLS AND USES THEREOF

(71) Applicant: OHIO STATE INNOVATION FOUNDATION, Columbus, OH (US)

(72) Inventors: Yizhou Dong, Dublin, OH (US); Xucheng Hou, Columbus, OH (US); Xinfu Zhang, Dalian (CN)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 154 days.

(21) Appl. No.: 17/642,320

(22) PCT Filed: Sep. 11, 2020

(86) PCT No.: PCT/US2020/050366

§ 371 (c)(1),
(2) Date: Mar. 11, 2022

(87) PCT Pub. No.: WO2021/050848

PCT Pub. Date: Mar. 18, 2021

(65) Prior Publication Data

US 2023/0000908 A1 Jan. 5, 2023

Related U.S. Application Data

(60) Provisional application No. 62/898,846, filed on Sep. 11, 2019.

(51) Int. Cl.

| | |
|---|---|
| ***A61K 9/51*** | (2006.01) |
| ***A61K 31/7088*** | (2006.01) |
| ***A61K 38/48*** | (2006.01) |
| ***A61K 40/17*** | (2025.01) |
| ***A61K 40/24*** | (2025.01) |
| ***A61K 40/45*** | (2025.01) |
| ***A61P 31/04*** | (2006.01) |
| ***C07K 7/08*** | (2006.01) |
| ***C07K 14/47*** | (2006.01) |
| ***C12N 5/0786*** | (2010.01) |
| ***C12N 9/50*** | (2006.01) |
| ***C12N 9/64*** | (2006.01) |
| ***C12N 15/88*** | (2006.01) |

(52) U.S. Cl.

CPC ............ *A61K 9/5123* (2013.01); *A61K 40/17* (2025.01); *A61K 40/24* (2025.01); *A61K 40/45* (2025.01); *A61P 31/04* (2018.01); *C07K 7/08* (2013.01); *C12N 5/0645* (2013.01); *C12N 9/6472* (2013.01); *C12Y 304/22001* (2013.01); *A61K 2239/31* (2023.05)

(58) Field of Classification Search

CPC ...... A61K 9/5123; A61K 40/17; A61K 40/24; A61K 40/45; A61K 2239/31; A61K 38/4873; A61K 31/7088; A61P 31/04; C07K 7/08; C07K 14/47; C12N 5/0645; C12N 9/6472; C12N 2510/00; C12N 15/88; C12N 9/50; C12Y 304/22001

See application file for complete search history.

(56) References Cited

U.S. PATENT DOCUMENTS

| | | | |
|---|---|---|---|
| 8,754,039 | B2 | 6/2014 | Eckert et al. |
| 9,254,311 | B2 | 2/2016 | Bancel et al. |
| 2015/0064236 | A1 | 3/2015 | Bancel et al. |
| 2016/0024568 | A1 | 1/2016 | May et al. |
| 2016/0304883 | A1 | 10/2016 | Grund et al. |

FOREIGN PATENT DOCUMENTS

| | | |
|---|---|---|
| WO | 2004/030616 A2 | 4/2014 |
| WO | 2019/027999 | 2/2019 |
| WO | 2019/027999 A1 | 2/2019 |

OTHER PUBLICATIONS

Li et al., (2015) An orthogonal array optimization of lipid-like nanoparticles for mRNA delivery in vivo. Nano Letters, 15(2): pp. 8099-8107.*

Tanaka et al., (2018) In vivo introduction of mRNA encapsulated in lipid nanoparticles to brain neuronal cells and astrocytes via intracerbroventricular administration. Mol. Pharamaceutics, 15: pp. 2060-2067 (Year: 2018).*

Chinese National Intellectual Property Administration. Decision of Rejection issued in CN Application No. 202080071146.9. Jun. 1, 2024. 12 pages.

English translation of Office Action for Chinese Application No. 202080071146.9 dated Jul. 28, 2023.

English translation of Search Report for Chinese Application No. 202080071146.9 dated Jul. 28, 2023.

Tateshitad, Naho et al., Development of a lipoplex type mRNA carrier composed of an ionizable lipid with a vitamin E scaffold and the KALA peptide for use as an ex vivo dendritic cell based cancer vaccine, Aug. 3, 2019, J. Control Release, vol. 310, pp. 35-64.

(Continued)

*Primary Examiner* — Kara D Johnson

(74) *Attorney, Agent, or Firm* — Meunier Carlin & Curfman LLC

(57) ABSTRACT

The present disclosure relates to antigen presenting cells and uses thereof for treating sepsis. In some aspects, disclosed herein is an antigen presenting cell, comprising: a lipid-based nanoparticle, comprising: a recombinant polynucleotide, comprising: a first nucleic acid encoding an antimicrobial peptide; a second nucleic acid encoding cathepsin B; and a third nucleic acid encoding a linker; and a vitamin-lipid.

18 Claims, 31 Drawing Sheets

Specification includes a Sequence Listing.

(56) References Cited

OTHER PUBLICATIONS

Wenfang, Xia, et al., Progress in Treatment of Sepsis, Medical Recapitulate, Jun. 30, 2019, vol. 25, No. 1, pp. 2169-2175. [English Abstract].
International Search Report and Written Opinion issued in PCT/US2020/050366, dated Dec. 15, 2020, 16 pages.
Japanese Patent Office. Office Action issued in JP Application No. 2022-515958. Sep. 3, 2024. 7 pages.
Beaucage, S. L., and M. H. Caruthers. "Deoxynucleoside phosphoramidites—a new class of key intermediates for deoxypolynucleotide synthesis." Tetrahedron letters 22.20 (1981): 1859-1862.
Matteucci, Mark Douglas, and M. Ho Caruthers. "Synthesis of deoxyoligonucleotides on a polymer support." Journal of the American Chemical Society 103.11 (1981): 3185-3191.
Altschul, Stephen F., et al. "Gapped BLAST and PSI-BLAST: a new generation of protein database search programs." Nucleic acids research 25.17 (1997): 3389-3402.
Altschul, Stephen F., et al. "Basic local alignment search tool." Journal of molecular biology 215.3 (1990): 403-410.
Henikoff, Steven, and Jorja G. Henikoff. "Amino acid substitution matrices from protein blocks." Proceedings of the National Academy of Sciences 89.22 (1992): 10915-10919.
Karlin, Samuel, and Stephen F. Altschul. "Applications and statistics for multiple high-scoring segments in molecular sequences." Proceedings of the National Academy of Sciences 90.12 (1993): 5873-5877.
Sadahira, Y., & Mori, M. (1999). Role of the macrophage in erythropoiesis. Pathology International, 49(10), 841-848. doi: 10.1046/j.1440-1827.1999.00954.x.
Takeishi, T., Hirano, K., Kobayashi, T., Hasegawa, G., Hatakeyama, K., & Naito, M. (1999). The Role of Kupffer Cells in Liver Regeneration. Archives of Histology and Cytology, 62(5), 413-422. doi:10.1679/aohc.62.413.
Polazzi, E., Gianni, T., & Contestabile, A. (2001). Microglial cells protect cerebellar granule neurons from apoptosis: Evidence for reciprocal signaling. Glia, 36(3), 271-280. doi: 10.1002/glia.1115.
Reinhart, K., Daniels, R., Kissoon, N., Machado, F. R., Schachter, R. D., & Finfer, S. (2017). Recognizing Sepsis as a Global Health Priority—A WHO Resolution. New England Journal of Medicine, 377(5), 414-417. doi: 10.1056/nejmp1707170.
Van der Poll, T. (2001). Immunotherapy of sepsis. The Lancet Infectious Diseases, 1(3), 165-174. doi: 10.1016/s1473-3099(01)00093-7.
Huttunen, R., & Aittoniemi, J. (2011). New concepts in the pathogenesis, diagnosis and treatment of bacteremia and sepsis. Journal of Infection, 63(6), 407-419. doi:10.1016/j.jinf.2011.08.004.
Hotchkiss, Richard S., and Irene E. Karl. "The pathophysiology and treatment of sepsis." New England journal of medicine 348.2 (2003): 138-150.
Otto, G.P., et al. The late phase of sepsis is characterized by an increased microbiological burden and death rate. Critical care 15, R183 (2011).
Hotchkiss, R.S., Monneret, G. & Payen, D. Immunosuppression in sepsis: a novel understanding of the disorder and a new therapeutic approach. The Lancet infectious diseases 13, 260-268 (2013).
Czermak, Boris J., et al. "Protective effects of C5a blockade in sepsis." Nature medicine 5.7 (1999): 788-792.
Ward, Peter A., and Fatemeh Fattahi. "New strategies for treatment of infectious sepsis." Journal of leukocyte biology 106.1 (2019): 187-192.
Huang, X., et al. PD-1 expression by macrophages plays a pathologic role in altering microbial clearance and the innate inflammatory response to sepsis. Proceedings of the National Academy of Sciences of the United States of America 106, 6303-6308 (2009).
Docke, W.D., et al. Monocyte deactivation in septic patients: restoration by IFN-gamma treatment. Nature medicine 3, 678-681 (1997).
Presneill, J.J., Harris, T., Stewart, A.G., Cade, J.F. & Wilson, J.W. A randomized phase II trial of granulocyte-macrophage colony-stimulating factor therapy in severe sepsis with respiratory dysfunction. American journal of respiratory and critical care medicine 166, 138-143 (2002).
Galbraith, N., Walker, S., Galandiuk, S., Gardner, S. & Polk, H.C., Jr. The Significance and Challenges of Monocyte Impairment: For the Ill Patient and the Surgeon. Surgical infections 17, 303-312 (2016).
Cavaillon, J.M., Eisen, D. & Annane, D. Is boosting the immune system in sepsis appropriate? Critical care (London, England) 18, 216 (2014).
Foster, T.J. Immune evasion by staphylococci. Nature reviews. Microbiology 3, 948-958 (2005).
Garzoni, C. & Kelley, W.L. *Staphylococcus aureus:* new evidence for intracellular persistence. Trends in microbiology 17, 59-65 (2009).
Lewis, A.J., Richards, A.C. & Mulvey, M.A. Invasion of Host Cells and Tissues by Uropathogenic Bacteria. Microbiology spectrum 4 (2016).
Pauwels, A.M., Trost, M., Beyaert, R. & Hoffmann, E. Patterns, Receptors, and Signals: Regulation of Phagosome Maturation. Trends in immunology 38, 407-422 (2017).
June, C.H. & Sadelain, M. Chimeric Antigen Receptor Therapy. The New England journal of medicine 379, 64-73 (2018).
Csoka, B., et al. Macrophage P2X4 receptors augment bacterial killing and protect against sepsis. JCI insight 3:11, Jun. 7, 2018; 3(11): e99431.
Saleh, M., et al. Enhanced bacterial clearance and sepsis resistance in caspase-12-deficient mice. Nature 440, 1064-1068 (2006).
Giles, F.J., Redman, R., Yazji, S. & Bellm, L. Iseganan HCl: a novel antimicrobial agent. Expert opinion on investigational drugs 11, 1161-1170 (2002).
Linke, M., Herzog, V. & Brix, K. Trafficking of lysosomal cathepsin B-green fluorescent protein to the surface of thyroid epithelial cells involves the endosomal/lysosomal compartment. Journal of cell science 115, 4877-4889 (2002).
Vasey, P.A., et al. Phase I clinical and pharmacokinetic study of PK1 [N-(2-hydroxypropyl)methacrylamide copolymer doxorubicin]: first member of a new class of chemotherapeutic agents-drug-polymer conjugates. Cancer Research Campaign Phase I/II Committee. Clinical cancer research : an official journal of the American Association for Cancer Research 5, 83-94 (1999).
Mora, J.R., Iwata, M. & von Andrian, U.H. Vitamin effects on the immune system: vitamins A and D take centre stage. Nature reviews. Immunology 8, 685-698 (2008).
Zhang, C., et al. Chemotherapy drugs derived nanoparticles encapsulating mRNA encoding tumor suppressor proteins to treat triple-negative breast cancer. Nano Res. Apr. 2019; 12(4): 855-861.
Li, B., et al. An orthogonal array optimization of lipid-like nanoparticles for mRNA delivery in vivo. Nano letters 15, 8099-8107 (2015).
Su, X., Fricke, J., Kavanagh, D.G. & Irvine, D.J. In vitro and in vivo mRNA delivery using lipid-enveloped pH-responsive polymer nanoparticles. Molecular pharmaceutics 8, 774-787 (2011).
McConnell, R.M., York, J.L., Frizzell, D. & Ezell, C. Inhibition studies of some serine and thiol proteinases by new leupeptin analogs. Journal of medicinal chemistry 36, 1084-1089 (1993).
Zhang, L., et al. High-throughput synergy screening identifies microbial metabolites as combination agents for the treatment of fungal infections. Proceedings of the National Academy of Sciences of the United States of America 104, 4606-4611 (2007).
Ying, W., Cheruku, P.S., Bazer, F.W., Safe, S.H. & Zhou, B. Investigation of macrophage polarization using bone marrow derived macrophages. JoVE (Journal of Visualized Experiments), e50323 (2013).
Frimodt-Møller, N., Knudsen, J. & Espersen, F. The mouse peritonitis/sepsis model. in Handbook of animal models of infection 127-136 (Elsevier, 1999).
McVicker, G., et al. Clonal expansion during Staphylococcus aureus infection dynamics reveals the effect of antibiotic intervention. PLoS pathogens 10, e1003959 (2014).
Crow, D. Could iPSCs Enable "Off-the-Shelf" Cell Therapy? Cell 177, 1667-1669 (2019).

(56) References Cited

OTHER PUBLICATIONS

The Extended European Search Report issued for Application No. 20862238.1, dated Sep. 11, 2023.
Bellm Lisa et al: "Iseganan HCI: a novel antimicrobial agent", Expert Opinion on Investigational Drugs, vol. 11, No. 8, Aug. 24, 2002 (Aug. 24, 2002), pp. 1161-1170, XP093076369.
Yan Li: "Cathepsin B-cleavable doxorubicin prodrugs for targeted cancer therapy (Review)", International Journal of Oncology, Dec. 28, 2012 (Dec. 28, 2012), XP055207310.
Hou Xucheng et al: "Vitamin lipid nanoparticles enable adoptive macrophage transfer for the treatment of multidrugresistant bacterial sepsis", Nature Nanotechnology, Nature Pub. Group, Inc, London, vol. 15, No. 1, Jan. 6, 2020 (Jan. 6, 2020), pp. 41-46, XP036984672.
Drayton Matthew et al: "Towards Robust Delivery of Antimicrobial Peptides to Combat Bacterial Resistance", MOLECULES, vol. 25, No. 13, Jul. 3, 2020 (Jul. 3, 2020), p. 3048, XP093076713.

* cited by examiner $V_D$-LIPID $V_C$-LIPID $V_H$-LIPID $V_{B3}$-LIPID $V_E$-LIPID $V_{B3}$ DERIVATIVE

COMPOUND 1

$V_{B3}$-LIPID

Vc DERIVATIVE

COMPOUND 1

Vc-LIPID

VITAMIN D

COMPOUND 1

$V_D$-LIPID

VITAMIN E

COMPOUND 1

$V_E$-LIPID $V_H$ DERIVATIVE

COMPOUND 1

$V_H$-LIPID

| Name | Factors (molar ratio) | | | Luminescence intensity |
|---|---|---|---|---|
| | $V_c$-Lipid | DOPE | Cholesterol | |
| A-1 | 10 | 20 | 20 | 4162497 |
| A-2 | 10 | 30 | 30 | 5423914 |
| A-3 | 10 | 40 | 40 | 4255354 |
| A-4 | 10 | 50 | 50 | 1990109 |
| A-5 | 20 | 20 | 30 | 4217821 |
| A-6 | 20 | 30 | 20 | 3022416 |
| A-7 | 20 | 40 | 50 | 4443776 |
| A-8 | 20 | 50 | 40 | 4286400 |
| A-9 | 30 | 20 | 40 | 5090698 |
| A-10 | 30 | 30 | 50 | 6031757 |
| A-11 | 30 | 40 | 20 | 2594503 |
| A-12 | 30 | 50 | 30 | 4350574 |
| A-13 | 40 | 20 | 50 | 4243311 |
| A-14 | 40 | 30 | 40 | 3697141 |
| A-15 | 40 | 40 | 30 | 3195640 |
| A-16 | 40 | 50 | 20 | 2122083 |

| Levels | Factors (molar ratio) | | |
|---|---|---|---|
| | $V_c$-Lipid | DOPE | Cholesterol |
| K1* | 3957969 | 4428582 | 2975375 |
| K2* | 3992604 | 4543808 | 4296988 |
| K3* | 4516883 | 3622319 | 4332399 |
| K4* | 3314544 | 3187292 | 4177239 |

$K_n^* = \Sigma RLI_n/4$

FIG. 7E

| Levels | Factors (molar ratio) | | |
|---|---|---|---|
| | $V_C$-Lipid | DOPE | Cholesterol |
| 1 | 10 | 20 | 20 |
| 2 | 20 | 30 | 30 |
| 3 | 30 | 40 | 40 |
| 4 | 40 | 50 | 50 |
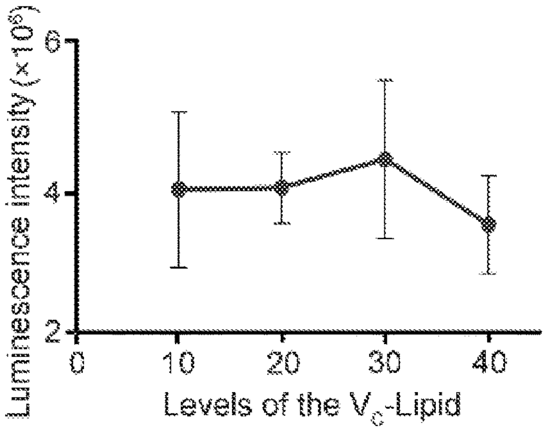
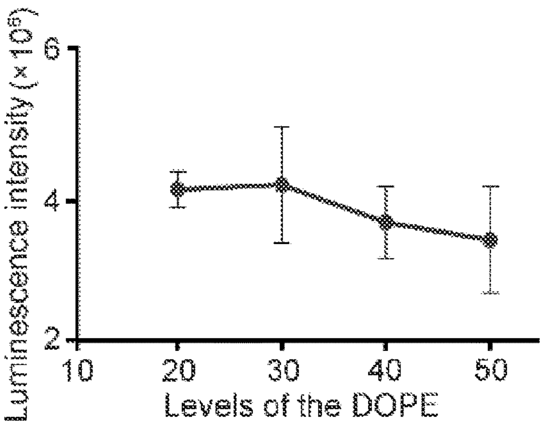
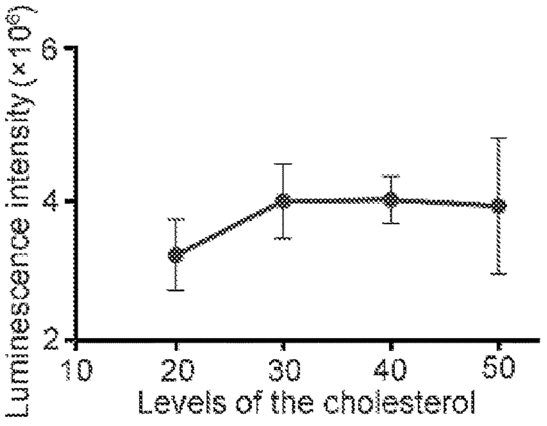
FIG. 8C
| Name | Factors (molar ratio) | | | $V_C$-Lipid/mRNA (wt/wt) |
|---|---|---|---|---|
| | $V_C$-Lipid | DOPE | Cholesterol | |
| B-1 | 30 | 30 | 30 | 10/1 |
| B-2 | 30 | 30 | 40 | 10/1 |
| B-3 | 30 | 30 | 50 | 10/1 |
| B-4 | 30 | 30 | 60 | 10/1 |
| C-1 | 30 | 30 | 50 | 5/1 |
| C-2 | 30 | 30 | 50 | 7.5/1 |
| C-3 | 30 | 30 | 50 | 10/1 |
| C-4 | 30 | 30 | 50 | 12.5/1 |
| C-5 | 30 | 30 | 50 | 15/1 |
| C-6 | 30 | 30 | 50 | 17.5/1 |
| C-7 | 30 | 30 | 50 | 20/1 |
FIG. 8D

ENGINEERED CELLS AND USES THEREOF

CROSS REFERENCE TO RELATED APPLICATIONS

This is a national phase application filed under 35 U.S.C. § 371 of PCT/US2020/050366, filed Sep. 11, 2020, which claims the benefit of U.S. Provisional Patent Application Ser. No. 62/898,846 filed Sep. 11, 2019, which are expressly incorporated herein by reference.

STATEMENT REGARDING FEDERALLY SPONSORED RESEARCH

This invention was made with government support under grant number R35GM119679 awarded by the National Institutes of Health. The government has certain rights in the invention.

REFERENCE TO SEQUENCE LISTING

The Sequence Listing submitted Nov. 6, 2025, as a TXT format entitled "10336-634US1_Sequence_Listing.txt", created on Nov. 6, 2025, and having a size of 10,705 bytes is hereby incorporated by reference pursuant to 37 C.F.R. § 1.52(e)(5).

FIELD

The present disclosure relates to engineered cells and uses thereof.

BACKGROUND

Sepsis was once viewed as an uncontrollable inflammatory response to pathogens. However, researchers have re-evaluated therapeutic approaches for sepsis after failures of over 40 clinical trials of anti-inflammatory agents. Recent clinical data reveal that more than 60% of septic patients survive through the initial inflammatory storm but rapidly progress to a longer immunosuppressive state, which is characterized by paralysis and death of immune cells, leading to the inability to clear invading pathogens, an increased susceptibility to hospital-acquired infections, and a high mortality rate. Therefore, what is needed are novel compositions and methods for engineering cells and methods for treating diseases (for example, sepsis).

SUMMARY

In some aspects, disclosed herein is an antigen presenting cell, comprising:

- a lipid-based nanoparticle, comprising:
  - a recombinant polynucleotide, comprising:
    - a first nucleic acid encoding an antimicrobial peptide;
    - a second nucleic acid encoding cathepsin B; and
    - a third nucleic acid encoding a linker; and
  - a vitamin-lipid.

In some embodiments, the first nucleic acid and the second nucleic acid are linked by third nucleic acid.

In some embodiments, the recombinant polynucleotide is encapsulated by the vitamin-lipid.

In some embodiments, the recombinant polynucleotide comprises an RNA or a DNA.

In some embodiments, the antimicrobial peptide comprises the sequence SEQ ID NO: 1.

In some embodiments, the first nucleic acid comprises the sequence SEQ ID NO: 2.

In some embodiments, the second nucleic acid comprises the sequence SEQ ID NO: 4.

In some embodiments, the linker comprises a cathepsin B sensitive linker. In some embodiments, the third nucleic acid comprises the sequence SEQ ID NO: 6.

In some embodiments, the recombinant polynucleotide comprises the sequence SEQ ID NO: 8.

In some embodiments, the vitamin-lipid comprises a vitamin moiety, and wherein the vitamin moiety comprises vitamin B3, vitamin C, vitamin D, vitamin E, vitamin H, or a derivative thereof. In some embodiments, the vitamin moiety is vitamin C.

In some embodiments, the vitamin-lipid is selected from the group consisting of:

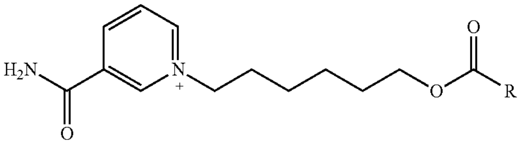

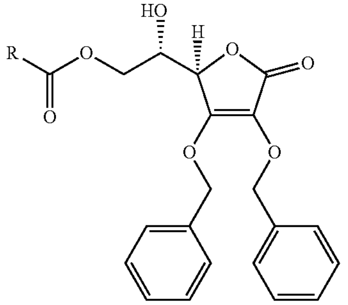

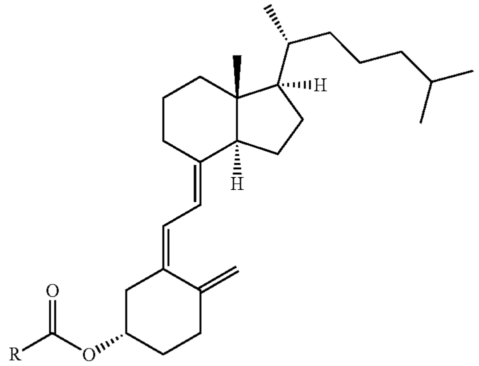

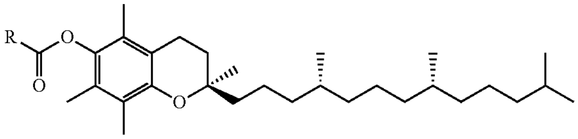

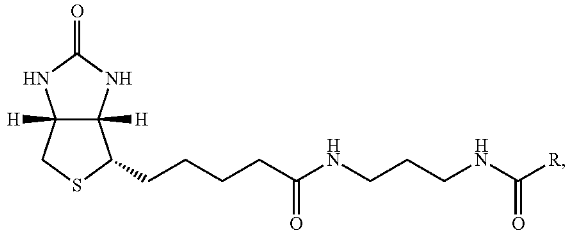

wherein R is

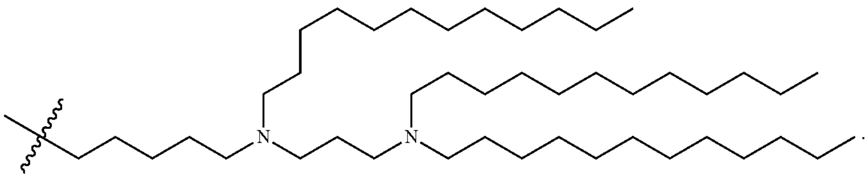 [SMILES: *CCCCCN(CCCCCCCCCCCC)CCCN(CCCCCCCCCCCC)CCCCCCCCCCCC]

In some embodiments, the antigen presenting cell comprises a comprises a macrophage or a dendritic cell. In some embodiments, the macrophage comprises a bone marrow-derived macrophage or a monocyte-derived macrophage. In some embodiments, the dendritic cell comprises a bone marrow-derived dendritic cell, a monocyte-derived dendritic cell, a conventional dendritic cell-1, or a conventional dendritic cell-2.

In some aspects, disclosed herein is a method of treating sepsis, comprising administering to a subject one or more antigen presenting cells comprising:

a nanoparticle, comprising:
- a recombinant polynucleotide, comprising:
  - a first nucleic acid encoding an antimicrobial peptide,
  - a second nucleic acid encoding cathepsin B, and
  - a third nucleic acid encoding a linker; and
- a vitamin-lipid.

In some embodiments, the antigen presenting cell is derived from the subject. In some embodiments, the subject comprises a human. In some embodiments, the human has or is suspected of having sepsis.

BRIEF DESCRIPTION OF THE DRAWINGS

The accompanying figures, which are incorporated in and constitute a part of this specification, illustrate several aspects described below.

FIGS. 7A-7F. Screening and characterization of VLNPs. a) Size, b) PDI, c) encapsulation efficiency, and d) zeta potential of VLNPs. e) Orthogonal array table $L_{16}$ $(4)^4$ and $K_n$* values. f) Cryo-TEM image of the optimal VcLNP formulation (Scale bar=50 nm). Data in a, b, c, and d, are the mean±s.d., triplicate.

FIGS. 8A-8H. Screening and characterization of vitamin-lipid nanoparticles (VLNPs). a) mRNA delivery efficiency of VLNPs in the RAW264.7 cells. b, Expression kinetics of mRNA delivered by VcLNPs in the RAW264.7 cells. c) The first round of characterization: four levels and impact trend of each VcLNP's component. d) Formulation table for the validation of the predicted formulation, and the second round of characterization: the mass ratio of Vc-Lipid: mRNA. E, Fold changes of luminescence intensity in the two rounds of characterization. f) Characterization of the optimal VcLNP formulation, including size distribution, polydispersity index (PDI), encapsulation efficiency, zeta potential, and Cryo-TEM image (Scale bar=100 nm). g) Confocal microscopy of the RAW264.7 cells incubated with VcLNPs encapsulating eGFP-CatB mRNA (Scale bar=10 μm). eGFP-CatB (green) and LysoTracker® Red DND-99 (red) were co-localized in the lysosomes, with a Pearson's correlation coefficient of 0.91±0.15. h) Intracellular survival of MDR *Staphylococcus aureus* (MDRSA) in the RAW264.7 cells exposed to PBS (PBS-RAWs), free AMP-CatB mRNA (Fr-RAWs), empty VcLNPs (Em-RAWs), AMP-CatB mRNA VcLNPs/CatB inhibitor II (In-RAWs), and AMP-CatB mRNA VcLNPs (MAC-RAWs). Data in a, b, e, f, and h are the mean±s.d., n=3 independent experiments. *P<0.05, P<0.01, *P<0.001; ns, not significant (two-tailed Student's t-test).

DETAILED DESCRIPTION

Figure 1A:
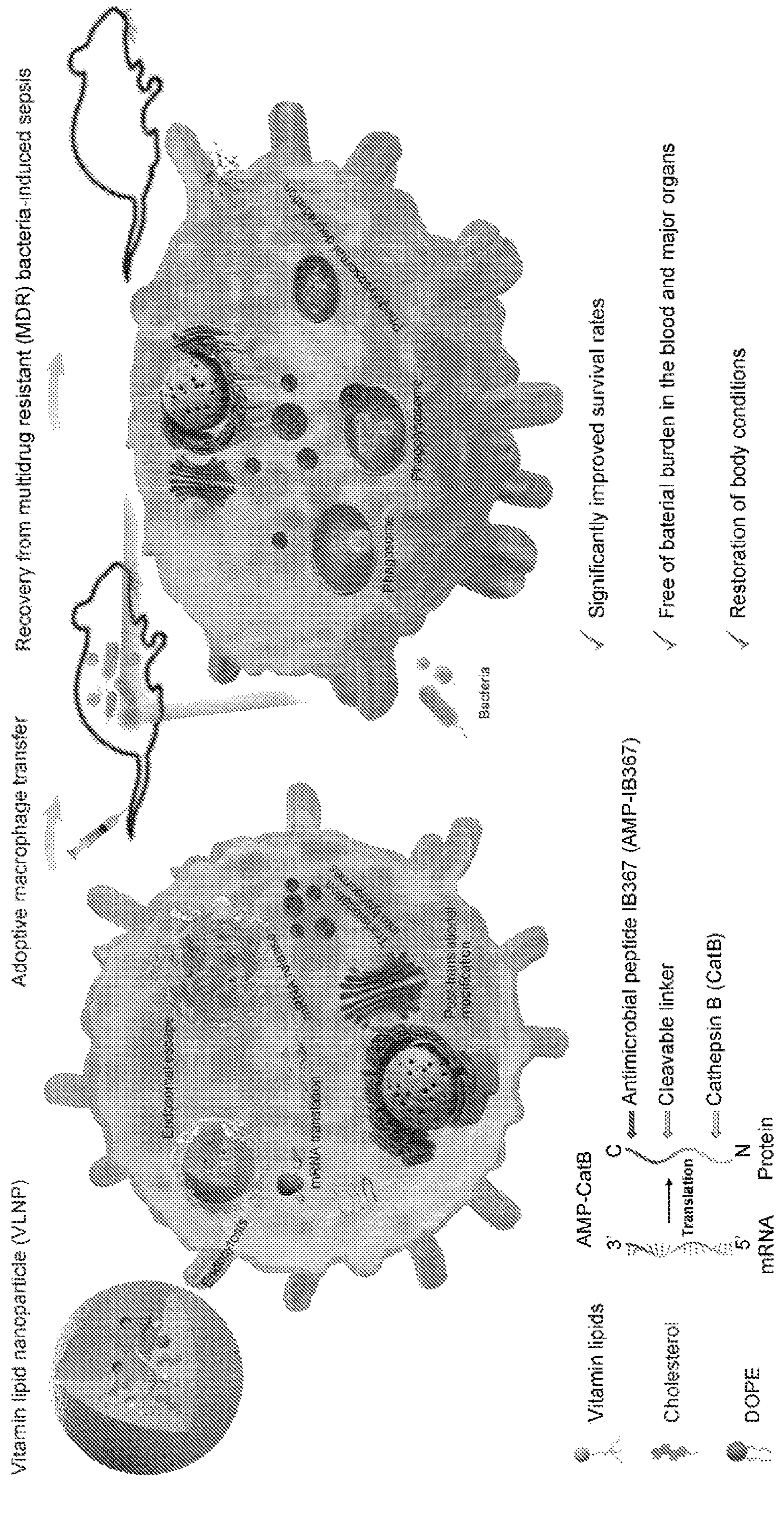
FIG. 1A-1B. Schematic illustration of adoptive macrophage transfer and chemical structures of the vitamin-derived lipids. a) Construction of MACs for sepsis therapy. MACs stands for macrophages loaded with antimicrobial peptides/cathepsin B in the lysosomes. The AMP-CatB mRNA is encapsulated in the vitamin C lipid nanoparticle (VcLNP) and delivered to the macrophage where the mRNA is translated in the endoplasmic reticula and translocated into the lysosomes. Within the lysosomes, the cleavable linker is cleaved by the lysosomal CatB, releasing the AMP-IB367. After phagosomes carrying MDR bacteria fuse with the lysosomes, the ingested MDR bacteria will be eradicated by the pre-stored AMP-IB367. b) Chemical structures of vitamin-derived lipids including VB3-Lipid, Vc-Lipid, VD-Lipid, VE-Lipid, and VH-Lipid.

Sepsis was traditionally, viewed as an uncontrollable inflammatory response to pathogens. However, researchers have re-evaluated therapeutic approaches for sepsis after failures of over 40 clinical trials of anti-inflammatory agents. Clinical data reveal that more than 60% septic patients survive through the initial inflammatory storm but rapidly progress to a longer immunosuppressive state, which is characterized by paralysis and death of immune cells, leading to inability to clear invading pathogens, increased susceptibility to hospital-acquired infections, and high mortality rate. As a result, potential therapeutic targets have been extensively explored in order to treat sepsis such as removing the anaphylatoxin C5a or blocking the C5a receptor. Meanwhile, approaches aiming to restore immune function have been developed and tested in patients with sepsis.

Macrophages are one of the most efficient pathogen scavengers during infections. In patients with sepsis, impaired macrophages/monocytes can be primarily responsible for the insufficient antimicrobial defense. Several small clinical trials of immunostimulatory agents have indicated benefits in reversing deactivated macrophages/monocytes, thereby enhancing infection eradication. In contrast, meta-analysis of large clinical trials did not show significant changes in reducing the patient mortality. Several reasons can lead to these different clinical results. First, the immunostimulatory agents are not able to restore the function of impaired macrophages/monocytes to their original levels. Second, invaded bacteria are usually trapped in macrophage phagosomes which further fuse with lysosomes to form phagolysosomes. Within phagolysosomes, reactive oxygen species (ROS), reactive nitrogen species (RNS), and lysozymes work synergistically to clear bacteria. However, many bacteria, such as *Staphylococcus aureus* and *Escherichia coli* have evolved immune escape mechanisms for thwarting phagolysosomal killing, including scavenging ROS and RNS, and resisting lysozymes, resulting in intracellular survival and recurrent infections. Third, although combined antibiotic therapy is the standard treatment in the sepsis clinical guideline, 70%-80% of sepsis death is related to persistent infections, indicating the prevalence of antibiotic resistance and the paucity of new antimicrobial agents. As an alternative, immunotherapy based on adoptive cell transfer bypasses the need for restoring the dysfunctional immune cells and therefore provides potential benefits in immunocompromised patients.

Disclosed herein is adoptive transfer using macrophages loaded with antimicrobial peptides/cathepsin B in the lysosomes (MACs). To construct the MACs, the antimicrobial peptides/cathepsin B (AMP-CatB) mRNA was designed. Vitamin C lipid nanoparticles (VcLNPs) were identified with more efficient delivery of mRNA than Lipofectamine 3000 and electroporation in both the RAW264.7 cell line and bone marrow derived macrophages (BMDMs). The VcLNPs allow specific accumulation of AMP-CatB in the macrophage lysosomes, the key location for antibacterial activities. It is also disclosed herein that adoptive MAC transfer eliminates MDR bacteria including *Staphylococcus aureus* and *Escherichia coli*, and restores mouse body conditions in the immunocompromised sepsis models, which provides a strategy for overcoming MDR bacteria-induced sepsis and shed light on the development of nanoparticle cell therapy for infectious diseases. Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this disclosure belongs.

Terminology

Terms used throughout this application are to be construed with ordinary and typical meaning to those of ordinary skill in the art. However, Applicant desires that the following terms be given the particular definition as defined below.

As used herein, the article "a," "an," and "the" means "at least one," unless the context in which the article is used clearly indicates otherwise.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

The terms "about" and "approximately" are defined as being "close to" as understood by one of ordinary skill in the art. In one non-limiting embodiment, the terms are defined to be within 10%. In another non-limiting embodiment, the terms are defined to be within 5%. In still another non-limiting embodiment, the terms are defined to be within 1%.

The term "nucleic acid" as used herein means a polymer composed of nucleotides, e.g. deoxyribonucleotides (DNA) or ribonucleotides (RNA).

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" denotes single- or double-stranded nucleotide multimers. Suitable oligonucleotides may be prepared by the phosphoramidite method described by Beaucage and Carruthers, *Tetrahedron Lett.*, 22: 1859-1862 (1981), or by the triester method according to Matteucci, et al., *J. Am. Chem. Soc.*, 103:3185 (1981), both incorporated herein by reference, or by other chemical methods using either a commercial automated oligonucleotide synthesizer or VLSIPS™ technology. When oligonucleotides are referred to as "double-stranded," it is understood by those of skill in the art that a pair of oligonucleotides exist in a hydrogen-bonded, helical array typically associated with, for example, DNA. In addition to the 100% complementary form of double-stranded oligonucleotides, the term "double-stranded," as used herein is also meant to refer to those forms which include such structural features as bulges and loops, described more fully in such biochemistry texts as Stryer, Biochemistry, Third Ed., (1988), incorporated herein by reference for all purposes.

The term "polynucleotide" refers to a single or double stranded polymer composed of nucleotide monomers.

The term "polypeptide" refers to a compound made up of a single chain of D- or L-amino acids or a mixture of D- and L-amino acids joined by peptide bonds.

The term "promoter" or "regulatory element" refers to a region or sequence determinants located upstream or downstream from the start of transcription and which are involved in recognition and binding of RNA polymerase and other proteins to initiate transcription. Promoters need not be of bacterial origin, for example, promoters derived from viruses or from other organisms can be used in the compositions, systems, or methods described herein.

The term "recombinant" refers to a human manipulated nucleic acid (e.g. polynucleotide) or a copy or complement of a human manipulated nucleic acid (e.g. polynucleotide), or if in reference to a protein (i.e, a "recombinant protein"), a protein encoded by a recombinant nucleic acid (e.g. polynucleotide). In some embodiments, a recombinant expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). In another example, a recombinant expression cassette may comprise nucleic acids (e.g. polynucleotides) combined in such a way that the nucleic acids (e.g. polynucleotides) are extremely unlikely to be found in nature. For instance, human manipulated restriction sites or plasmid vector sequences may flank or separate the promoter from the second nucleic acid (e.g. polynucleotide). One of skill will recognize that nucleic acids (e.g. polynucleotides) can be manipulated in many ways and are not limited to the examples above.

The term "expression cassette" or "vector" refers to a nucleic acid construct, which when introduced into a host cell, results in transcription and/or translation of an RNA or polypeptide, respectively. In some embodiments, an expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)).

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) nucleotide sequence identity is defined as the percentage of amino acids in a candidate sequence that are identical to the nucleotides in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

One example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990) *J. Mol. Biol.* 215:403-410). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01.

The phrase "codon optimized" as it refers to genes or coding regions of nucleic acid molecules for the transformation of various hosts, refers to the alteration of codons in the gene or coding regions of polynucleic acid molecules to reflect the typical codon usage of a selected organism without altering the polypeptide encoded by the DNA. Such optimization includes replacing at least one, or more than one, or a significant number, of codons with one or more codons that are more frequently used in the genes of that selected organism.

The term "nucleobase" refers to the part of a nucleotide that bears the Watson/Crick base-pairing functionality. The most common naturally-occurring nucleobases, adenine (A), guanine (G), uracil (U), cytosine (C), and thymine (T) bear the hydrogen-bonding functionality that binds one nucleic acid strand to another in a sequence specific manner.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA or RNA sequences being linked are near each other, and, in the case of a secretory leader, contiguous and in reading phase. However, operably linked nucleic acids (e.g. enhancers and coding sequences, or multiple coding sequences) do not have to be contiguous. Linking is accomplished by ligation at convenient restriction sites. If such sites do not exist, the synthetic oligonucleotide adaptors or linkers are used in accordance with conventional practice. In some embodiments, a promoter is operably linked with a coding sequence when it is capable of affecting (e.g. modulating relative to the absence of the promoter) the expression of a protein from that coding sequence (i.e., the coding sequence is under the transcriptional control of the promoter).

The term "gene" or "gene sequence" refers to the coding sequence or control sequence, or fragments thereof. A gene may include any combination of coding sequence and control sequence, or fragments thereof. Thus, a "gene" as referred to herein may be all or part of a native gene. A polynucleotide sequence as referred to herein may be used interchangeably with the term "gene", or may include any coding sequence, non-coding sequence or control sequence, fragments thereof, and combinations thereof. The term "gene" or "gene sequence" includes, for example, control sequences upstream of the coding sequence (for example, the ribosome binding site).

The term "nanoparticle" as used herein refers to a particle or structure which is biocompatible with and sufficiently resistant to chemical and/or physical destruction by the environment of such use so that a sufficient number of the nanoparticles remain substantially intact after delivery to the site of application or treatment and whose size is in the nanometer range. For the purposes of the present invention, a nanoparticle typically ranges from about 1 nm to about 1000 nm, from about 50 nm and about 500 nm, from about 50 nm and about 350 nm, from about 100 nm and about 250 nm, or from about 110 nm and about 150 nm.

The phrase "symptoms of sepsis" refers to any symptom characteristic of a subject with sepsis including but not limited to, arterial hypotension, metabolic acidosis, fever, decreased systemic vascular resistance, tachypnea and organ dysfunction. Sepsis can result from septicemia (i.e., organisms, their metabolic end-products or toxins in the blood stream), including bacteremia (i.e., bacteria in the blood), as well as toxemia (i.e., toxins in the blood), including endotoxemia (i.e., endotoxin in the blood). The term "sepsis" also encompasses fungemia (i.e., fungi in the blood), viremia (i.e., viruses or virus particles in the blood), and parasitemia (i.e., helminthic or protozoan parasites in the blood). Thus, phenotypes associated with septicemia and septic shock (acute circulatory failure resulting from septicemia often associated with multiple organ failure and a high mortality rate) are symptoms of sepsis.

As used herein, the terms "treating" or "treatment" of a subject includes the administration of a therapeutic agent to a subject with the purpose of curing, healing, alleviating, relieving, altering, remedying, ameliorating, improving, stabilizing or affecting a disease or disorder, or a symptom of a disease or disorder. The terms "treating" and "treatment" can also refer to reduction in severity and/or frequency of symptoms, elimination of symptoms and/or underlying cause, and improvement or remediation of damage.

"Therapeutic agent" refers to any composition that has a beneficial biological effect. Beneficial biological effects include both therapeutic effects, e.g., treatment of a disorder or other undesirable physiological condition, and prophylactic effects, e.g., prevention of a disorder or other undesirable physiological condition (e.g., sepsis). The terms also encompass pharmaceutically acceptable, pharmacologically active derivatives of beneficial agents specifically mentioned herein, including, but not limited to, cells, salts, esters, amides, proagents, active metabolites, isomers, fragments, analogs, and the like. When the terms "therapeutic agent" is used, then, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

"Therapeutically effective amount" or "therapeutically effective dose" of a composition refers to an amount that is effective to achieve a desired therapeutic result. In some embodiments, a desired therapeutic result is the treatment of sepsis. In some embodiments, a desired therapeutic result is restoring immune system in a sepsis patient. In some embodiments, a desired therapeutic result is reduction or clearance of a pathogen. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

"Pharmaceutically acceptable carrier" (sometimes referred to as a "carrier") means a carrier or excipient that is useful in preparing a pharmaceutical or therapeutic composition that is generally safe and non-toxic, and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents.

As used herein, the term "carrier" encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., *Remington's Pharmaceutical Sciences,* 21st Edition, ed. University of the Sciences in Philadelphia, Lippincott, Williams & Wilkins, Philadelphia, PA, 2005. Examples of physiologically acceptable carriers include saline, glycerol, DMSO, buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ (ICI, Inc.; Bridgewater, NJ), polyethylene glycol (PEG), and PLURONICS™ (BASF; Florham Park, NJ). To provide for the administration of such dosages for the desired therapeutic treatment, compositions disclosed herein can advantageously comprise between about 0.1% and 99% by weight of the total of one or more of the subject compounds based on the weight of the total composition including carrier or diluent.

As used throughout, by a "subject" (or a "host") is meant an individual. Thus, the "subject" can include, for example, domesticated animals, such as cats, dogs, etc., livestock (e.g., cattle, horses, pigs, sheep, goats, etc.), laboratory animals (e.g., mouse, rabbit, rat, guinea pig, etc.) mammals, non-human mammals, primates, non-human primates, rodents, birds, reptiles, amphibians, fish, and any other animal. The subject can be a mammal such as a primate or a human.

Antigen Presenting Cells

In some aspects, disclosed herein is an antigen presenting cell, comprising:
- a lipid-based nanoparticle, comprising:
  - a recombinant polynucleotide, comprising:
    - a first nucleic acid encoding an antimicrobial peptide;
    - a second nucleic acid encoding cathepsin B; and
    - a third nucleic acid encoding a linker; and
  - a vitamin-lipid.

In some aspects, disclosed herein is an antigen presenting cell, comprising:
- a lipid-based nanoparticle, comprising:
  - a recombinant polynucleotide, comprising:
    - a first nucleic acid encoding an antimicrobial peptide;
    - a second nucleic acid encoding a cathepsin B peptide; and
    - a third nucleic acid encoding a linker; and
  - a vitamin-lipid.

In some aspects, disclosed herein is an antigen presenting cell, comprising:
- a lipid-based nanoparticle, comprising:
  - a recombinant polynucleotide, comprising:
    - a first nucleic acid encoding an antimicrobial peptide;
    - a second nucleic acid encoding a cathepsin peptide; and
    - a third nucleic acid encoding a linker; and
  - a vitamin-lipid.

In some embodiments, the antigen presenting cell comprises a macrophage or a dendritic cell.

It should be understood that the term "antigen presenting cells" or "APCs" used herein refers to a heterologous group of immune cells that can process and present antigens for stimulating responses of certain lymphocytes (e.g., T cells and B cells). Classical APCs include, for example, dendritic cells, macrophages, B cells, and neutrophils.

It is understood herein that macrophages are commonly known as phagocytosing immune cells (Meszaros et al, 1999). They also secrete factors such as chemokines or cytokines. In addition to phagocytosis and antigen presentation, these cells may play a supportive role through a varied repertoire of plasma membrane and secreted molecules (Gordon 1995, *BioEssays*, Volume17, Issue11), as previously shown for erythroblasts, hepatocytes and neurons (Sadahira & Morr, Pathol Int. 1999 October; 49(10):841-8.) (Takeishi, Hirano, et al. *Arch Histol Cytol.* 1999 December; 62(5):413-22.) (Polazzi, Gianni, et al. *Glia.* 2001 December; 36(3):271-80.). By "macrophages" is meant cells exhibiting properties usually described for macrophages, including phagocytosis, expression of defined cell surface markers such as CD64, CD14 and HLA-DR antigen expression. Macrophages according to the invention can be isolated from tissues or preferentially by ex vivo differentiation from blood monocytes (also referred herein as "monocyte-derived macrophage"), bone marrow precursor cells (also referred herein as "bone marrow-derived macrophage") or from any other possible precursor, and by using any differentiation method, precursors and methods being known by any person skilled in the art. Accordingly, in some embodiments, the macrophage comprises a bone marrow-derived macrophage. In some embodiments, the macrophage comprises a monocyte-derived macrophage. In some embodiments, the macrophage comprises an iPSC-derived macrophage. In some embodiments, the macrophage comprises a macrophage cell line, including, for example, RAW264.7, THP-1, U937, IC-21, J774A.1, MV-4-11, or KGl.

It should be also understood herein that "dendritic cell" or "DC", as used herein, refers to a type of antigen presenting cell, which is typically identified by the expression of one or more of the following markers on its cell surface: CD1a, CD1b, and CD1c, CD4, CD11c, CD33, CD40, CD80, CD86, CD83 and HLA-DR. In some embodiments, the dendritic cell is a mature DC. In some embodiments, the dendritic cell is an immature DC. DCs according to the invention can be isolated from tissues or preferentially by ex vivo differentiation from blood monocytes (also referred herein as "monocyte-derived dendritic cell"), bone marrow precursor cells (also referred herein as "bone marrow-derived dendritic cell") or from any other possible precursor, and by using any differentiation method, precursors and methods being known by any person skilled in the art. Accordingly, in some embodiments, the dendritic cell comprises a bone marrow-derived dendritic cell. In some embodiments, the dendritic cell comprises a monocyte-derived dendritic cell. In some embodiments, the dendritic cell comprises an iPSC-derived dendritic cell. In some embodiments, the dendritic cell is a conventional dendritic cell 1 (or cDC1, lymphoid DC), which is typically identified by the expression of one or more of the following markers on its cell surface: CD141, CLEC9A, and XCR1. In some embodiments, the dendritic cell is a conventional dendritic cell 2 (or cDC2, myeloid DC), which is typically identified by the expression of one or more of the following markers on its cell surface: CD1c and CD172a. In some embodiments, the dendritic cell is plasmacytoid DC (or pDC), which is typically identified by the expression of one or more of the following markers on its cell surface: CD123, CD303, and CD304.

In some embodiments, the antigen presenting cell is derived from a subject selected from the group consisting of a mouse, a rat, a human, or a non-human primate. In some embodiments, the antigen presenting cell is derived from a mouse. In some embodiments, the antigen presenting cell is derived from a rat. In some embodiments, the antigen presenting cell is derived from a human. In some embodiments, the antigen presenting cell is derived from a non-human primate.

Nanoparticles

While a number of nanoparticles are described herein, additional nanoparticles known in the art can also be used herein.

In some aspects, disclosed herein is a lipid-based nanoparticle, comprising:
- a recombinant polynucleotide, comprising:
  - a first nucleic acid encoding an antimicrobial peptide;
  - a second nucleic acid encoding cathepsin B; and
  - a third nucleic acid encoding a linker; and
- a vitamin-lipid.

In some aspects, disclosed herein is a lipid-based nanoparticle, comprising:
- a recombinant polynucleotide, comprising:
  - a first nucleic acid encoding an antimicrobial peptide;
  - a second nucleic acid encoding a cathepsin B peptide; and
  - a third nucleic acid encoding a linker; and
- a vitamin-lipid.

In some aspects, disclosed herein is a lipid-based nanoparticle, comprising:
- a recombinant polynucleotide, comprising:
  - a first nucleic acid encoding an antimicrobial peptide;
  - a second nucleic acid encoding a cathepsin peptide; and
  - a third nucleic acid encoding a linker; and
- a vitamin-lipid.

The term "vitamin-lipid" used herein refers to a compound comprising a vitamin moiety and a lipid, wherein the lipid can be a lipid-like moiety. The term "vitamin-lipid" is also meant to refer to those forms described more fully in WO2019/027999, incorporated herein by reference for all purposes. Accordingly, the vitamin-lipid can be, for example, a compound of Formula A:

Formula A

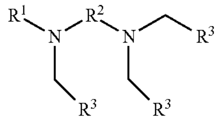

or a salt thereof, wherein:

$R^1$ is an alkyl or ether linker, wherein the alkyl or ether linker is substituted with a vitamin moiety;

$R^2$ is alkyl, cycloalkyl, heterocycloalkyl, alkylheterocycloalkyl, amide, alkylamide, ether, alkylether,

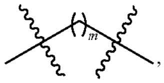, 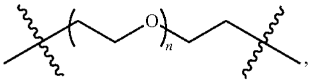, or

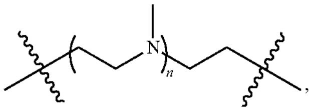, wherein m is an integer from 1 to 20, wherein n is an integer from 1 to 3; and each $R^3$ is independently selected from alkyl, alkenyl, alkynyl, ester, or alkylester.

In one embodiments, the vitamin-lipid can be a compound of Formula I

Formula I

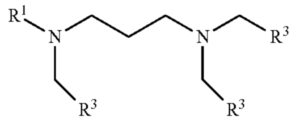

or a salt thereof, wherein:

$R^1$ is an alkyl or ether linker, wherein the alkyl or ether linker is substituted with a carbohydrate moiety, a phosphate moiety, or a vitamin moiety; and each $R^3$ is independently selected from alkyl, alkenyl, alkynyl, ester, or alkylester.

The vitamin moiety can be, for example, vitamin B3, vitamin C, vitamin D, vitamin E, vitamin H, or a derivative thereof. In some embodiments, the vitamin moiety is vitamin C or a derivative thereof. The vitamin moiety is shown below:

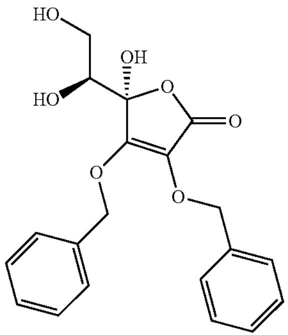
vitamin C derivative
In some embodiments, vitamin-lipid comprises:
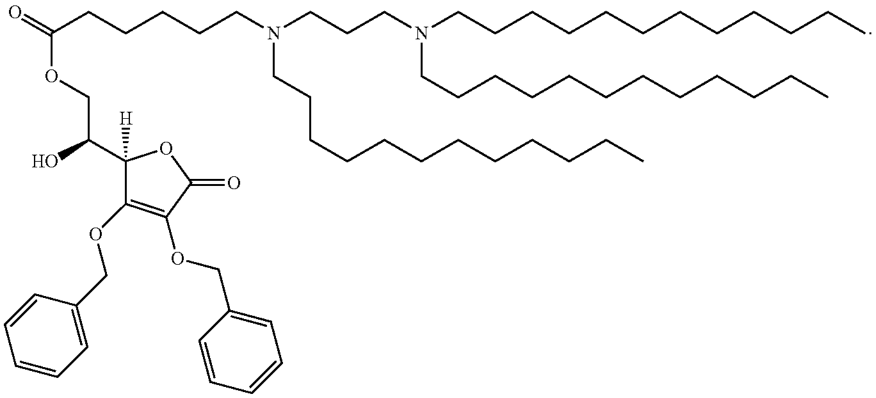
vitamin C-lipid
In some embodiments, the vitamin-lipid is selected from the group consisting of:
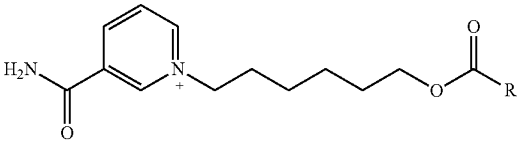
$V_{B3}$-Lipid
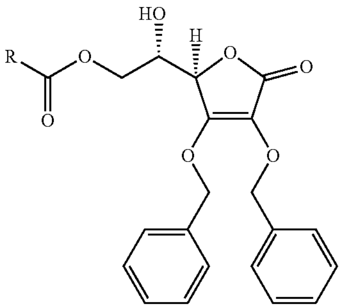
$V_C$-Lipid -continued
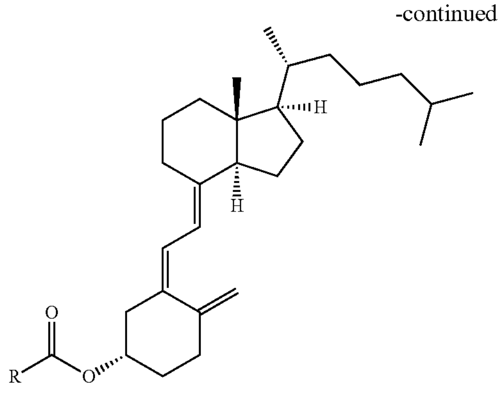
$V_D$-Lipid
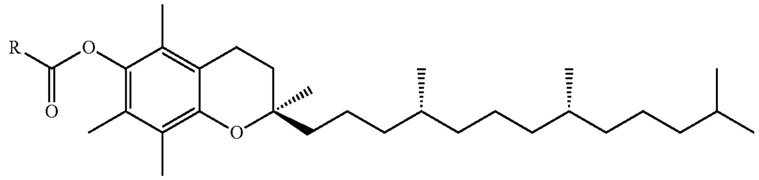
$V_E$-Lipid
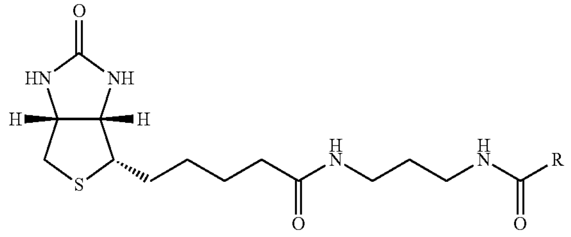
$V_H$-Lipid
R =
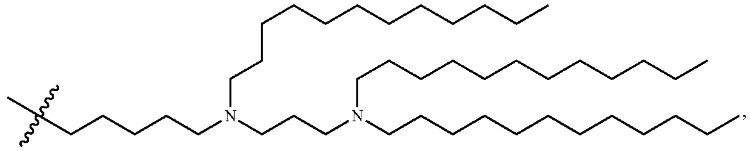
or a salt thereof.
In some embodiments, the vitamin-lipid is selected from the group consisting of
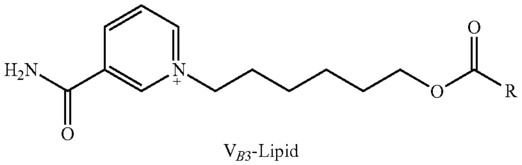
$V_{B3}$-Lipid
-continued
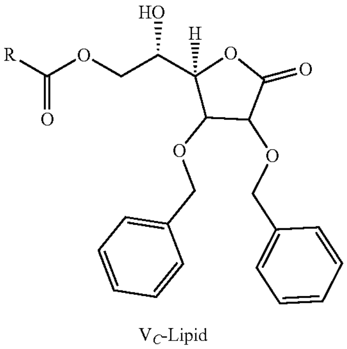
$V_C$-Lipid -continued

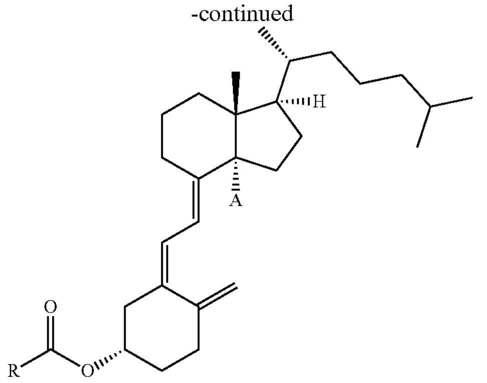

$V_D$-Lipid

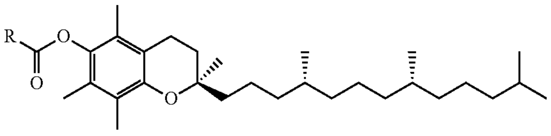

$V_E$-Lipid

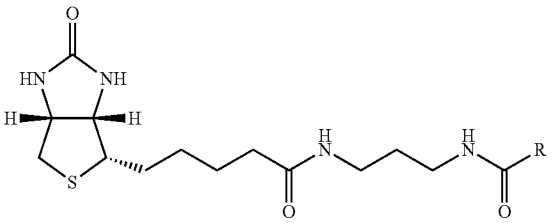

$V_H$-Lipid

R=

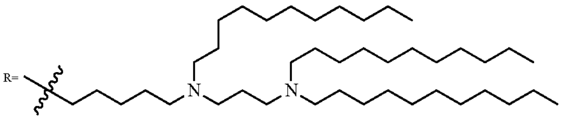

or a salt thereof.

In some embodiments, the lipid-based nanoparticle comprises a vitamin-lipid in a molar ratio of about 10% to about 60%. In some embodiments, the lipid-based nanoparticle comprises a vitamin-lipid in a molar ratio of about 10% to about 40%. In some embodiments, the lipid-based nanoparticle comprises a vitamin-lipid in a molar ratio of about 10%, about 15%, about 20%, about 25%, about 30%, about 35%, about 40%, about 50%, about 60%, about 70%, or about 80%. In one embodiments, the lipid-based nanoparticle comprises a vitamin-lipid in a molar ratio of about 30%.

In some embodiments, the lipid-based nanoparticle further comprises a non-cationic lipid, which can include, but not limited to, 1,2-dioleoyl-sn-glycero-3-phosphoethanolamine (DOPE), 1-palmitoyl-2-oleoyl-sn-glycero-3-phosphoethanolamine (POPE), 1,2-distearoyl-sn-glycero-3-phosphocholine (DSPC), 1-stearoyl-2-oleoyl-sn-glycero-3-phosphoethanolamine (SOPE), DPPC (1,2-dipalmitoyl-sn-glycero-3-phosphocholine), 1,2-dioleyl-sn-glycero-3-phosphotidylcholine (DOPC), 1,2-dipalmitoyl-sn-glycero-3-phosphoethanolamine (DPPE), 1,2-dimyristoyl-sn-glycero-3-phosphoethanolamine (DMPE), 1,2-dioleoyl-5/7-glycero-3-phospho-(1'-rac-glycerol) (DOPG), or combinations thereof.

In some embodiments, the lipid-based nanoparticle further comprises a polyethylene glycol-lipid (PEG-lipid), which can include, but not limited to, PEG-modified phosphatidylethanolamines, PEG-modified phosphatidic acids, PEG-modified ceramides, PEG-modified dialkylamines, PEG-modified diacylglycerols, and PEG-modified dialkylglycerols. Representative polyethylene glycol-lipids include DMG-PEG, DLPE-PEGs, DMPE-PEGs, DPPC-PEGs, and DSPE-PEGs.

In some embodiments, the lipid-based nanoparticle further comprises PEGylated cholesterol, DC-Choi (N,N-dimethyl-N— ethylcarboxamidocholesterol), 1,4-bis(3-N-oleylamino-propyl)piperazine, or combinations thereof.

In some embodiments, the lipid-based nanoparticle further comprises a recombinant polynucleotide, wherein the polynucleotide can be encapsulated by the vitamin-lipid.

Polynucleotides and Polypeptides

In some embodiments, the recombinant polynucleotide comprises an RNA or a DNA. In some embodiments, the recombinant polynucleotide is an RNA. In some embodiments, the recombinant polynucleotide is a mRNA. In some embodiments, the recombinant polynucleotide is a DNA.

The term "antimicrobial peptide" as disclosed herein comprises a peptide or a derivative thereof having antimicrobial activity against one or more selected from a group consisting of bacteria such as Gram-positive bacteria, Gram negative bacteria, etc. and fungi such as yeast, molds, etc. In some embodiments, the antimicrobial peptide comprises the sequence SEQ ID NO: 1, or a fragment or functionally active variant thereof. In some embodiments, the antimicrobial peptide is selected from the group comprising a polypeptide sequence at least 60% (for example, at least 60%, at least 65%, at least 70%, at least 75%, at least 80%, at least 85%, at least 90%, at least 95%, at least 96%, at least 97%, at least 98%, at least 99%) identical to SEQ ID NO: 1. In some embodiments, the antimicrobial peptide is selected from Protegrin 1, C16G2, Omiganan, β-Defensins, hLF1-11, LL37, or MSI-78, or a fragment or functionally active variant thereof. These antimicrobial peptide sequences and additional antimicrobial peptides are known in the art, for example, see U.S. Pat. No. 8,754,039, which is incorporated by reference herein in its entirety.

The antimicrobial peptide of any preceding aspect can be encoded by the first nucleic acid of the recombinant polynucleotide. In some embodiments, the first nucleic acid comprises the sequence SEQ ID NO: 2, or a fragment or functionally active variant thereof. In some embodiments, the first nucleic acid is selected from the group comprising a polynucleotide sequence at least 60% (for example, at least 60%, at least 65%, at least 70%, at least 75%, at least 80%, at least 85%, at least 90%, at least 95%, at least 96%, at least 97%, at least 98%, at least 99%) identical to SEQ ID NO: 2.

Cathepsin B disclosed herein comprises a polypeptide sequence set forth in SEQ ID NO: 3, or a fragment or functionally active variant thereof. In some embodiments, cathepsin B is selected from the group comprising a polypeptide sequence at least 60% (for example, at least 60%, at least 65%, at least 70%, at least 75%, at least 80%, at least 85%, at least 90%, at least 95%, at least 96%, at least 97%, at least 98%, at least 99%) identical to SEQ ID NO: 3.

Cathepsin B of any preceding aspect can be encoded by the second nucleic acid of the recombinant polynucleotide. In some embodiments, the second nucleic acid comprises the sequence SEQ ID NO: 4, or a fragment or functionally active variant thereof. In some embodiments, the second nucleic acid is selected from the group comprising a polynucleotide sequence at least 60% (for example, at least 60%, at least 65%, at least 70%, at least 75%, at least 80%, at least 85%, at least 90%, at least 95%, at least 96%, at least 97%, at least 98%, at least 99%) identical to SEQ ID NO: 4.

In some aspects, disclosed herein is an antigen presenting cell, comprising:

a lipid-based nanoparticle, comprising:
a recombinant polynucleotide, comprising:
a first nucleic acid encoding an antimicrobial peptide;
a second nucleic acid; and
a third nucleic acid encoding a linker; and
a vitamin-lipid.

In some aspects, disclosed herein is an antigen presenting cell, comprising:

a lipid-based nanoparticle, comprising:
a recombinant polynucleotide, comprising:
a first nucleic acid encoding an antimicrobial peptide;
a second nucleic acid encoding a cathepsin peptide; and
a third nucleic acid encoding a linker; and
a vitamin-lipid.

In some embodiments, the second nucleic acid encoding a cathepsin peptide comprises Cathepsin A, Cathepsin B, Cathepsin C, Cathepsin D, Cathepsin E, Cathepsin F, or Cathepsin G, or a fragment or functionally active variant thereof. These sequences are known in the art and can be found at the National Center for Biotechnology Information website (www.ncbi.nlm.nih.gov). In some embodiments, the sequences are from a mammal. In some embodiments, the sequences are from a mouse. In some embodiments, the sequences are from a primate. In some embodiments, the sequences are from a human.

In some embodiments, the linker comprises a cathepsin B sensitive linker. In some embodiments, the linker comprises a polypeptide sequence set forth in SEQ ID NO: 5, or a fragment or functionally active variant thereof. In some embodiments, the linker is selected from the group comprising a polypeptide sequence at least 60% (for example, at least 60%, at least 65%, at least 70%, at least 75%, at least 80%, at least 85%, at least 90%, at least 95%, at least 96%, at least 97%, at least 98%, at least 99%) identical to SEQ ID NO: 5.

The linker of any preceding aspect can be encoded by the third nucleic acid. In some embodiments, the third nucleic acid comprises the sequence SEQ ID NO: 6, or a fragment or functionally active variant thereof. In some embodiments, the third nucleic acid is selected from the group comprising a polynucleotide sequence at least 60% (for example, at least 60%, at least 65%, at least 70%, at least 75%, at least 80%, at least 85%, at least 90%, at least 95%, at least 96%, at least 97%, at least 98%, at least 99%) identical to SEQ ID NO: 6.

In some embodiments, the linker comprises a polypeptide sequence set forth in SEQ ID NO: 9, SEQ ID NO: 10, SEQ ID NO: 11, or SEQ ID NO: 12, or a fragment or functionally active variant thereof. In some embodiments, the linker is selected from the group comprising a polypeptide sequence at least 60% (for example, at least 60%, at least 65%, at least 70%, at least 75%, at least 80%, at least 85%, at least 90%, at least 95%, at least 96%, at least 97%, at least 98%, at least 99%) identical to SEQ ID NO: 9, SEQ ID NO: 10, SEQ ID NO: 11, or SEQ ID NO: 12. In some embodiments, the linker may also be Phe-Lys.

In some embodiments, the recombinant polynucleotide of any preceding aspect comprises the sequence SEQ ID NO: 7, or a fragment or functionally active variant thereof. In some embodiments, the recombinant polynucleotide is selected from the group comprising a polynucleotide sequence at least 60% (for example, at least 60%, at least 65%, at least 70%, at least 75%, at least 80%, at least 85%, at least 90%, at least 95%, at least 96%, at least 97%, at least 98%, at least 99%) identical to SEQ ID NO: 7.

In some embodiments, the recombinant polynucleotide encodes a recombinant polypeptide comprising a sequence set forth in SEQ ID NO: 8, or a fragment or functionally active variant thereof. In some embodiments, the recombinant polypeptide is selected from the group comprising a polynucleotide sequence at least 60% (for example, at least 60%, at least 65%, at least 70%, at least 75%, at least 80%, at least 85%, at least 90%, at least 95%, at least 96%, at least 97%, at least 98%, at least 99%) identical to SEQ ID NO: 8.

In some embodiments, the first nucleic acid and the second nucleic acid are linked by the third nucleic acid.

Methods of Treatment

In some aspects, disclosed herein is a method of treating sepsis, comprising administering to a subject one or more antigen presenting cells comprising:

a nanoparticle, comprising:
a recombinant polynucleotide, comprising:
a first nucleic acid encoding an antimicrobial peptide,
a second nucleic acid encoding cathepsin B, and
a third nucleic acid encoding a linker; and
a vitamin-lipid.

In some aspects, disclosed herein is a method of treating sepsis, comprising administering to a subject one or more antigen presenting cells comprising:

a nanoparticle, comprising:
a recombinant polynucleotide, comprising:
a first nucleic acid encoding an antimicrobial peptide,
a second nucleic acid, and
a third nucleic acid encoding a linker; and
a vitamin-lipid.

In some aspects, disclosed herein is a method of treating sepsis, comprising administering to a subject one or more antigen presenting cells comprising:

a nanoparticle, comprising:
a recombinant polynucleotide, comprising:
a first nucleic acid encoding an antimicrobial peptide,
a second nucleic acid encoding a cathepsin peptide, and
a third nucleic acid encoding a linker; and
a vitamin-lipid.

In some aspects, disclosed herein is a method of treating sepsis, comprising administering to a subject one or more antigen presenting cells comprising:

a nanoparticle, comprising:
a recombinant polynucleotide, comprising:
a first nucleic acid encoding an antimicrobial peptide,
a second nucleic acid encoding a cathepsin B peptide, and
a third nucleic acid encoding a linker; and
a vitamin-lipid.

As disclosed above, the term "sepsis" also encompasses bacteremia (i.e., bacteria in the blood), toxemia (i.e., toxins in the blood), fungemia (i.e., fungi in the blood), viremia (i.e., viruses or virus particles in the blood), and parasitemia (i.e., helminthic or protozoan parasites in the blood). Thus, phenotypes associated with septicemia and septic shock (acute circulatory failure resulting from septicemia often associated with multiple organ failure and a high mortality rate) are symptoms of sepsis. Accordingly, disclosed herein is a method of treating, inhibiting, or reducing sepsis or the symptoms of sepsis (for example, reducing load of bacteria, toxin, fungi, virus or parasites in the blood, and/or restoring, maintaining or improving immune system of the affected subject.

In some embodiments, the antigen presenting cell of any preceding aspects is derived from the subject. In some embodiments, the antigen presenting cell is derived from the subject. In some embodiments, the antigen presenting cell is derived from a different subject. In some embodiments, the subject is a human. In some embodiments, the human has or is suspected of having sepsis.

In some embodiments, the method of treating sepsis comprises administering to a subject one or more antigen presenting cells of any preceding aspect, wherein the one or more antigen presenting cells are prepared and administered together with a pharmaceutically acceptable carrier.

As the timing of sepsis can often not be predicted, it should be understood the disclosed methods of treating, preventing, reducing, and/or inhibiting sepsis, can be used prior to or following the onset of septic symptoms, to treat, prevent, inhibit, and/or reduce sepsis. Where, the disclosed methods can be performed any time prior to sepsis. In one aspect, the disclosed methods can be employed 12, 11, 10, 9, 8, 7, 6, 5, 4, 3, 2, 1 months, 30, 29, 28, 27, 26, 25, 24, 23, 22, 21, 20, 19, 18, 17, 16, 15, 14, 13, 12, 11, 10, 9, 8, 7, 6, 5, 4, 3 days, 60, 48, 36, 30, 24, 18, 15, 12, 10, 9, 8, 7, 6, 5, 4, 3, 2 hours, 60, 45, 30, 15, 10, 9, 8, 7, 6, 5, 4, 3, 2, or 1 minute prior to sepsis; or 1, 2, 3, 4, 5, 6, 7, 8, 9, 10, 15, 20, 25, 30, 35, 40, 45, 50, 55, 60, 75, 90, 105, 120 minutes, 3, 4, 5, 6, 7, 8, 9, 10, 11, 12, 15, 18, 24, 30, 36, 48.60 hours, 3, 4, 5, 6, 7, 8, 9, 10, 11, 12, 13, 14, 15, 16, 17, 18, 19, 20, 21, 22, 23, 24, 25, 26, 27, 28, 29, 30, 45, 60, 90 or more days, 4, 5, 6, 7, 8, 9, 10, 11, 12 or more months, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1 years after sepsis.

The antigen presenting cells of the present invention can be administered to the appropriate subject in any manner known in the art, e.g., orally intramuscularly, intravenously, sublingual mucosal, intraarterially, intrathecally, intradermally, intraperitoneally, intranasally, intrapulmonarily, intraocularly, intravaginally, intrarectally or subcutaneously. They can be introduced into the gastrointestinal tract or the respiratory tract. Parenteral administration, if used, is generally characterized by injection.

In some aspects, disclosed herein is a method of treating a disease, comprising administering to a subject one or more antigen presenting cells comprising:
- a nanoparticle, comprising:
  - a recombinant polynucleotide, comprising:
    - a first nucleic acid encoding an antimicrobial peptide,
    - a second nucleic acid (for example, encoding a cathepsin peptide, such as
    - a cathepsin B peptide), and
    - a third nucleic acid encoding a linker; and
  - a vitamin-lipid.

In some aspects, disclosed herein is a method of treating cancer, comprising administering to a subject one or more antigen presenting cells comprising:
- a nanoparticle, comprising:
  - a recombinant polynucleotide, comprising:
    - a first nucleic acid encoding an antimicrobial peptide,
    - a second nucleic acid (for example, encoding a cathepsin peptide, such as
    - a cathepsin B peptide), and
    - a third nucleic acid encoding a linker; and
  - a vitamin-lipid.

In some embodiments, the disease is selected from lysosomal storage disorder, aspartylglucosaminuria, Gaucher disease, GM1 gangliosidosis, or mucopolysaccharidoses.

In some aspects, disclosed herein is a method of treating a neurodegenerative disease, comprising administering to a subject one or more antigen presenting cells comprising:
- a nanoparticle, comprising:
  - a recombinant polynucleotide, comprising:
    - a first nucleic acid encoding an antimicrobial peptide,
    - a second nucleic acid (for example, encoding a cathepsin peptide, such as
    - a cathepsin B peptide), and
    - a third nucleic acid encoding a linker; and
  - a vitamin-lipid.

In some embodiments, the neurodegenerative disease is selected from Alzheimer's disease, Parkinson's disease, or Huntington disease.

In still other embodiments, disclosed herein is a method of treating a disease, comprising administering to a subject a therapeutically effective amount of the immune cells of any preceding aspect. In some embodiments, the disease is selected from lysosomal storage disorder, aspartylglucosaminuria, Gaucher disease, GM1 gangliosidosis, or mucopolysaccharidoses.

Additional Compositions and Methods

In some aspects, disclosed herein is an immune cell, comprising:
- a lipid-based nanoparticle, comprising:
  - a recombinant polynucleotide encoding an immune protein; and
  - a vitamin-lipid;
- wherein the immune cell comprises a T cell.

In some embodiments, the recombinant polynucleotide is encapsulated by the vitamin-lipid.

In some embodiments, the recombinant polynucleotide comprises an RNA or a DNA. In some embodiments, the recombinant polynucleotide is an RNA. In some embodiments, the recombinant polynucleotide is a mRNA. In some embodiments, the recombinant polynucleotide is a DNA.

In some embodiments, the immune protein comprises a chimeric antigen receptor or a cytotoxic cytokine.

In some embodiments, the immune protein is a chimeric antigen receptor. In some embodiments, the comprises an antigen binding domain, a transmembrane domain, a costimulatory signaling region, or a CD3 zeta signaling domain.

In some embodiments, the antigen binding domain binds to a tumor antigen.

In some embodiments, the immune protein is a cytotoxic cytokine, including, for example, interferon gamma, Tumor Necrosis Factor, granzyme A, granzyme B, or perforin.

In some embodiments, disclosed herein is a method of treating a cancer, comprising administering to a subject a therapeutically effective amount of the immune cells of any preceding aspect.

In still other embodiments, disclosed herein is a method of treating a disease, comprising administering to a subject a therapeutically effective amount of the immune cells of any preceding aspect. In some embodiments, the disease is selected from lysosomal storage disorder, aspartylglucosaminuria, Gaucher disease, GM1 gangliosidosis, or mucopolysaccharidoses.

In some embodiments, disclosed herein is a method of treating a neurodegenerative disease, comprising administering to a subject a therapeutically effective amount of the immune cells of any preceding aspect. In some embodiments, the neurodegenerative disease is selected from Alzheimer's disease, Parkinson's disease, or Huntington disease.

In some embodiments, the subject comprises a human. In some embodiments, the human has or is suspected of having a cancer.

EXAMPLES

The following examples are set forth below to illustrate the compounds, systems, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. Vitamin Lipid Nanoparticles Provide Adoptive Macrophage Transfer to Treat Multidrug Resistant Bacterial Sepsis The data disclosed herein show that adoptive transfer of macrophages loaded with antimicrobial peptides/cathepsin B in the lysosomes (MACs) provides the immunocompromised sepsis host to boost innate immunity, prevent bacterial immune evasion, and eliminate multidrug resistant (MDR) bacteria. As illustrated in FIG. 1*a*, an mRNA (AMP-CatB) was designed and constructed with multiple components, encoding an antimicrobial peptide IB367 (AMP-IB367), a cathepsin B (CatB), and a cleavable linker. AMP-IB367 is a broad-spectrum AMP with rapid bactericidal activity and has been confirmed in clinical trials. CatB, an endogenous protein, is first translated as an inactive precursor in the cytoplasm and translocated into the lysosome. These precursors are then processed into mature Cat B. The function of the CatB component is incorporated to transport the AMP-IB367 into the lysosomes, which are fused with the bacteria-containing phagosomes. The free AMP-IB367 need to be released from the AMP-CatB protein in order to eradicate the bacteria. Therefore, a CatB sensitive linker was added in the mRNA sequence. Lysosomes have a large amount of CatB proteins, facilitating the release of AMP-IB367. In order to equip macrophages with the designed mRNAs, an efficient mRNA delivery system is needed for macrophages, one of the hardest-to-transfect cells. Macrophages uptake different vitamins to achieve their biological functions.

Through the initial screening and two rounds of characterization, the formulation of vitamin C lipid nanoparticles (VcLNPs) allowed AMP-CatB mRNA to be effectively delivered into macrophages. The mRNA is translated to functional proteins in the cytoplasm and the proteins are further translocated into lysosomes. In the lysosomes, the CatB sensitive linker is cleaved by CatB proteins and thus the APM-IB367 is released. When phagosomes encapsulating bacteria fuse with lysosomes, the ingested bacteria are exposed to both pre-stored AMP-IB367 and lysosomal antimicrobial components. Although immune evasion strategies may protect MDR bacteria from phagolysosomal killing mechanisms, the AMP-IB367 is able to kill these bacteria because of its high antibacterial activity against MDR bacteria in animal models and in humans. Consequently, the adoptive transfer of MACs rescues MDR bacteria induced sepsis with immunosuppression by restoring the innate immunity, overcoming bacterial immune evasion, and eradicating the infection.

Figure 1B:
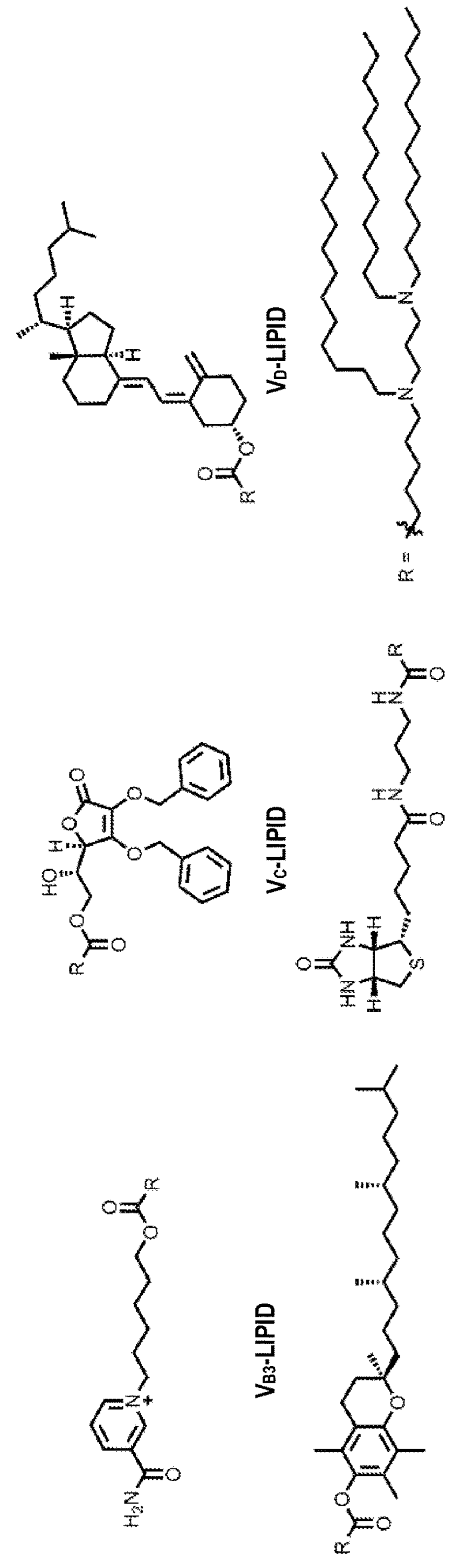
Figure 2:
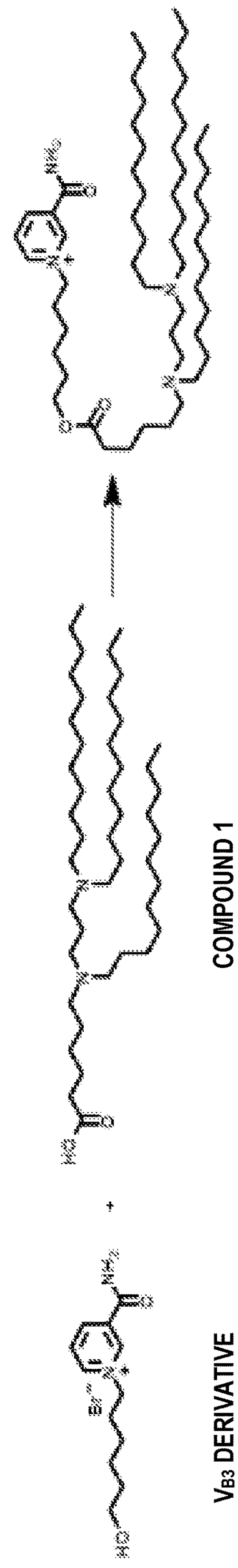
FIG. 2. Synthesis of VB3-Lipid: Compound 1 (150 mg, 0.23 mmole) was dissolved in a mixture of 2 mL $CH_2Cl_2$ and 2 mL DMF. Vitamin B3 derivative (62 mg, 0.21 mmole), EDC (87 mg, 0.46 mmole) and DMPA (10 mg) were added to the solution. The resulting mixture was stirred at room temperature overnight. The reacting mixture was purified by column chromatography using a CombiFlash Rf system with a RediSep Gold Resolution silica column (Teledyne Isco) with gradient elution ($CH_2Cl_2$ and ultra) from 100% $CH_2Cl_2$ to 0% $CH_2Cl_2$ (ultra: $CH_2Cl_2$/MeOH/$NH_4OH$=75/22/3 by volume) to give 80 mg colorless oil VB3-Lipid, yield 37%. $^1H$ NMR (400 MHz, $CDCl_3$): δ=10.75 (1H, s), 9.92 (1H, s), 9.17-9.16 (1H, d, J=4), 8.94 (1H, s), 8.09-8.06 (1H, t, J=4), 6.20 (1H, s), 4.88-4.85 (2H, t, J=4), 4.06-4.03 (2H, t, J=4), 2.47 (11H, m), 2.31-2.28 (2H, t, J=4), 2.13 (2H, s), 1.64-1.63 (7H, m), 1.45 (12H, m), 1.26 (56H, s), 0.89-0.87 (9H, t, J=4). MS (m/z): $M^+$ calcd. for $C_{57}H_{109}N_4O_3$, 897.8494; found: 897.8496.
Figure 3:
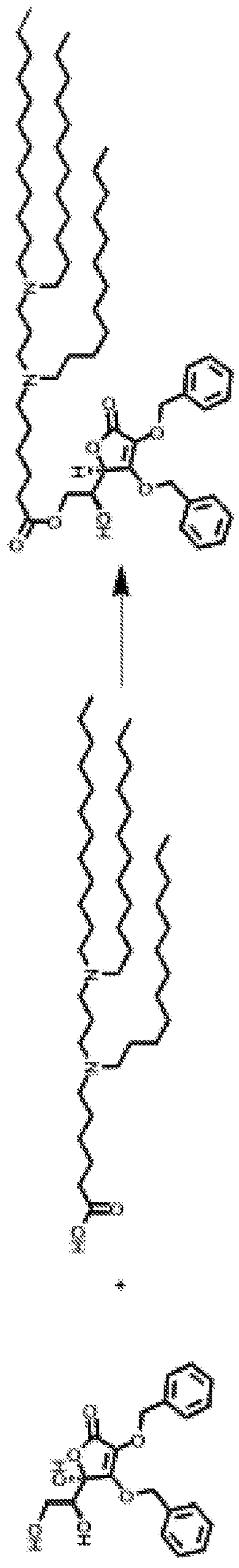
FIG. 3. Synthesis of Vc-Lipid: Compound 1 (150 mg, 0.23 mmole) was dissolved in 2 mL $CH_2Cl_2$. Vitamin C derivative (77 mg, 0.23 mmole), EDC (87 mg, 0.46 mmole) and DMPA (10 mg) were added to the solution. The resulting mixture was stirred at room temperature overnight. The reacting mixture was purified by column chromatography using a CombiFlash Rf system with a RediSep Gold Resolution silica column (Teledyne Isco) with gradient elution ($CH_2Cl_2$ and ultra) from 100% $CH_2Cl_2$ to 80% $CH_2Cl_2$ (ultra: $CH_2Cl_2$/MeOH/$NH_4OH$=75/22/3 by volume) to give 105 mg colorless oil Vc-Lipid, yield 44%. $^1H$ NMR (400 MHz, $CDCl_3$): δ=7.40-7.25 (10H, m), 5.26-5.13 (4H, m), 4.67 (1H, s), 4.33-4.08 (3H, m), 2.65 (1H, s), 2.42 (12H, m), 1.67-1.60 (13H, m), 1.28 (57H, s), 0.92-0.89 (9H, t, J=4). MS (m/z): $[M+H]^+$ calcd. $C_{65}H_{111}N_2O_7$, 1031.8391; found: 1031.8379.
Figure 4:
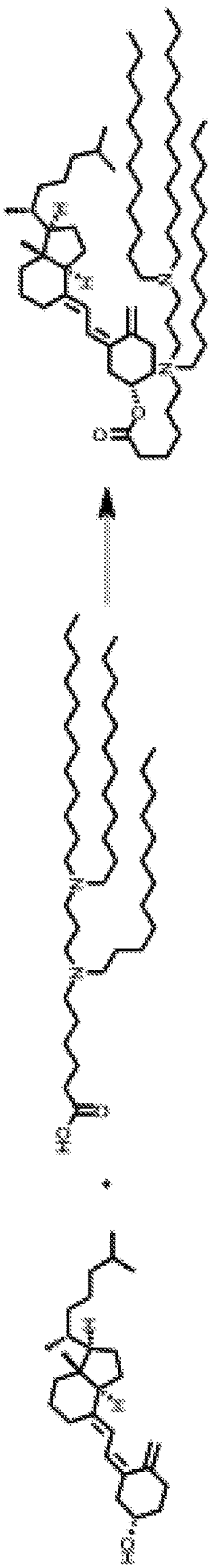
FIG. 4. Synthesis of VD-Lipid: Compound 1 (150 mg, 0.23 mmole) was dissolved in 2 mL $CH_2Cl_2$. Vitamin D (83 mg, 0.23 mmole), EDC (87 mg, 0.46 mmole) and DMPA (10 mg) were added to the solution. The resulting mixture was stirred at room temperature overnight. The reacting mixture was purified by column chromatography using a CombiFlash Rf system with a RediSep Gold Resolution silica column (Teledyne Isco) with gradient elution ($CH_2Cl_2$ and ultra) from 100% $CH_2Cl_2$ to 85% $CH_2Cl_2$ (ultra: $CH_2Cl_2$/MeOH/$NH_4OH$=75/22/3 by volume) to give 40 mg colorless oil VD-Lipid, yield 16%. $^1H$ NMR (400 MHz, $CDCl_3$): δ=6.22-6.19 (1H, d, J=12), 6.04-6.02 (1H, d, J=8), 5.06 (1H, s), 4.94 (1H, s), 4.84 (1H, s), 2.82-2.56 (12H, m), 2.38-2.28 (4H, m), 1.99-1.96 (5H, m), 1.67-1.49 (15H, m), 1.30-1.26 (71H, m), 0.93-0.87 (21H, m), 0.54 (2H, s). MS (m/z): $[M+H]^+$ calcd. for $C_{72}H_{135}N_2O_2$, 1060.0524; found: 1060.0529.
Figure 5:
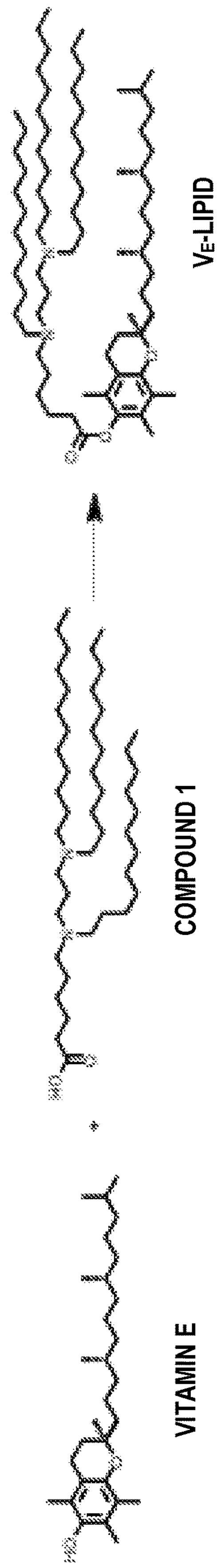
FIG. 5. Synthesis of VE-Lipid: Compound 1 (150 mg, 0.23 mmole) was dissolved in 2 mL $CH_2Cl_2$. Vitamin E (99 mg, 0.23 mmole), EDC (87 mg, 0.46 mmole) and DMPA (10 mg) were added to the solution. The resulting mixture was stirred at room temperature overnight. The reacting mixture was purified by column chromatography using a CombiFlash Rf system with a RediSep Gold Resolution silica column (Teledyne Isco) with gradient elution ($CH_2Cl_2$ and ultra) from 100% $CH_2Cl_2$ to 85% $CH_2Cl_2$ (ultra: $CH_2Cl_2$/MeOH/$NH_4OH$=75/22/3 by volume) to give 66 mg colorless oil VE-Lipid, yield 26%. $^1H$ NMR (400 MHz, $CDCl_3$): δ=2.83-2.57 (14H, m), 2.08 (3H, s), 2.00 (3H, s), 1.96 (3H, s), 1.81 (4H, m), 1.62 (5H, m), 1.54-1.52 (11H, m), 1.28-1.23 (67H, m), 1.14 (7H, m), 0.89-0.84 (24H, m). MS (m/z): $[M+H]^+$ calcd. for $C_{74}H_{141}N_2O_3$, 1106.0942; found: 1106.0944.
Figure 6:
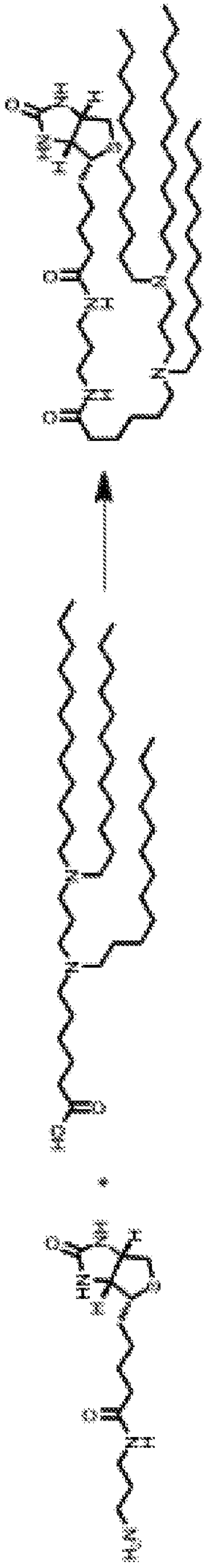
FIG. 6. Synthesis of VH-Lipid: Compound 1 (100 mg, 0.15 mmole) was dissolved in a mixture of 3 mL THF. NHS (50 mg, 0.43 mmole) and DCC (80 mg, 0.39 mmole) were added to the solution that was stirred overnight. Vitamin H derivative (140 mg, 0.46 mmole) and 200 μL trimethylamine was added to the solution. The resulting mixture was stirred at room temperature overnight. The reacting mixture was purified by column chromatography using a CombiFlash Rf system with a RediSep Gold Resolution silica column (Teledyne Isco) with gradient elution ($CH_2Cl_2$ and ultra) from 100% $CH_2Cl_2$ to 75% $CH_2Cl_2$ (ultra: $CH_2Cl_2$/MeOH/$NH_4OH$=75/22/3 by volume) to give 60 mg colorless oil VH-Lipid, yield 41%. $^1H$ NMR (400 MHz, $CDCl_3$): δ=7.11 (1H, s), 6.70 (1H, s), 5.98 (1H, s), 4.52-4.49 (1H, t, J=4), 4.33-4.30 (1H, t, J=4), 3.27-3.28 (4H, m), 2.75-2.60 (11H, m), 2.25-2.19 (4H, m), 1.74-1.64 (11H, m), 1.51-1.49 (11H, m), 1.28 (59H, s), 0.90-0.87 (9H, t, J=4). MS (m/z): $[M+H]^+$ calcd. for $C_{58}H_{115}N_6O_3S$, 975.8751; found: 975.8629.

Five vitamins were first selected: vitamin B3, vitamin C, vitamin D, vitamin E, and vitamin H (also called vitamin B7), and then incorporated lipid tails using the methods reported previously. The amino lipids were installed on these vitamins through an ester bond or amide bond (FIG. 1*b*). These five vitamin-derived lipids were named as VB3-Lipid, Vc-Lipid, VD-Lipid, VE-Lipid, and VH-Lipid. The tertiary amines in the lipid chain can be ionized at an acidic condition and interact with mRNAs. The structures of these vitamin-derived lipids were confirmed by $^1$H NMR and mass spectrum (MS) (FIGS. 2 to 6).

Figure 7A:
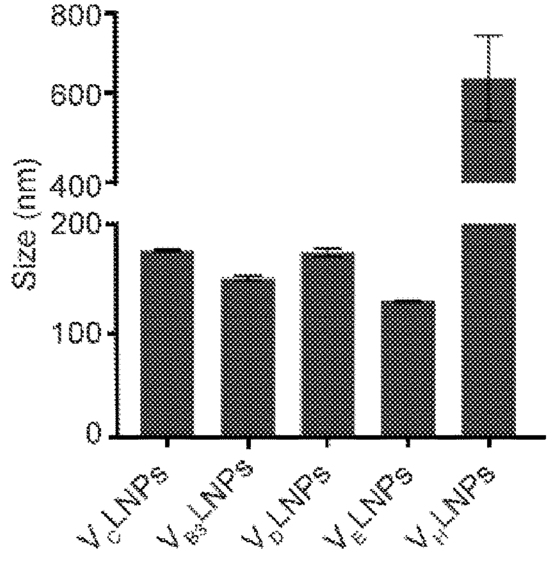
Figure 7B:
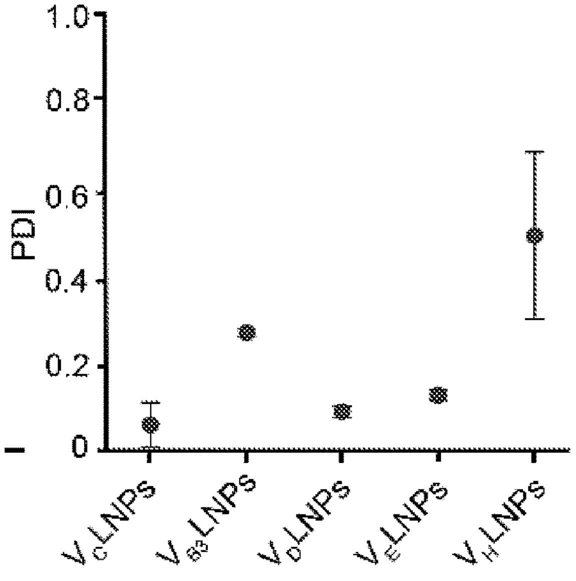
Figure 7C:
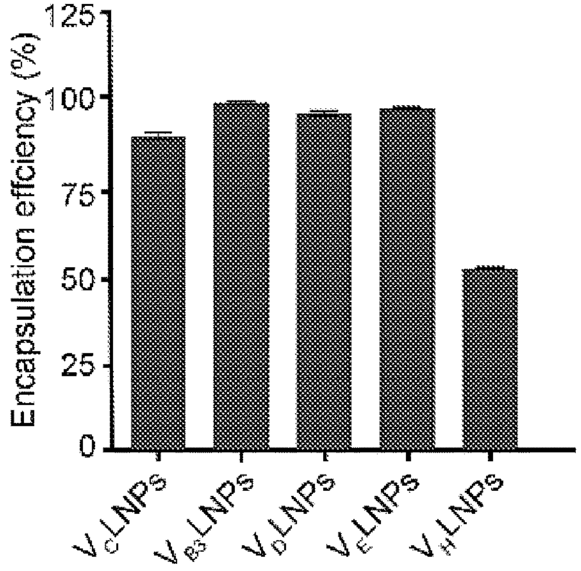
Figure 7D:
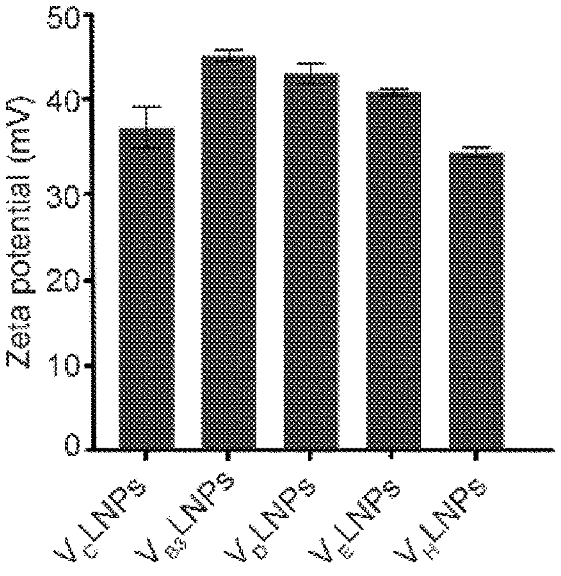
Figure 7F:
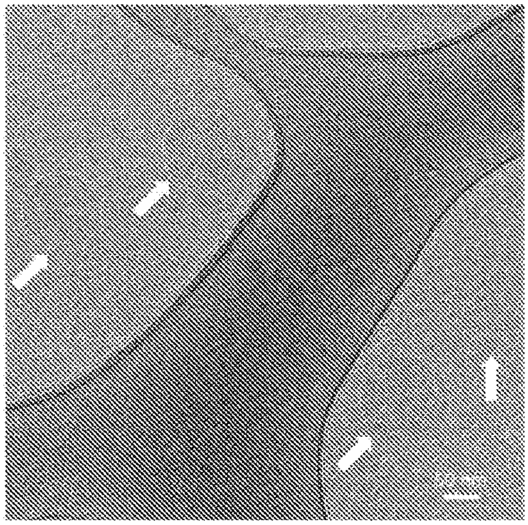
Figure 8A:
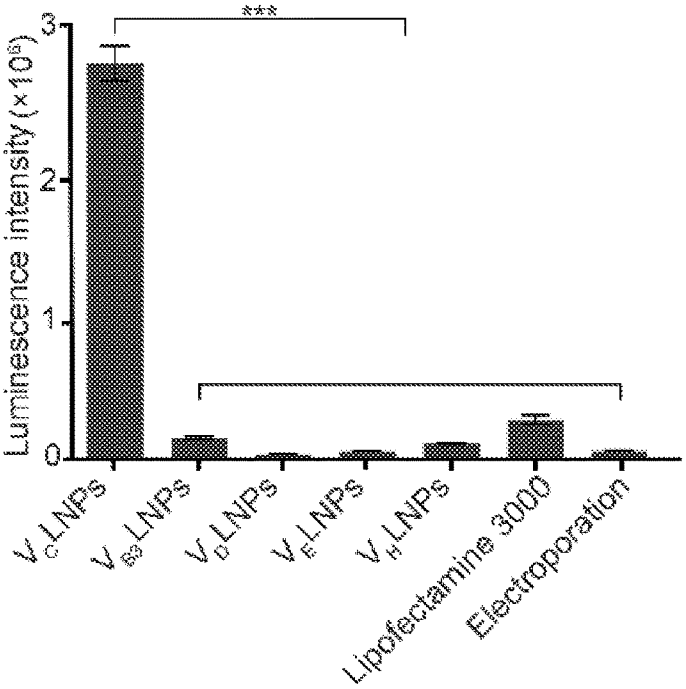
Figure 8B:
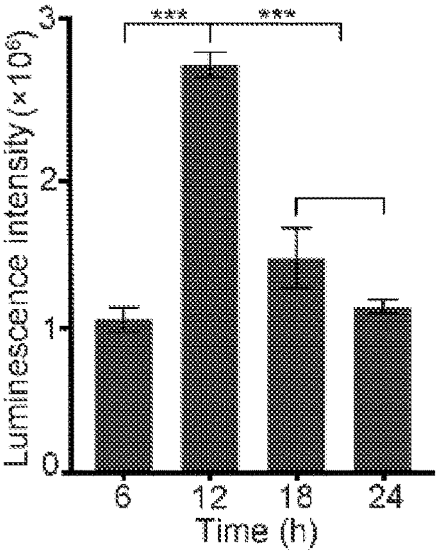
Figure 8E:
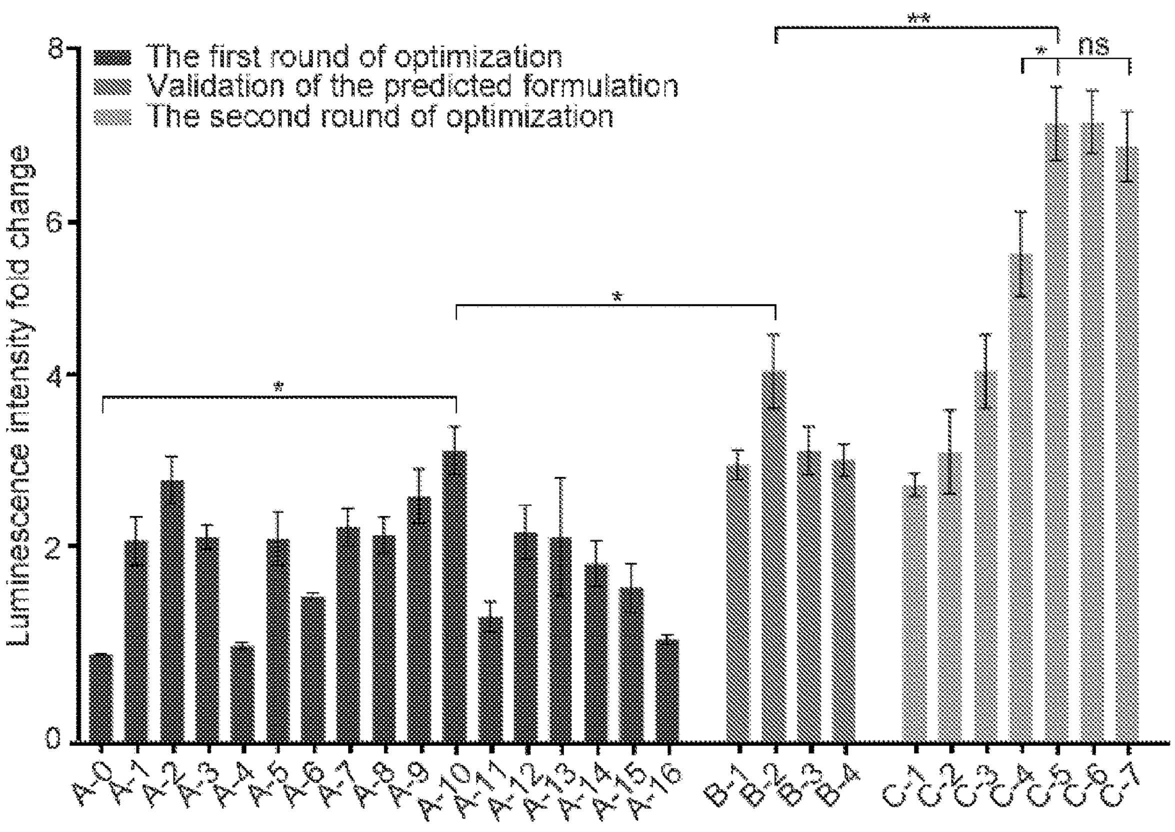
Figure 8F:
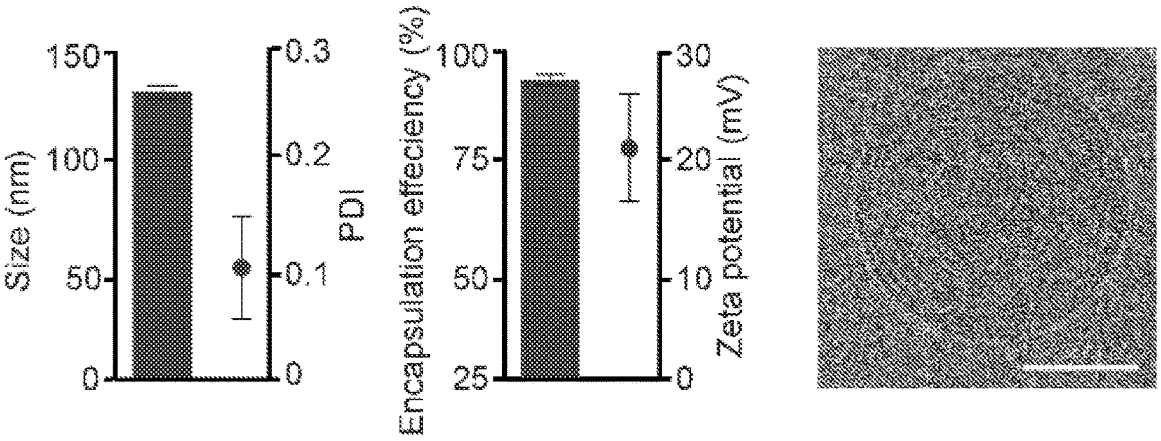

Next, these vitamin-derived lipids were formulated into vitamin-lipid nanoparticles (VLNPs) accordingly. Particle size of VLNPs ranged from 127±1 to 174±1 nm with polydispersity index (PDI)<0.3 except VHLNPs (FIGS. 7*a* and 7*b*). The entrapment efficiency of mRNA was within the range from 52% to 99% and all VLNPs were positively charged (FIGS. 7*c* and 7*d*). In the initial screening in the RAW264.7 cells using the mRNA encoding firefly luciferase, VcLNPs were 20-fold more effectively for mRNA delivery than other four VLNPs (FIG. 8*a*). Moreover, VcLNPs were 10-fold better than Lipofectamine 3000 and were 50-fold better than electroporation at the same mRNA concentration (FIG. 8*a*). In addition, the highest luminescence intensity of VcLNP group was observed at 12 h from 6 to 24 h (FIG. 8*b*). In order to further investigate the formulation of VcLNPs, an orthogonal array design was performed to fine-tune the component ratios. 16 different formulations were prepared based on an $L_{16}$ $(4)^4$ orthogonal array design table (FIG. 7*e*). Formulation B2 (Lipid:DOPE:Cholesterol=30:30:40) emerged from this study (FIGS. 8*c* and 8*e*). Then, delivery efficiency was validated by comparison with the top formulation A10 (Lipid:DOPE:Cholesterol=30:30:50) in the orthogonal table. The luminescence intensity of the predicted formulation B2 was significantly higher than formulation A10 (P<0.05, FIGS. 8*d* and 8*e*). To further improve mRNA delivery efficiency, the mass ratio of Vc-Lipid:mRNA of formulation B2 from 5:1 to 20:1 was examined (FIG. 8*d*). In the second round of characterization, the luminescence intensity was enhanced as the mass ratio of Vc-Lipid:mRNA was increased until the mass ratio is 15:1 (formulation C5, FIG. 8*e*). Formulation C5 of VcLNPs was positively charged in a spherical morphology from the Cryo-TEM image (FIG. 8*f* and FIG. 7*f*). Based on these results, this VcLNPs formulation with improved mRNA delivery efficiency over 7-fold than its initial formulation was chosen for further studies.

Figure 13A:
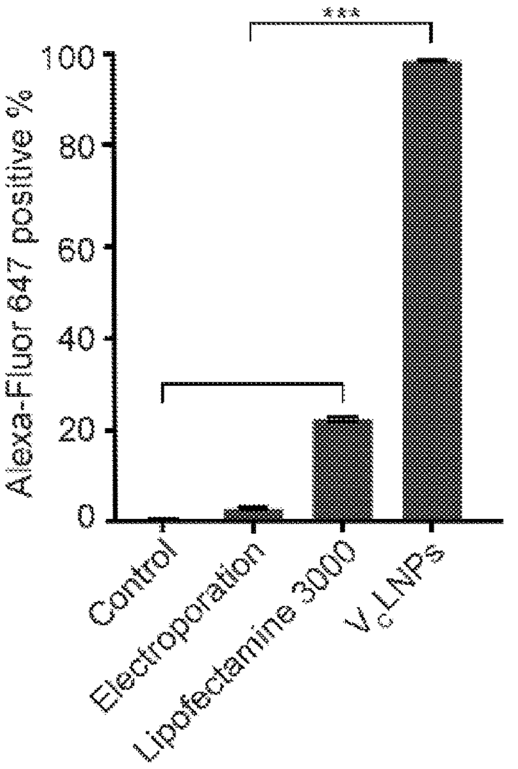
FIG. 13A-13I. Cellular uptake, endocytosis pathways, endosomal escape, and therapeutic effects of MAC-RAWs in MDRSA induced sepsis mice with immunosuppression. a-b, Cellular uptake after treatment with VcLNPs, Lipofectamine 3000 and electroporation. a, Percentage of Alexa-Fluor 647 positive cells; b, Fluorescence intensity of cells. c-d, Cellular uptake in the presence of endocytic inhibitors, EIPA, MPCD, and CPZ, which inhibit macropinocytosis, caveolae-, and clathrin-mediated endocytosis, respectively. c, Percentage of Alexa-Fluor 647 positive cells; d, Fluorescence intensity of cells. e-f, Confocal microscopy of the RAW264.7 cells incubated with calcein alone or calcein and VcLNPs containing Alexa-Fluor 647 RNA. e, Calcein alone; f, Calcein and VcLNPs containing Alexa-Fluor 647 RNA. g, 3D confocal microscopy images of the RAW264.7 cells incubated with eGFP-CatB mRNA VcLNPs. h, The percentage of the RAW264.7 cells normalized to the PBS-RAW group at 12 h. Data in a, b, c, d, and h, are the mean±s.d., triplicate. i, Percentage survival of mice with sepsis treated with PBS, MAC-RAWs (i.v.), or MAC-RAWs (i.p.+i.v.). The number of mice was 6 for each group. *P<0.05, P<0.01, *P<0.001; ns, not significant (two-tailed Student's t-test).
Figure 13B:
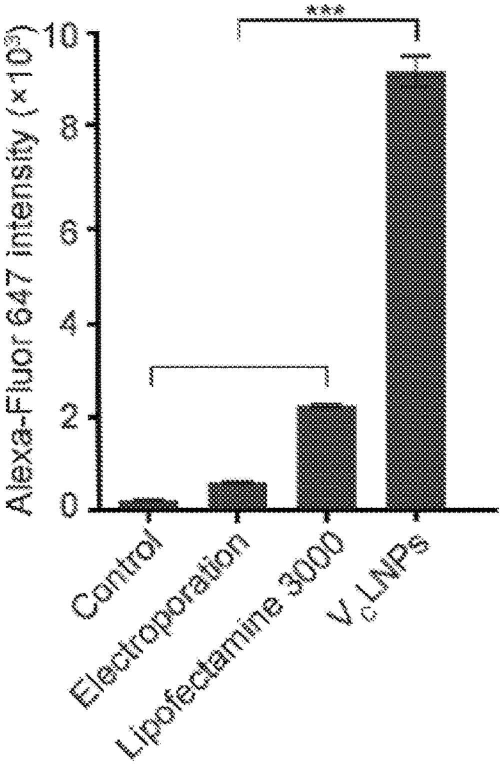
Figure 13C:
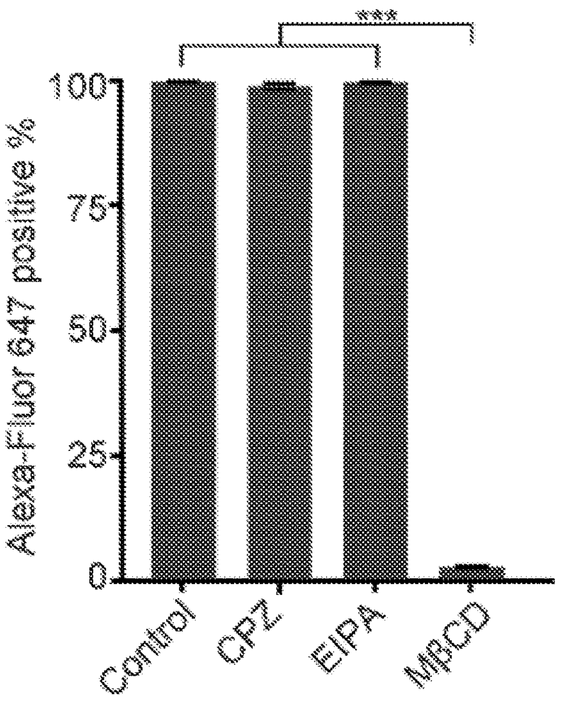
Figure 13D:
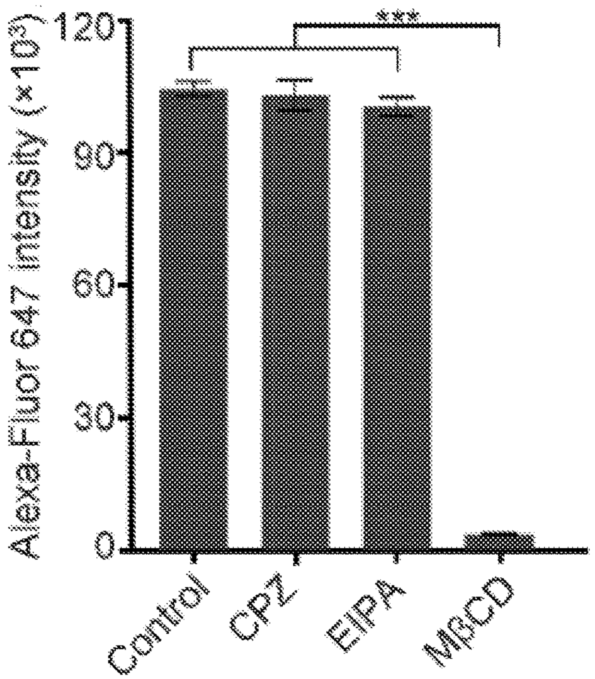
Figure 13E:
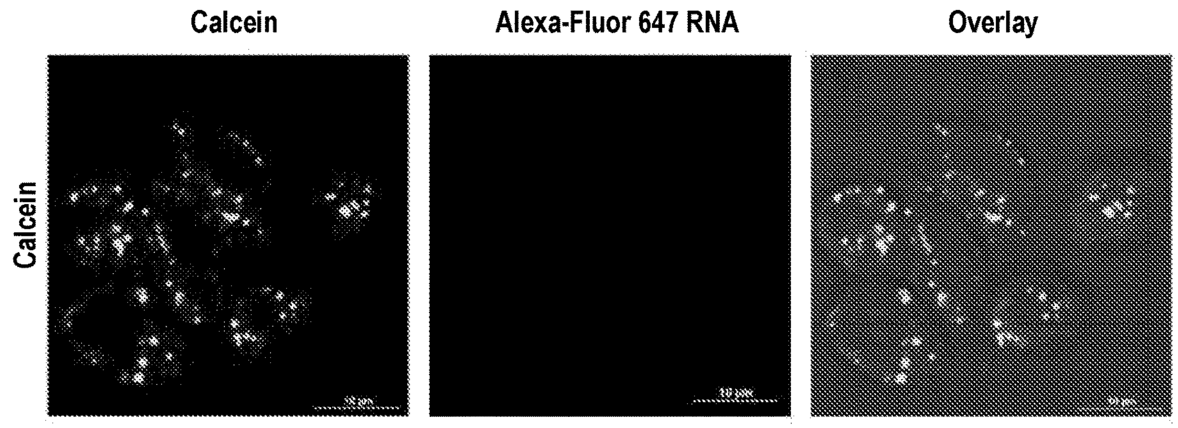
Figure 13F:
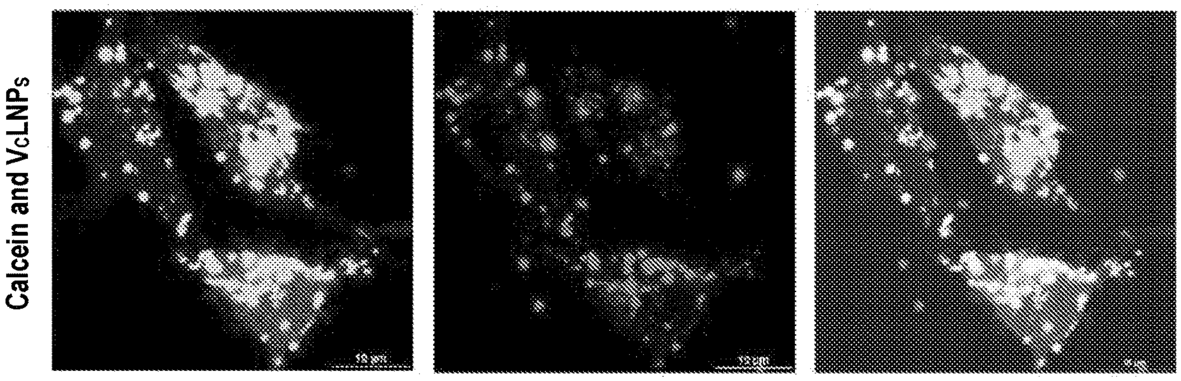

Using a fluorescent probe, Alexa-Fluor 647 labelled RNA, 99.2% Alexa-Fluor 647 positive cells was observed in the group of VcLNPs, 21.5% in the group of Lipofectamine 3000, and 2.4% in the group of electroporation (FIG. 13*a*). Moreover, the fluorescence intensity was around 4-fold and 16-fold, respectively higher in the VcLNPs-treated cells compared to the cells treated with Lipofectamine 3000 or electroporation (FIG. 13*b*). These data demonstrated efficient cellular uptake of the VcLNPs. Then, the cells were incubated with VcLNPs in the presence of different endocytic inhibitors, 5-(N-methyl-N-isopropyl)amiloride (EIPA), methyl-beta-cyclodextrin (MPCD), and chlorpromazine hydrochloride (CPZ), which inhibit macropinocytosis, caveolae- and clathrin-mediated endocytosis, respectively. Cellular uptake of VcLNPs was dramatically reduced by about 96% in the group of MPCD (FIGS. 13*c* and 13*d*), indicating a major role of caveolae-mediated endocytosis for these VcLNPs. In order to explore the endosomal escape mechanism, a calcein assay was performed. Calcein, a membrane-impermeable dye, is normally entrapped into the cell endosomes. Cells were treated with both calcein and VcLNPs, and diffused green fluorescence in the cell cytoplasm was observed, indicating that endosome membranes were ruptured and consequently VcLNPs are released to the cytoplasm (FIGS. 13*e* and 13*f*).

Figure 8G:
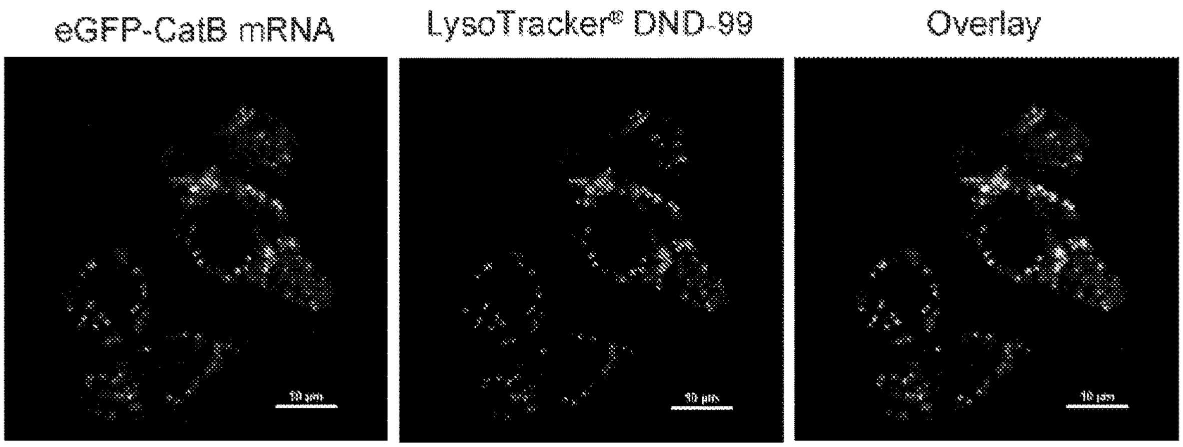
Figure 8H:
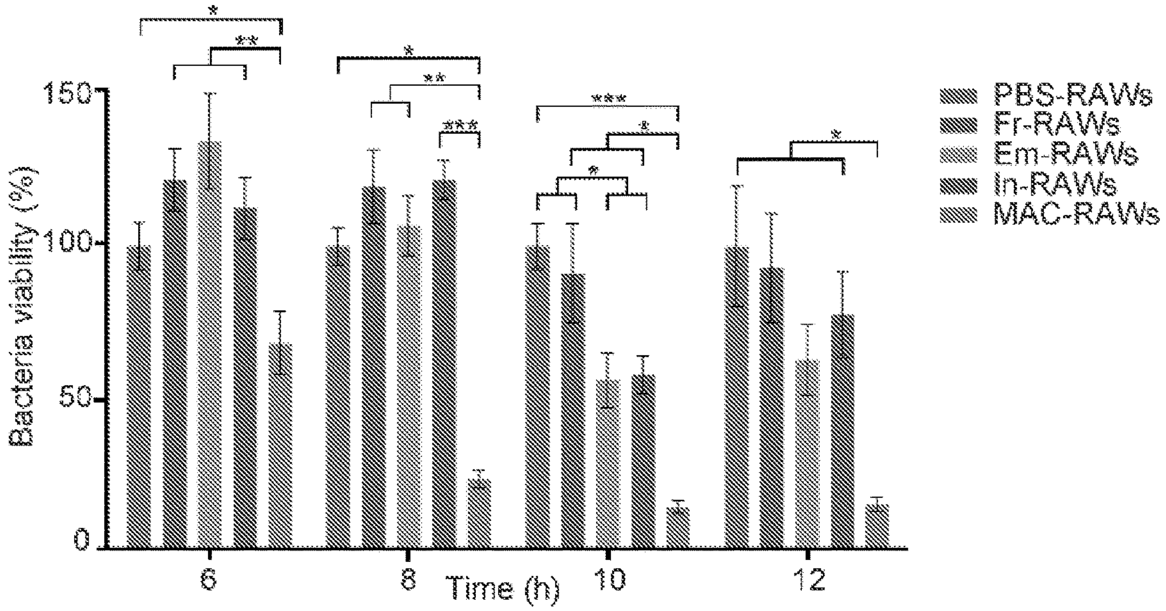
Figure 13G:
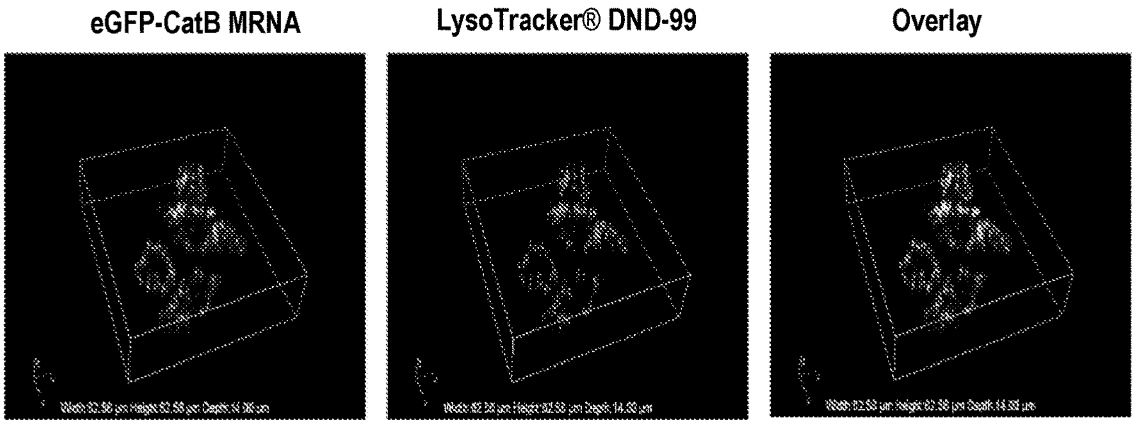
Figure 13H:
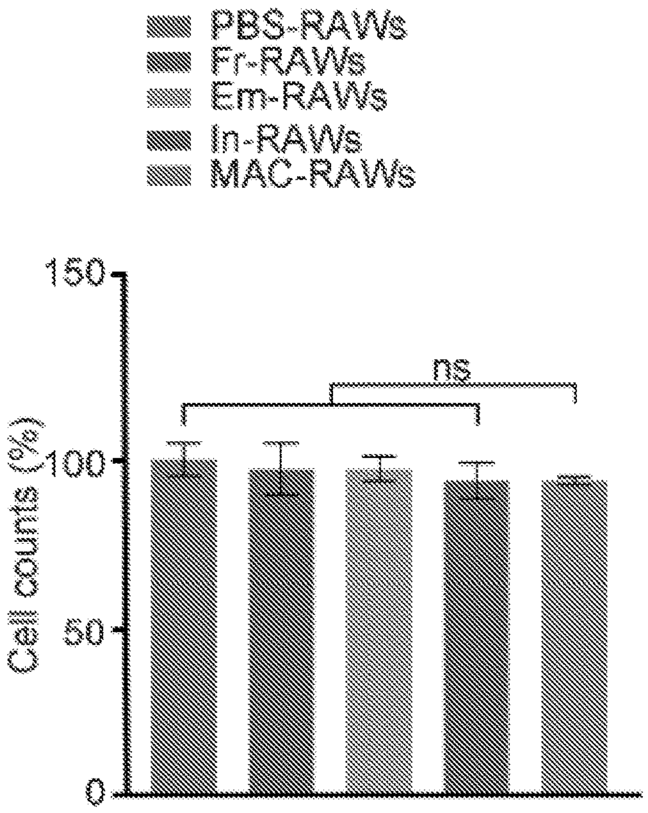

To test whether the cathepsin B (CatB) was able to transport the payload into the lysosomes, the eGFP-CatB mRNA was constructed and delivered into the RAW264.7 cells using VcLNPs. The confocal microscopy of the live cells exhibited that eGFP-CatB co-localized with the LysoTracker® Red DND-99 in the lysosomes, with a Pearson's correlation coefficient of 0.91±0.15 (FIG. 8*g* and FIG. 13*g*), indicating that the CatB carried its payload into the lysosomes. Then, to evaluate the bactericidal activity of macrophages loaded with the AMP-IB367 in the lysosomes (MACs), the intracellular survival of multidrug resistant *Staphylococcus aureus* (MDRSA) was quantified in the RAW264.7 cells treated by PBS (PBS-RAWs), free AMP-CatB mRNA (Fr-RAWs), empty VcLNPs (Em-RAWs), AMP-CatB mRNA VcLNPs/CatB inhibitor II (In-RAWs), and AMP-CatB mRNA VcLNPs (MAC-RAWs). Relative to other four treatments, MAC-RAWs showed the strongest bactericidal activity at all the time points tested with the percentage inhibition from 33% to 87% (FIG. 8*h*). When the CatB function was inhibited using the CatB inhibitor II, the bactericidal activity was dramatically reduced (FIG. 8*h*), indicating the importance of the release of AMP-IB367. No significant differences in the number of cells were observed in all five groups (FIG. 13*h*); therefore, these results demonstrated that the pre-stored AMP-IB367 was able to hinder immune evasion by bacteria and eliminate them in the phagolysosomes.

Figure 9A:
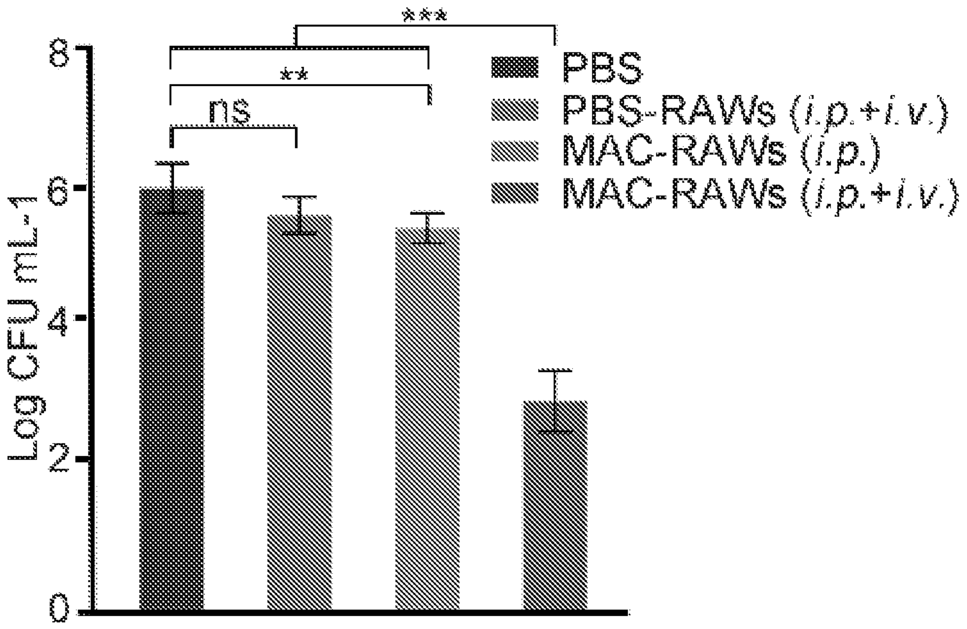
FIGS. 9A-9G. Therapeutic effects of MAC-RAWs in MDRSA induced sepsis mice with immunosuppression. a) Bacterial burden in the blood at 24 h after cell transfer. b, Percentage survival of mice with sepsis. c)-e) The body weights (BWs), white blood cells (WBCs), and lymphocytes (LYMs) of mice with sepsis. c) BWs; d) WBCs; e) LYMs. f) and g) Bacterial burden in the blood of each survived mouse treated by MAC-RAWs (i.p.+i.v.). The number of mice in the groups of PBS, PBS-RAW (i.p.+i.v.), MAC-RAW (i.p.), and MAC-RAW (i.p.+i.v.) were 8, 10, 10, and 12, respectively. Data in a, c, d, and e are the mean±s.d. *P<0.05, P<0.01, *P<0.001; ns, not significant (two-tailed Student's t-test). ND, not detectable.
Figure 9B:
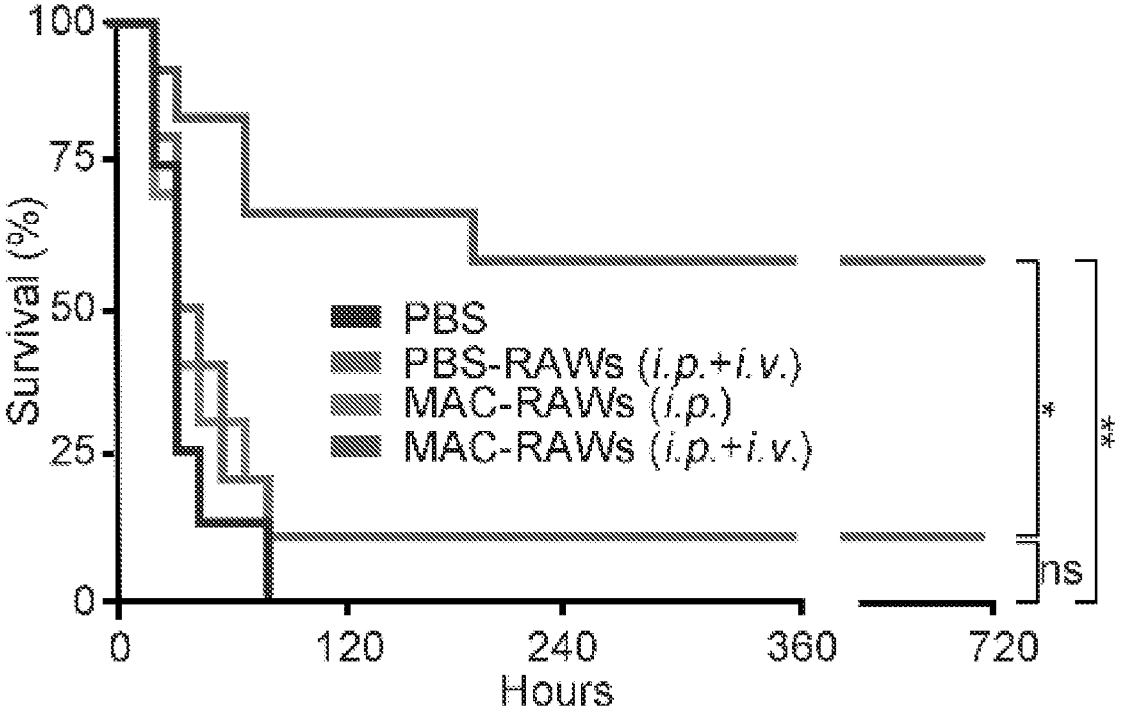
Figure 13I:
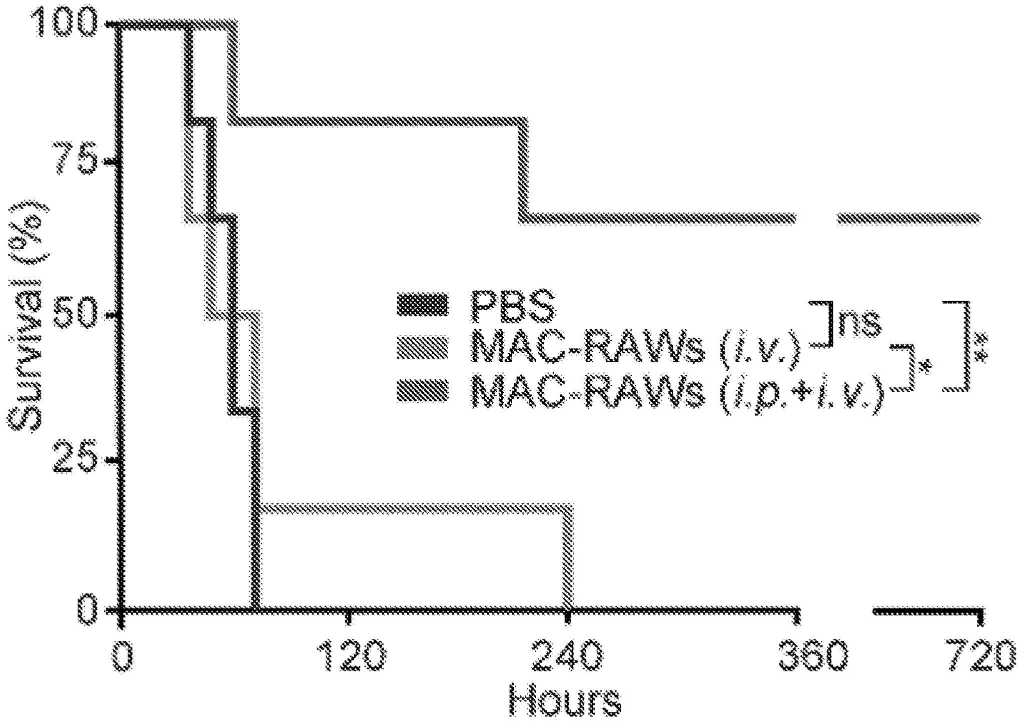

Given the potent in vitro bactericidal activity of MAC-RAWs, testing was performed assessing the therapeutic effects in MDRSA induced sepsis mice with immunosuppression. After 3 consecutive days of cyclophosphamide (CY) treatment, the decrease of body weights (BWs), white blood cells (WBCs), and lymphocytes (LYMs) mimicked an immunocompromised state in the sepsis patient. After infected by MDRSA, the mice were treated with PBS, PBS-RAWs, or MAC-RAWs. PBS-RAWs were injected both intraperitoneally (i.p.) and intravenously (i.v.) to treat the local and blood bacteria. For the MAC-RAWs, three administration methods were conducted with the same total cell number: i.p. injection alone, i.v. injection alone, and i.p.+i.v. injections. Because the lethality in immunosuppressed sepsis is associated with ineradicable pathogens, the bacterial colony forming units (CFUs) in the mouse blood were measured after 24 h of cell transfer. Similar to PBS treatment, PBS-RAWs did not reduce bacterial burden in the blood, while MAC-RAWs administrated via i.p. injection alone (MAC-RAWs (i.p.)) and MAC-RAWs administrated via both i.p. and i.v. injection (MAC-RAWs (i.p.+i.v.)) significantly reduced the bacterial CFUs in the blood ($P<0.01$ and $P<0.001$, respectively) (FIG. 9*a*). These results showed the bactericidal activity in vivo. Interestingly, MAC-RAWs (i.p.+i.v.) showed much stronger ability to clear bacteria than MAC-RAWs (i.p.) ($P<0.001$, FIG. 3*a*). Moreover, on the $30^{th}$ day, the survival rate of MAC-RAW (i.p.+i.v.) group was 58%, significantly improved compared to MAC-RAW (i.p.) group ($P<0.01$, FIG. 9*b*). Similarly, MAC-RAWs (i.p.+i.v.) showed better therapeutic effects on survival rate ($P<0.05$) than MAC-RAWs (i.v.) (FIG. 13*i*).

Figure 9C:
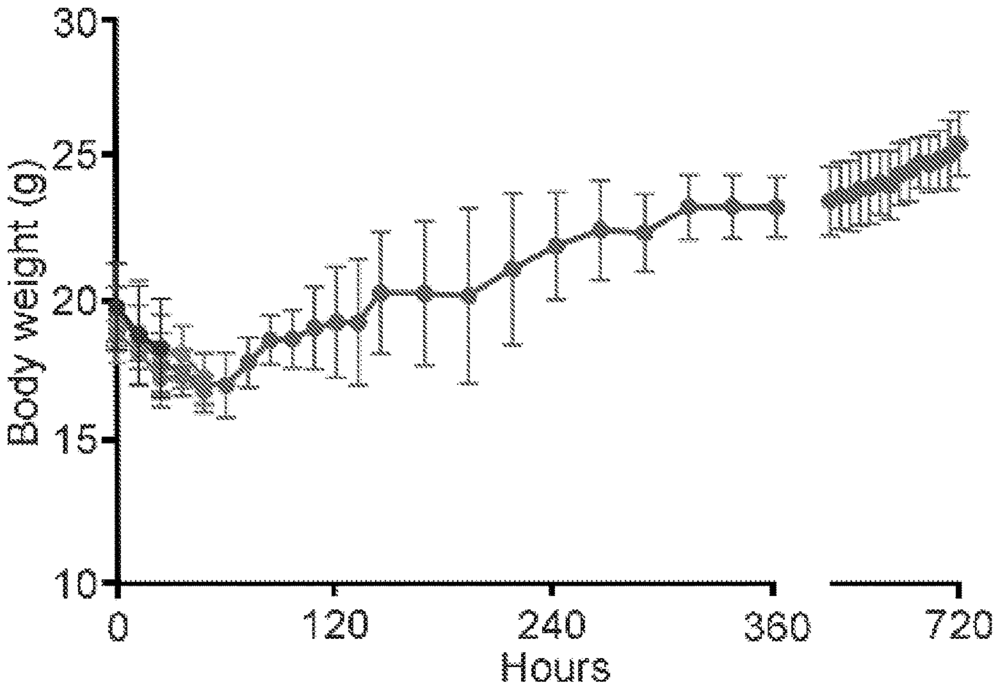
Figure 9D:
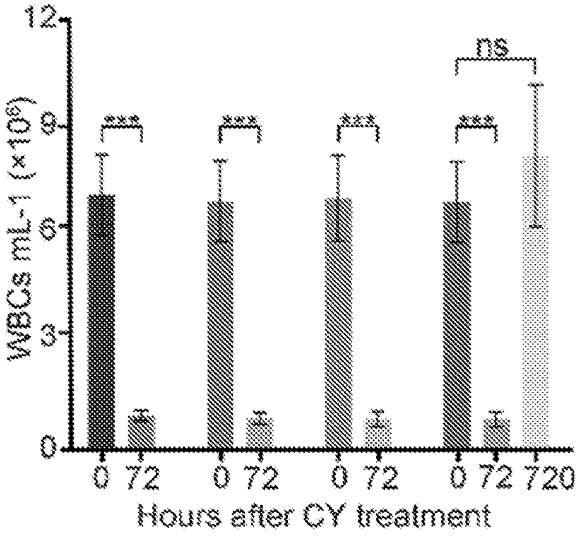
Figure 9E:
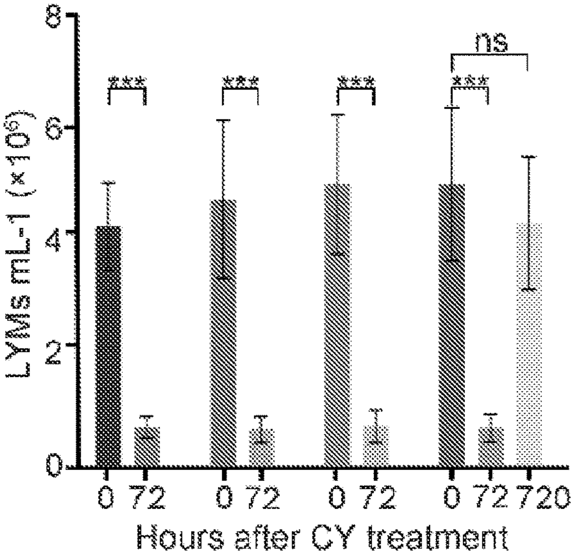
Figure 9F:
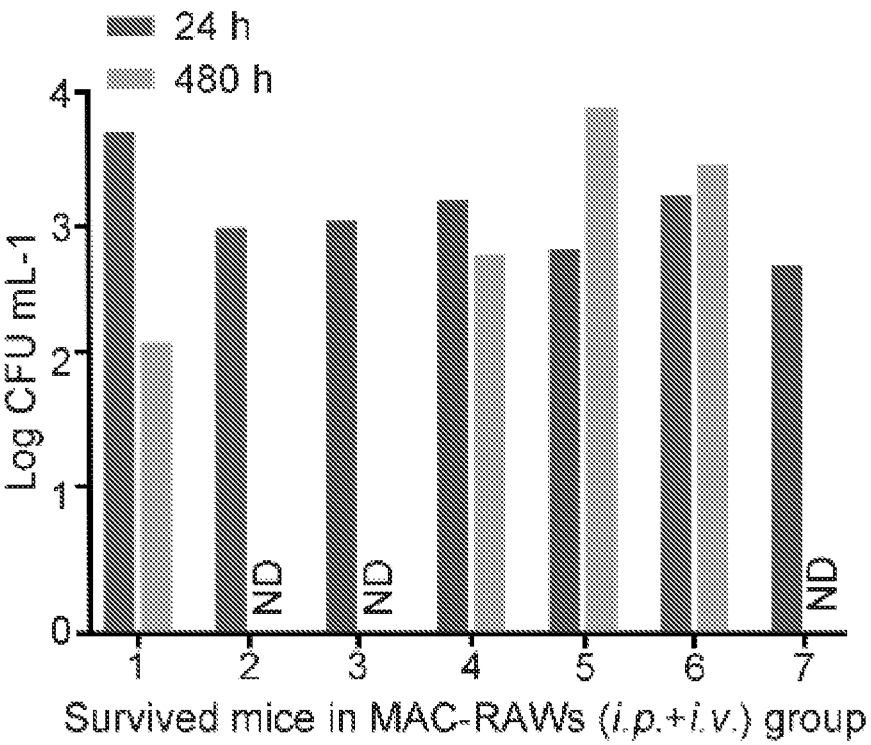
Figure 9G:
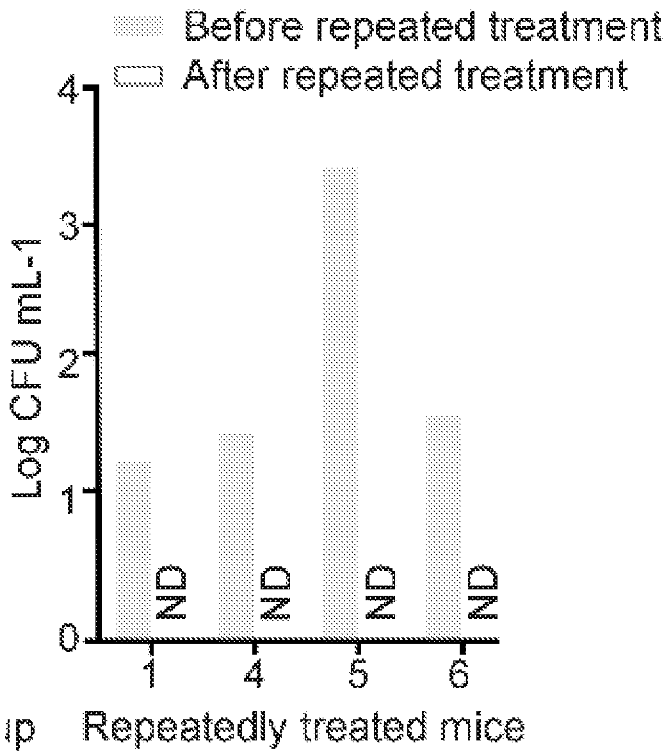

In the MAC-RAW (i.p.+i.v.) group, bacteria in the blood were not detectable in 3 out of the 7 survived mice at the 480 h (FIG. 9*f*). Then, a repeat treatment for the 4 mice with persistent infections were performed, which consequently cleared the remaining bacteria in these mice (FIG. 9*g*). After a month, the levels of BW, WBC and LYM of the 7 survived mice fully recovered (FIGS. 9*c* to 9*e*). Moreover, bacteria were not detectable in the blood and major organs (heart, liver, spleen, lung, and kidneys) in these mice.

Figure 10A:
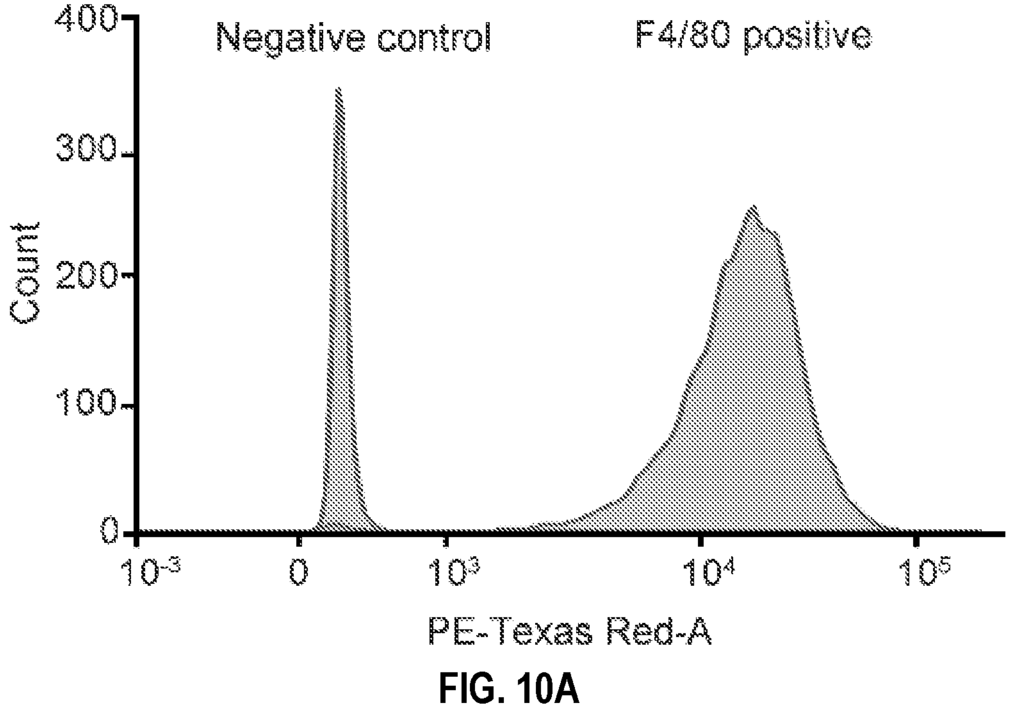
FIGS. 10A-10H. Screening of VLNPs in BMDMs and intracellular survival of MDR bacteria in BMDMs. a) F4/80, a mature macrophage maker, positive cells (83.5±0.7%). b) mRNA delivery efficiency of VLNPs in BMDMs. c) Expression kinetics of mRNA delivered by VcLNPs in BMDMs. d) and f) Intracellular survival of MDR bacteria in BMDMs treated by PBS (PBS-BMDMs), free AMP-CatB mRNA (Fr-BMDMs), empty VcLNPs (Em-BMDMs), AMP-CatB mRNA VcLNPs/CatB inhibitor II (In-BMDMs), and AMP-CatB mRNA VcLNPs (MAC-BMDMs). d) MDRSA; f) MDR *E. coli*. e) and g) The percentage of the BMDMs normalized to the PBS-BMDM group at 12 h. e) MDRSA; g) MDR *E. coli*. h) Cytotoxicity of VcLNPs encapsulating AMP-CatB mRNA in BMDMs was determined by the MTT assay. *P<0.05, P 15<0.01, *P<0.001; ns, not significant (two-tailed Student's T-test). Data in this figure are the mean±s.d., n=3 independent experiments.
Figure 10B:
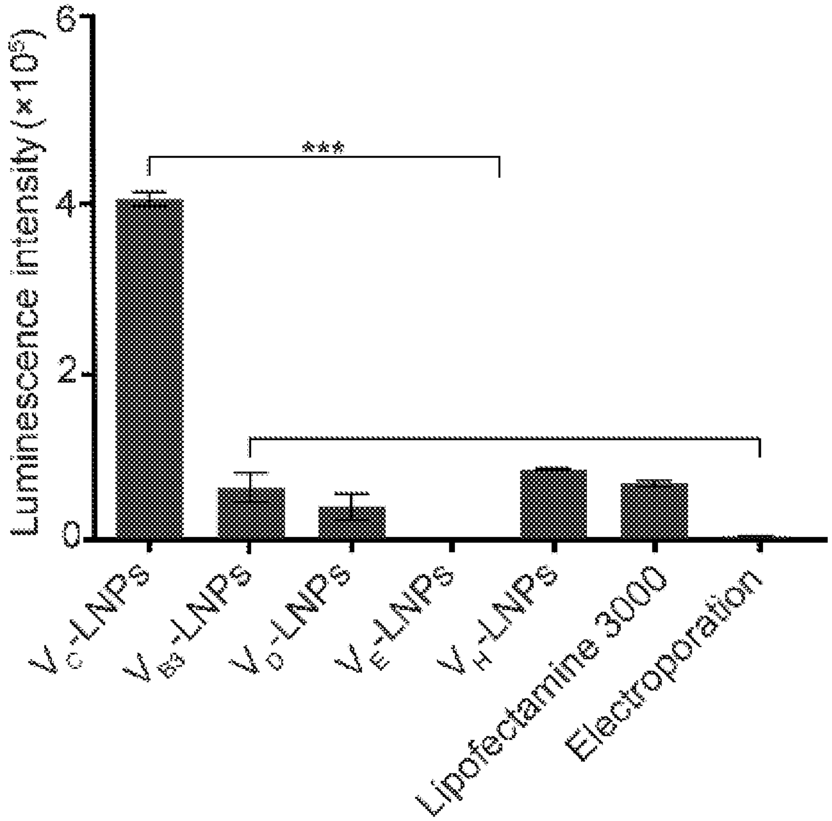
Figure 10C:
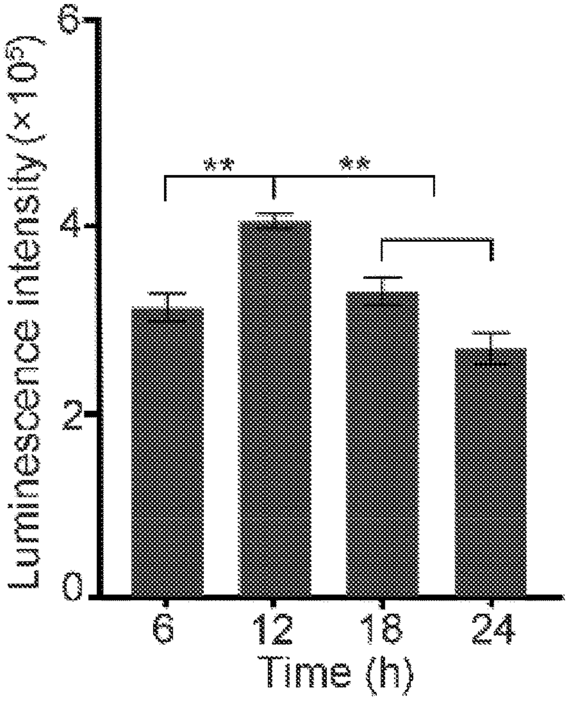
Figure 10D:
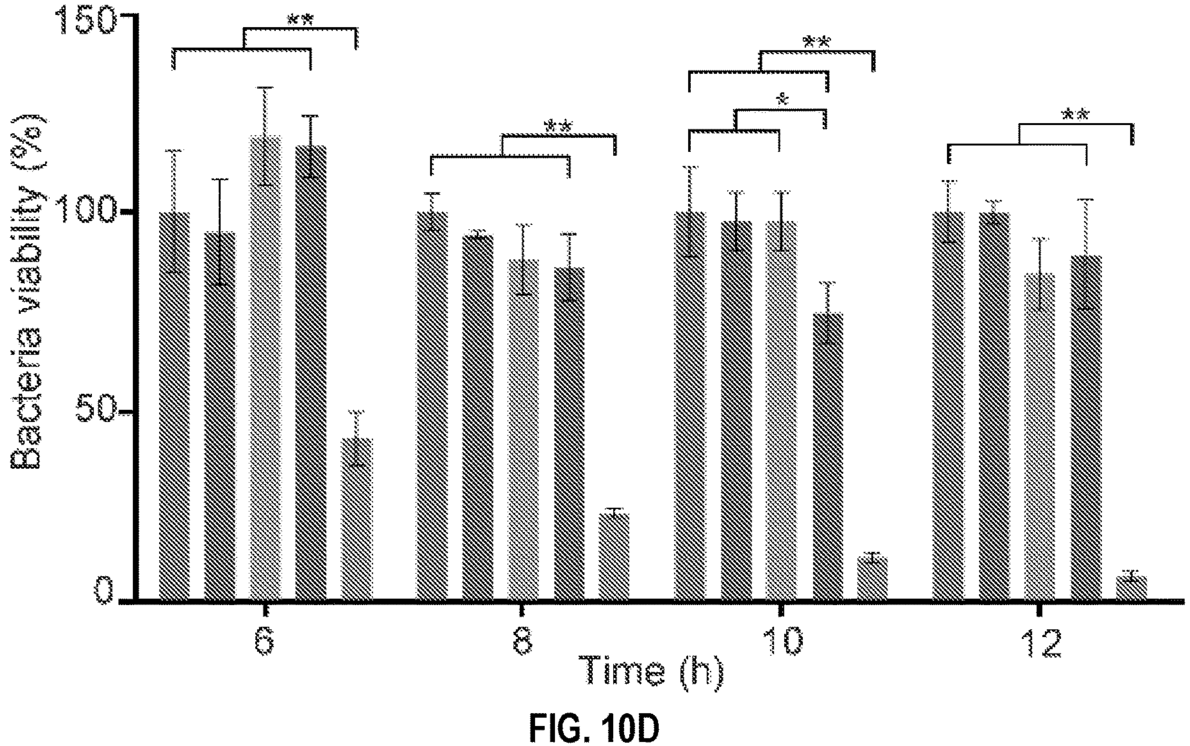
Figure 10E:
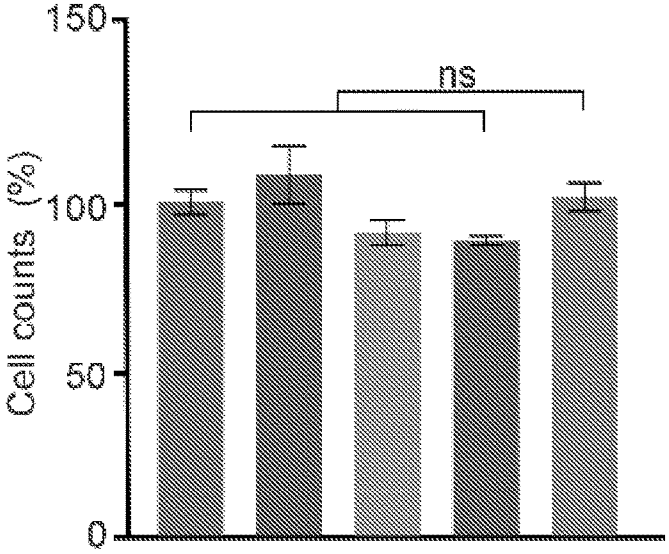
Figure 10F:
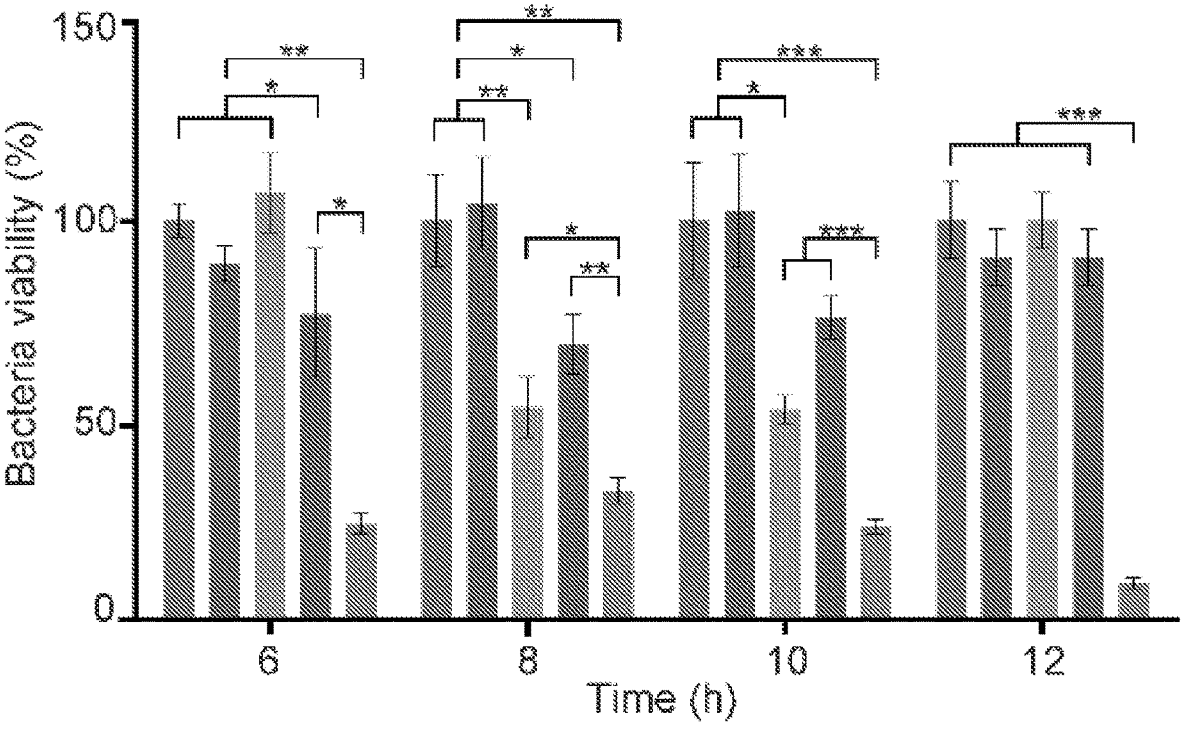
Figure 10G:
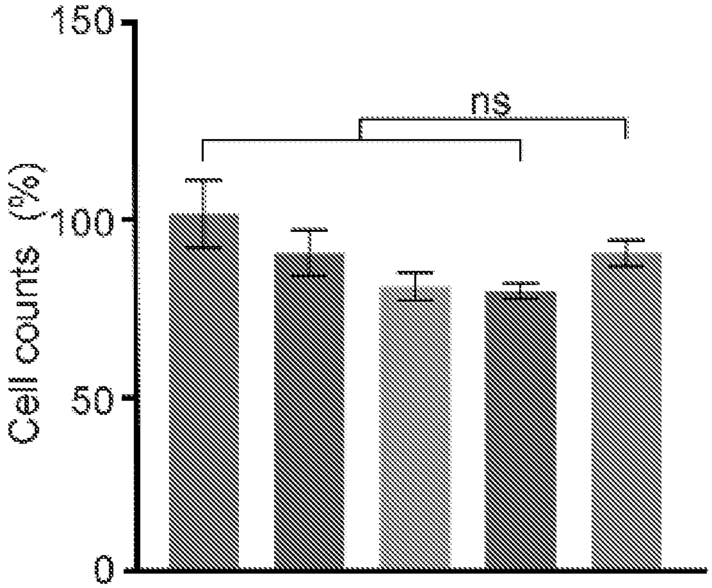
Figure 10H:
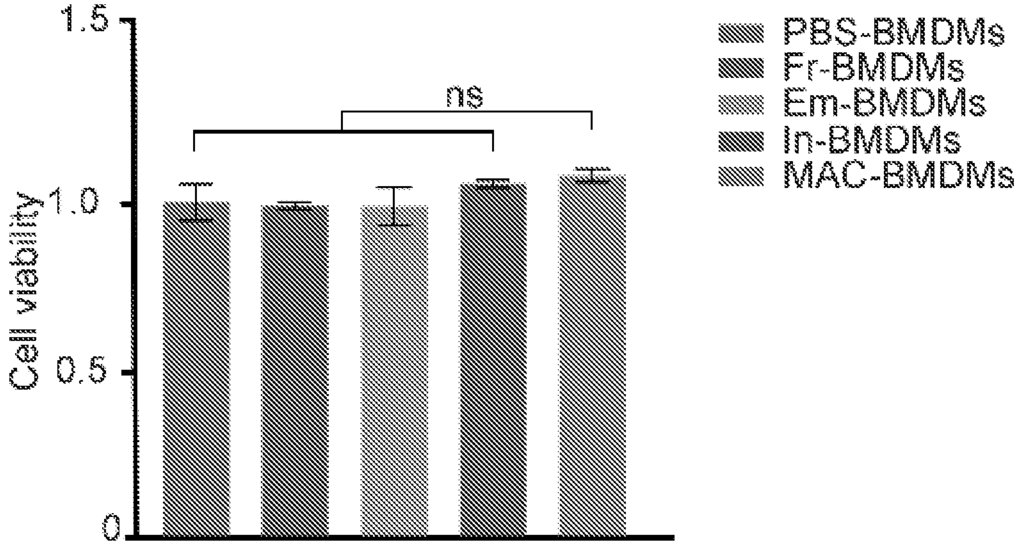

The bactericidal activity using primary bone marrow derived macrophages (BMDMs) was evaluated next, which are translatable for clinical applications. BMDMs were generated from the mouse bone marrow as reported in the literature and confirmed ~83.5% cells were F4/80 positive. (FIG. 10*a*). Then, VLNPs were also screened and tested for their expression profile in BMDMs. Similar to the results in the RAW264.7 cells, VcLNPs were 5-fold more effective in mRNA delivery than other four VLNPs, 6-fold more effective than Lipofectamine 3000, and 150-fold more effective than electroporation. (FIG. 10*b*). Meanwhile, VcLNPs in BMDMs followed a consistent expression profile with the maximum luminescence intensity at 12 h. (FIG. 10*c*). Next, MAC-BMDMs were prepared using AMP-CatB mRNA VcLNPs, and evaluated regarding the in vitro bactericidal activity against MDRSA and multidrug resistant *Escherichia coli* (MDR *E. coli*). Compared to BMDMs treated by PBS (PBS-BMDMs), free AMP-CatB mRNA (Fr-BMDMs), empty VcLNPs (Em-BMDMs), and AMP-CatB mRNA VcLNPs/CatB inhibitor II (In-BMDMs), AMP-CatB mRNA VcLNPs (MAC-BMDMs) showed the strongest bactericidal activity against both MDRSA and MDR *E. coli* with the highest percentage inhibition of 85% and 74%, respectively (FIGS. 10*d* and 10*f*). In addition, all five groups showed comparable cell numbers (FIGS. 10*e* and 10*g*) and AMP-CatB mRNA VcLNPs did not induce obvious cytotoxicity in BMDMs (FIG. 10*h*).

Figure 11A:
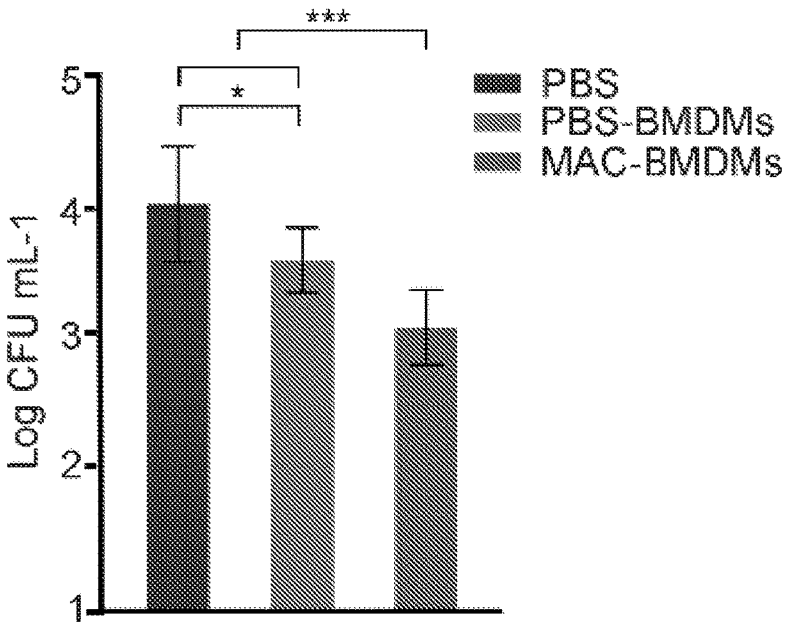
FIG. 11A-11G. Therapeutic effects of MAC-BMDMs in MDRSA induced sepsis mice with immunosuppression. a) Bacterial burden in the blood at 24 h after cell transfer. b) Percentage survival of mice with sepsis. c)-e) The BWs, WBCs, and LYMs of mice with sepsis. c) BWs; d) WBCs; e) LYMs. f) and g) Bacterial burden in the blood of each survived mouse treated by MAC-BMDMs. The number of mice in the groups of PBS, PBS-BMDM, and MAC-BMDM were 8, 10, and 12, respectively. Data in a, c, d, and e are the mean±s.d. *P<0.05, P<0.01, *P<0.001; ns, not significant (two-tailed Student's f-test). ND, not detectable.
Figure 11B:
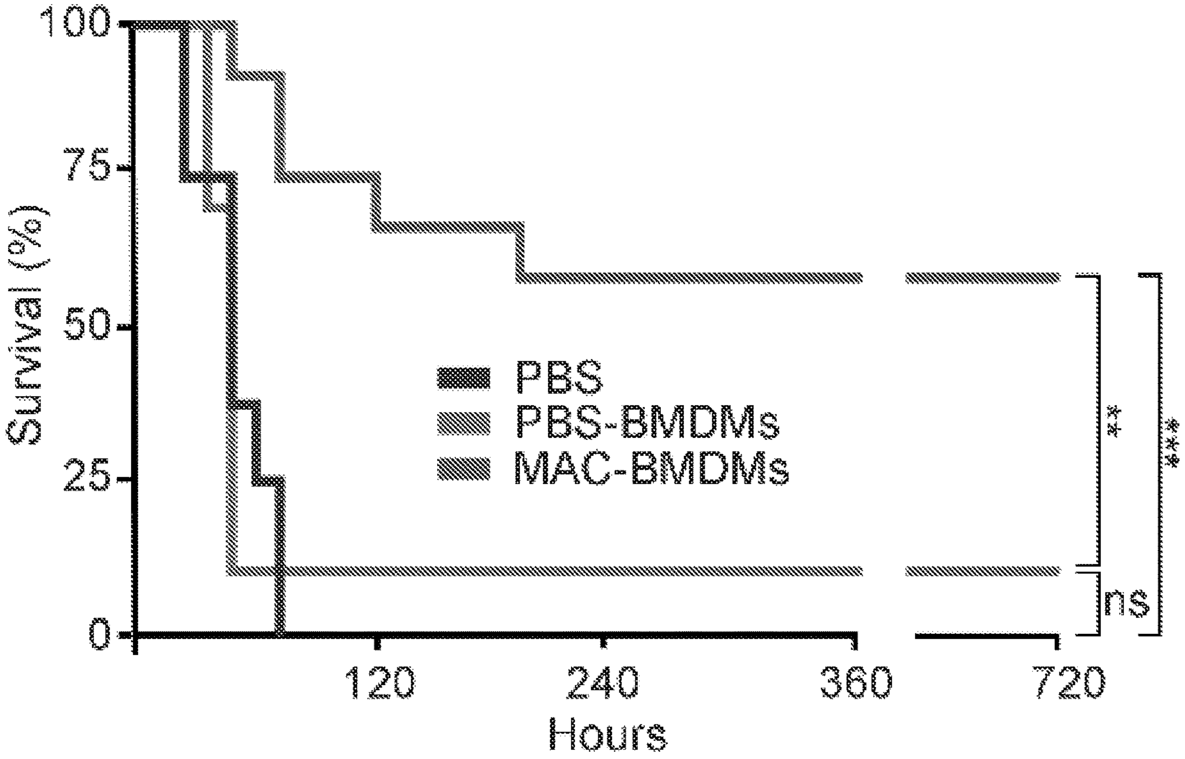
Figure 11C:
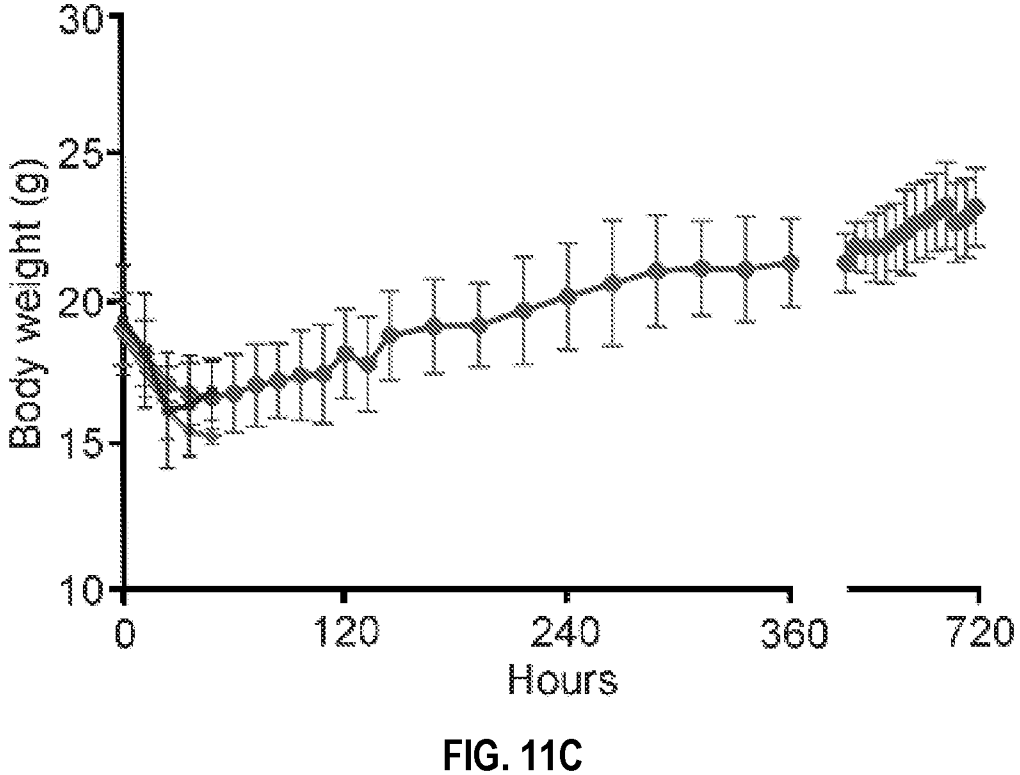
Figure 11D:
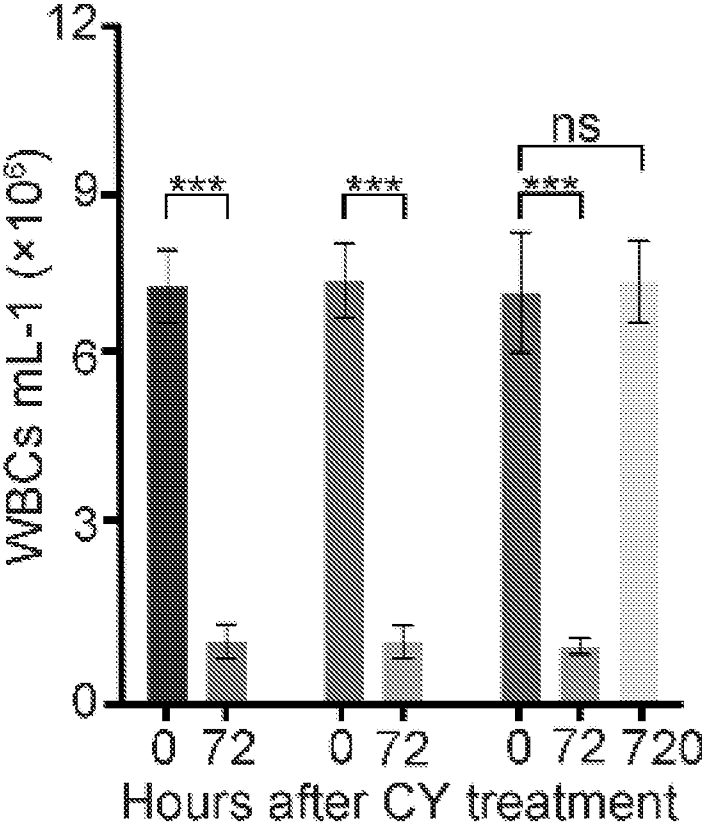
Figure 11E:
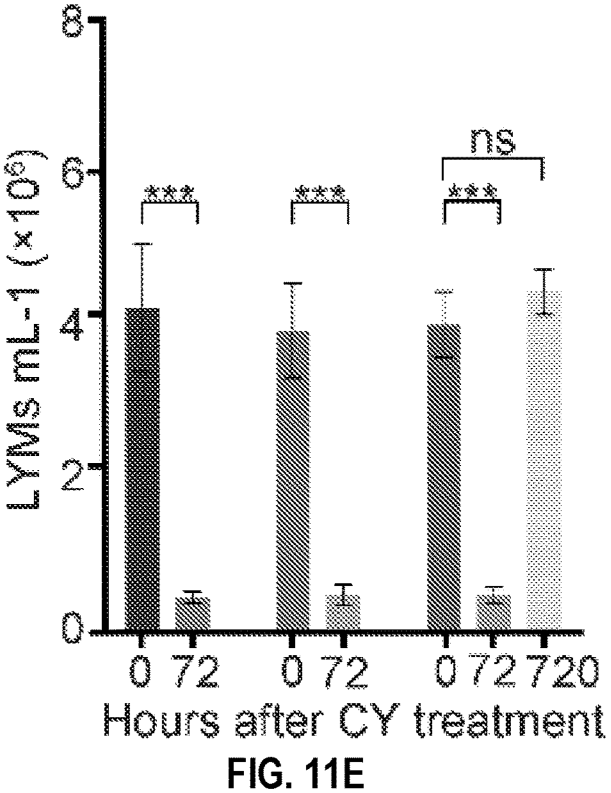
Figure 11F:
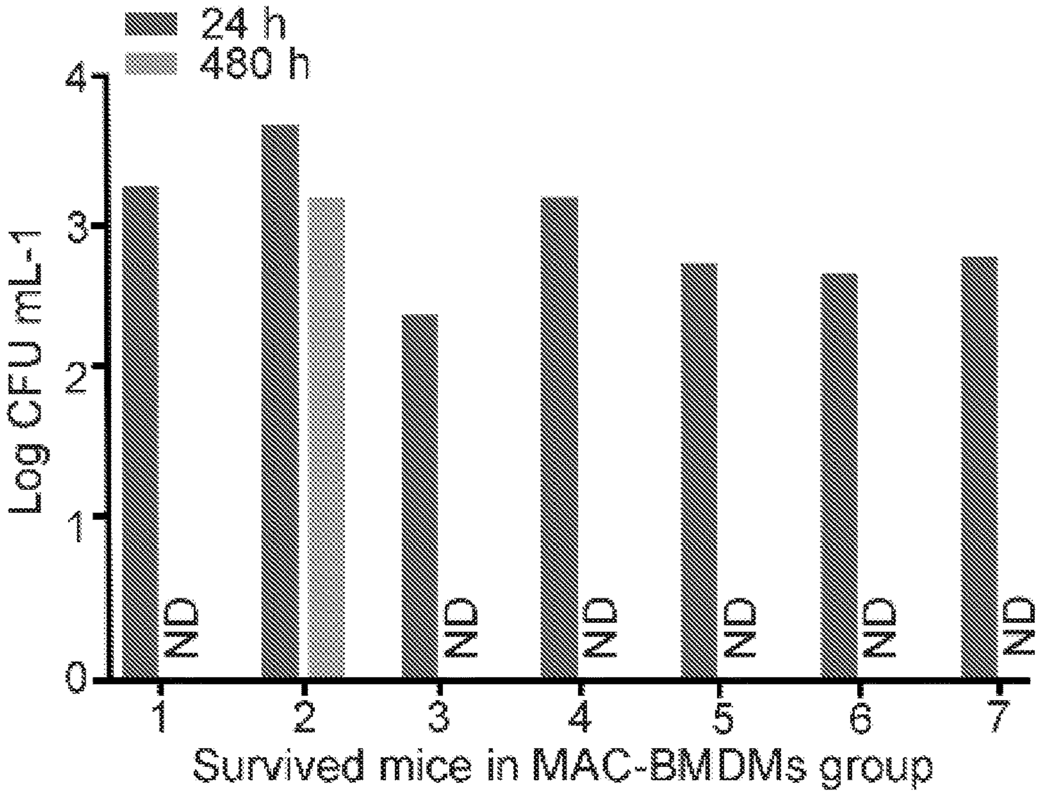
Figure 11G:
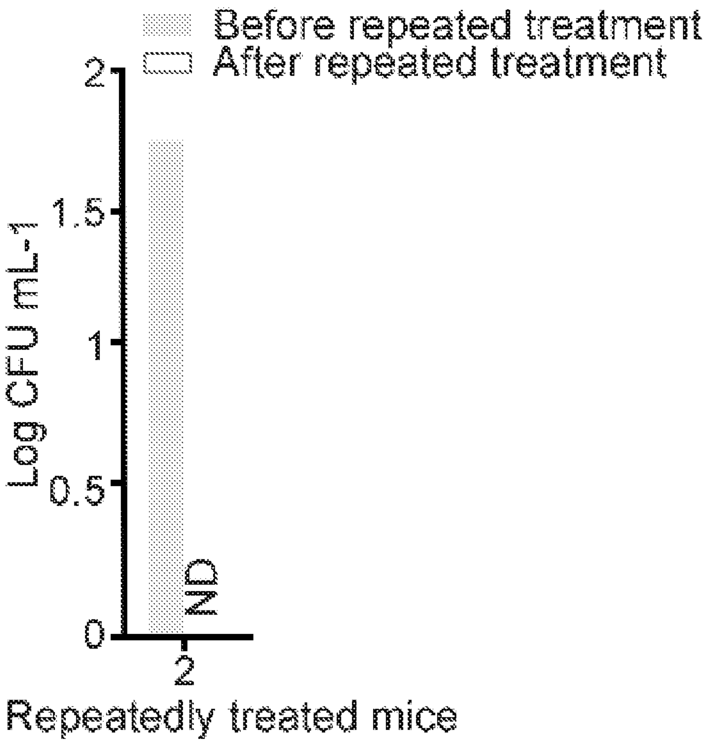

After validating the results in vitro, MAC-BMDMs were applied to mice with immunosuppression to treat MDRSA induced sepsis. Based on the data from the RAW264.7 cells, MAC-BMDMs were administrated to mice via both i.p. and i.v. injections. Analysis of the blood at 24 h showed that MAC-BMDMs were more effective in eliminating bacteria than PBS-BMDMs ($P<0.001$, FIG. 11*a*). Furthermore, MAC-BMDMs rescued 58% of the mice from immunosuppressed sepsis compared with only 10% rescued by PBS-BMDMs ($P<0.01$, FIG. 11*b*). Except for one mouse from the MAC-BMDM group displayed persistent infection, no bacteria were found in the blood in the other 6 survived mice at 480 h (FIGS. 11*f* and 11*g*). Similarly, after a repeat treatment for that mouse, all the mice showed normal levels of BW, WBC, and LYM (FIG. 11*c* to 11*e*), and showed undetectable level of MDRSA in their blood and major organs (heart, liver, spleen, lung, and kidneys).

Figure 14A:
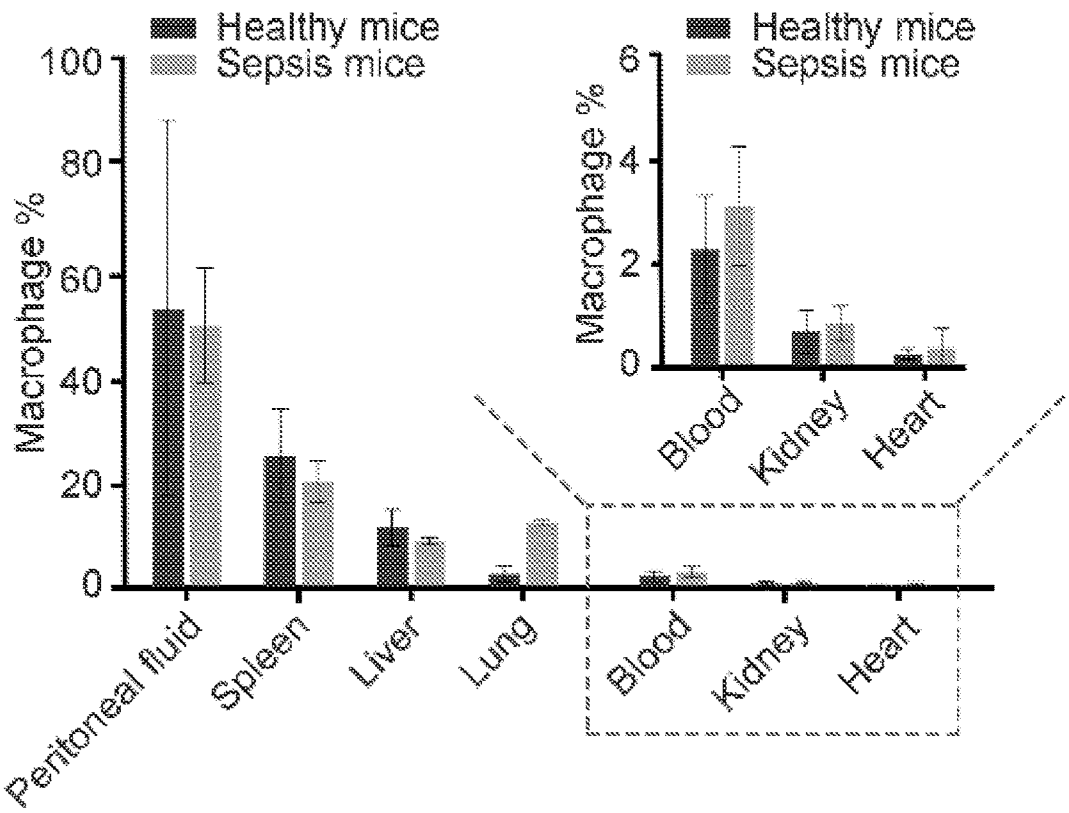
FIGS. 14A-14B. Biodistribution of BMDMs and MDRSA in mice. a, BMDMs distribution in the peritoneal fluid, blood, and major organs after 6 h of administration in healthy mice or sepsis mice. b, Bacterial distribution in the peritoneal fluid, blood, and major organs after 6 h of infection.
Figure 14B:
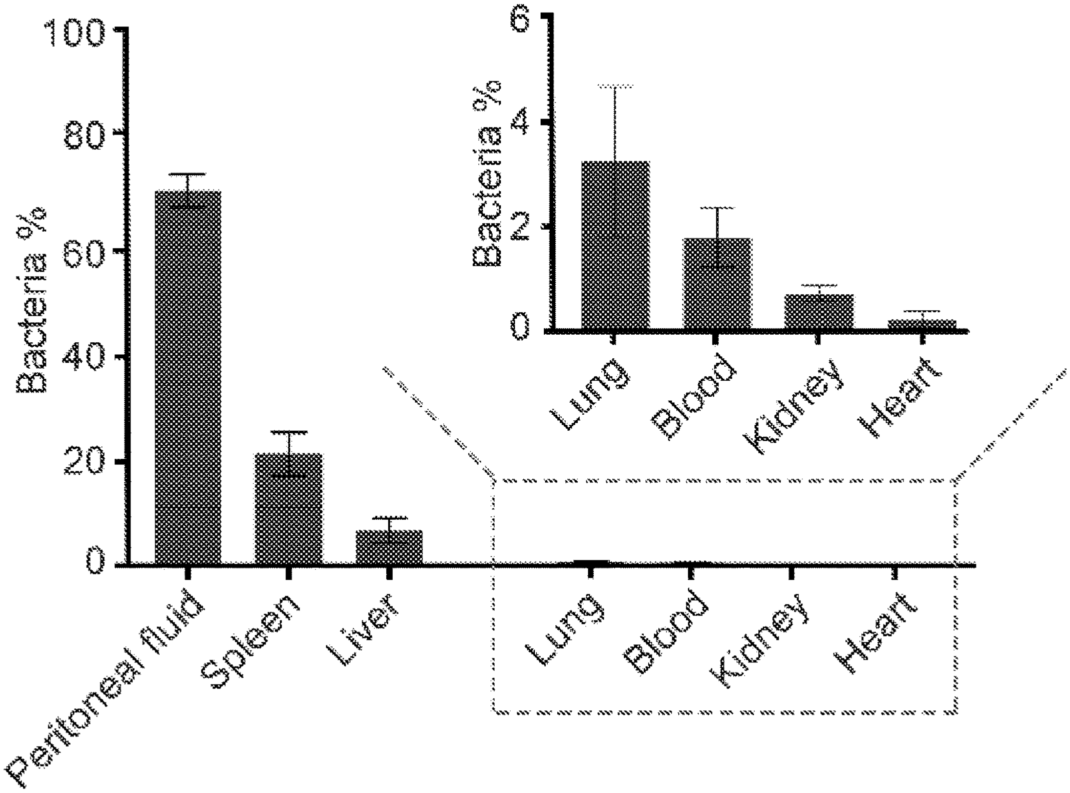
Figure 15:
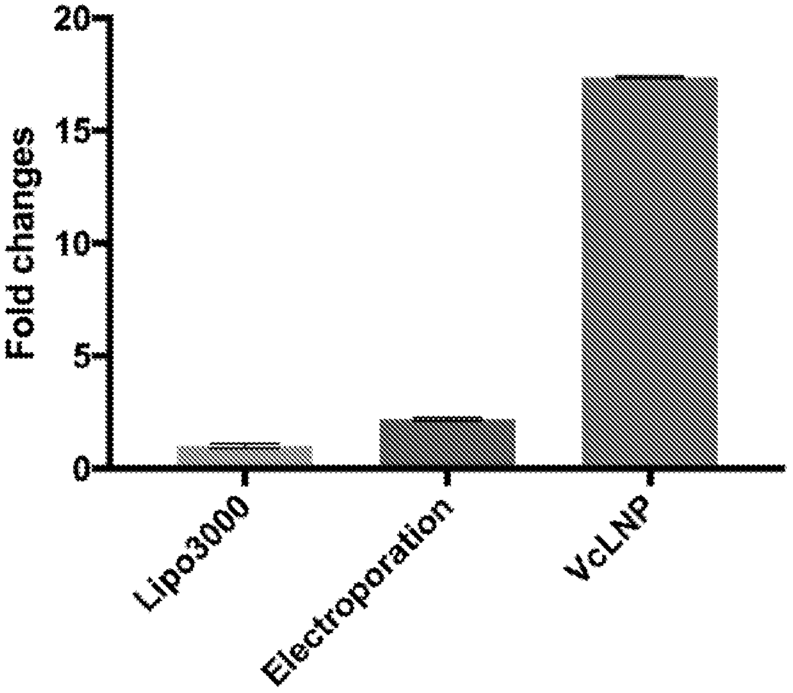
FIG. 15. VcLNPs mediated luciferase mRNA delivery in bone marrow derived dendritic cells. VcLNPs are 17-fold more effective than Lipofectamine 3000 (Lipo3000) and are 8-fold more effective than electroporation at the same mRNA concentration in bone marrow derived dendritic cells.

Bacteria are distributed into multiple organs within a few hours of infections. To profile the biodistribution of these macrophages, mRNA encoding firefly luciferase was delivered into the BMDMs (FLuc-BMDMs). Six hours post i.p.+i.v. injections of the FLuc-BMDMs, the luminescence intensity was measured in the following major organs usually infected by bacteria in this mouse model: peritoneal cavity, spleen, liver, lung, kidney, heart, and blood. The results showed a similar biodistribution in healthy and sepsis mice except that a higher luminescence intensity was detected in the lung of sepsis mice than that in healthy mice (FIG. 14*a*). In the sepsis mice, the rank order of luminescence intensity is peritoneal cavity 52.7%), spleen (21.1%), lung (12.9%), liver (9.1%), and blood (3.0%). The BMDMs biodistribution was relatively consistent to the bacterial distribution in these sepsis mice (FIG. 14*b*).

Figure 12A:
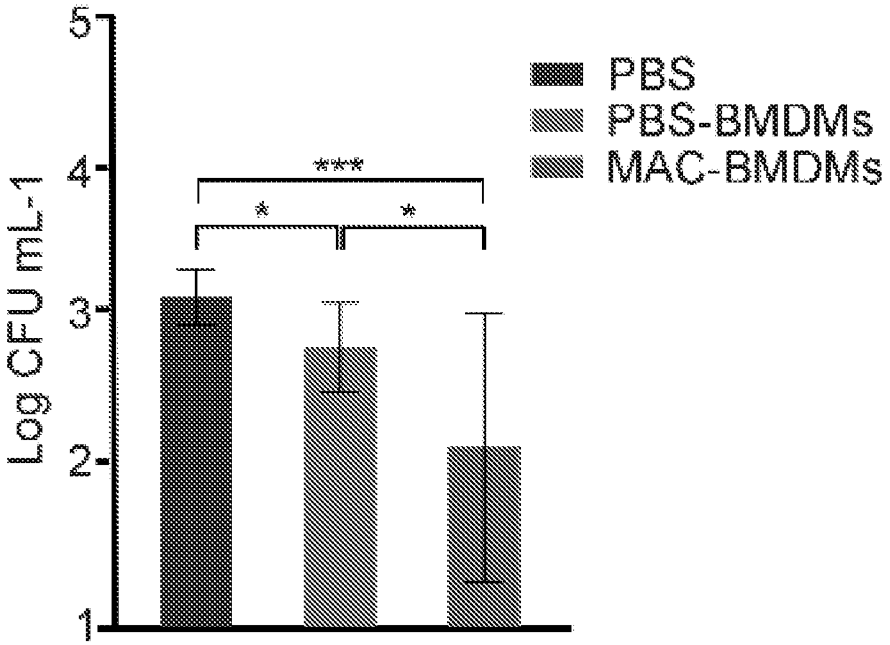
FIGS. 12A-12F. Therapeutic effects of MAC-BMDMs in mixed MDRSA bacteria (*Staphylococcus aureus* and *Escherichia coli*) induced sepsis mice with immunosuppression. a) Bacterial burden in the blood at 24 h after cell transfer. b) Percentage survival of mice with sepsis. c)-e) The BWs, WBCs, and LYMs of mice with sepsis. c) BWs; d) WBCs; e) LYMs. f) Bacterial burden in the blood of each survived mouse treated by MAC-BMDMs. The number of mice in the groups of PBS, PBS-BMDM, and MAC-BMDM were 8, 10, and 12, respectively. Data in a, c, d, and e are the mean±s.d. *P<0.05, P<0.01, *P<0.001; ns, not significant (two-tailed Student's f-test). ND, not detectable.
Figure 12B:
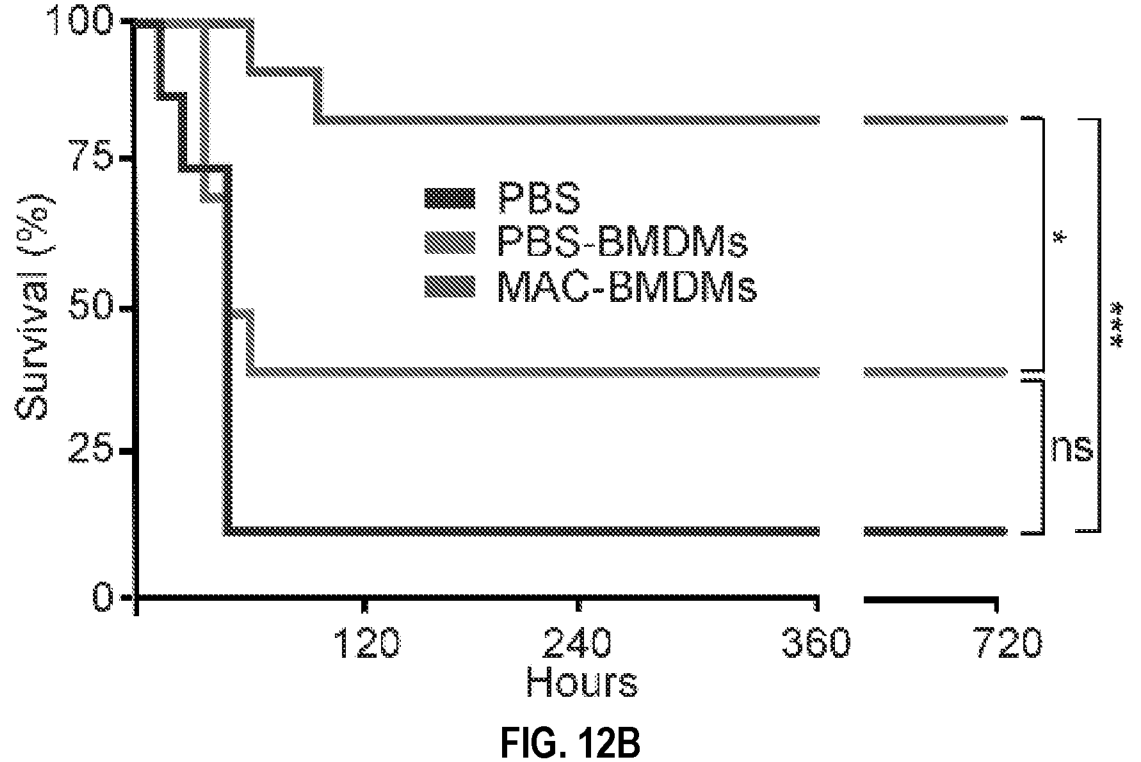
Figure 12C:
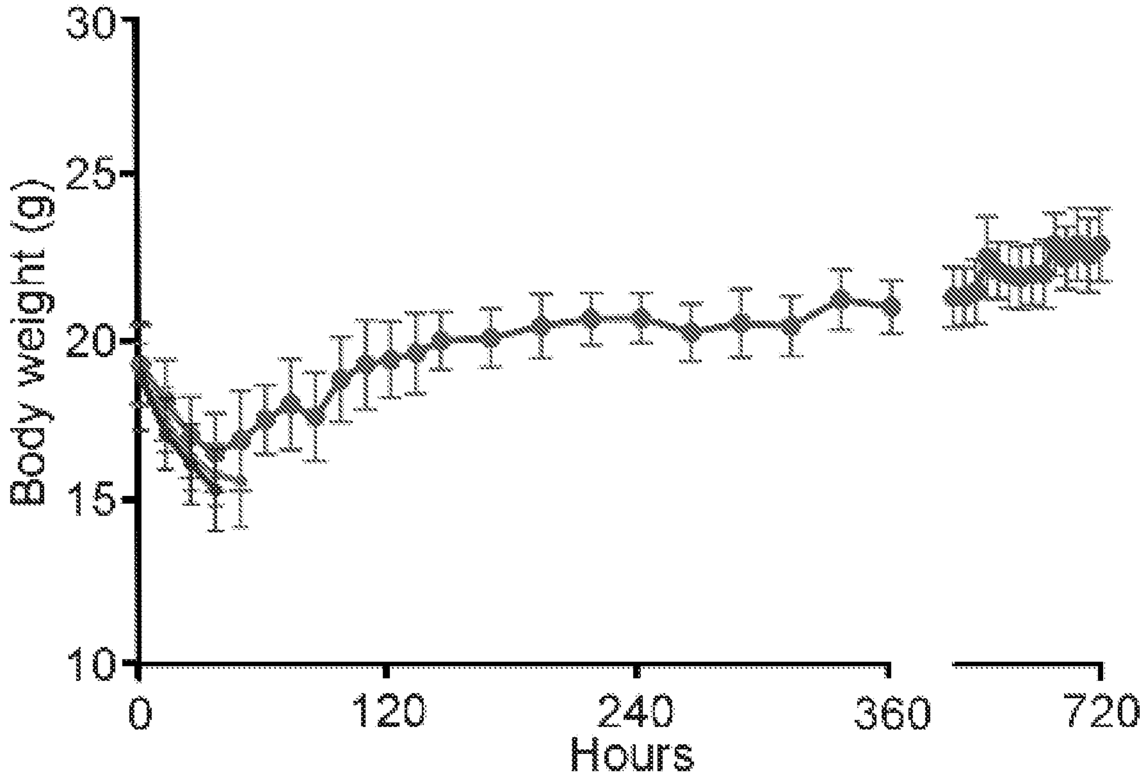
Figure 12D:
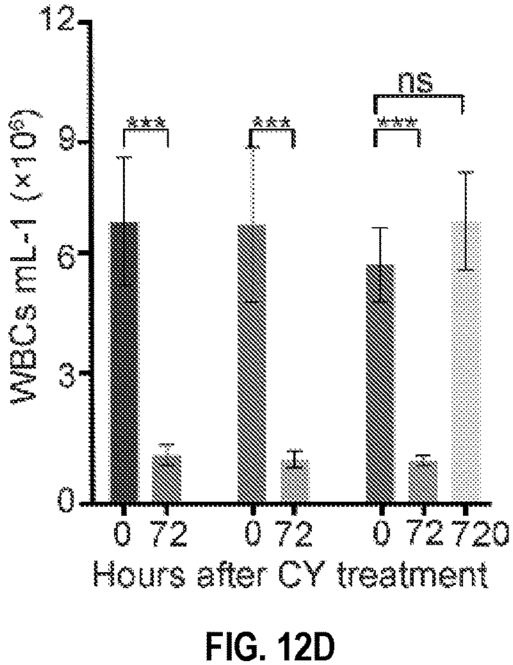
Figure 12E:
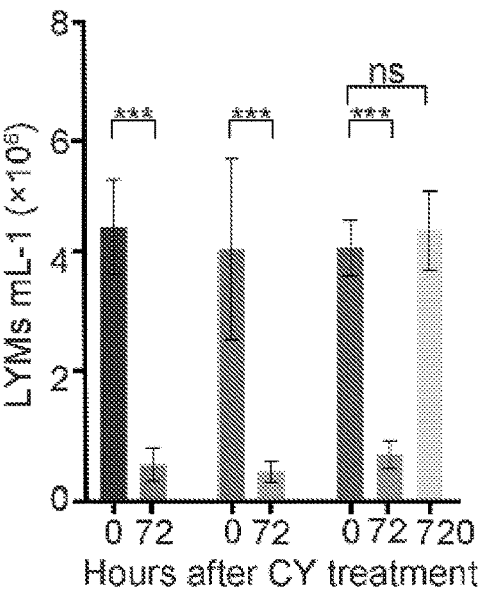
Figure 12F:
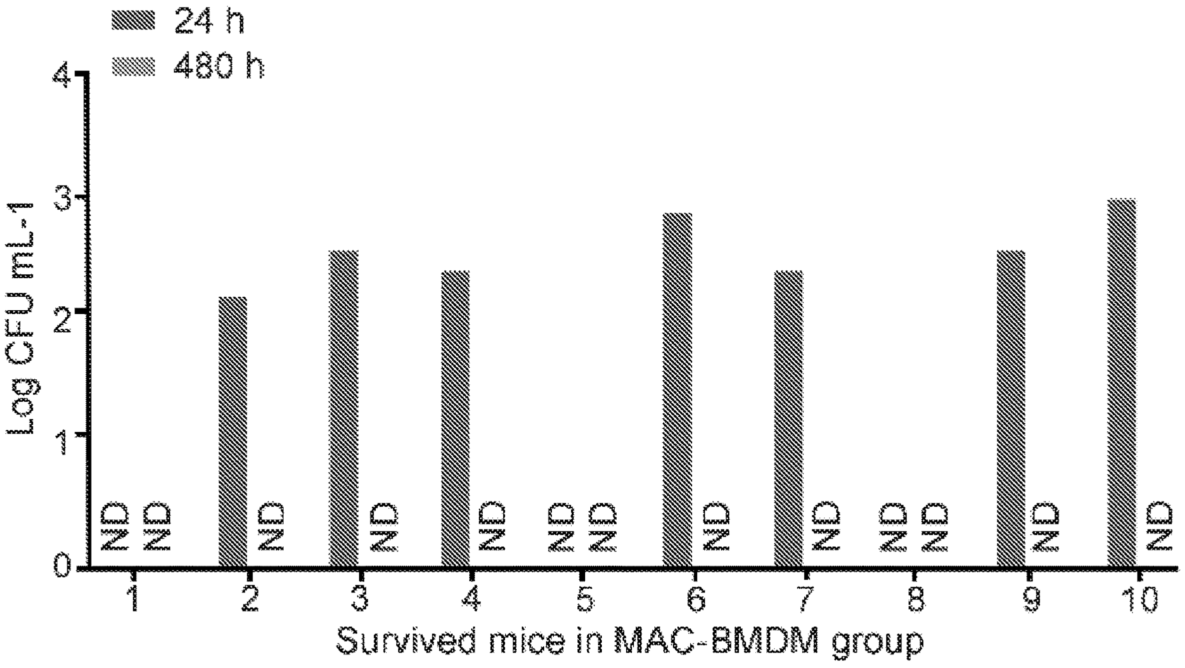

Because sepsis hosts are usually exposed to mixed bacterial infections, a formidable challenge for curing sepsis, a mouse sepsis model was established with infections by both MDRSA and MDR *E. coli*. Because the mixed infections lead to more severe symptoms compared to single bacterial infection, mice were infected with a total $2\times10^8$ CUFs of bacteria, 2.5 fold less of the bacteria dose than that in the single infection model. Treatment with MAC-BMDMs significantly reduced 43% ($P<0.01$) and 39% ($P<0.05$) bacterial burden in the blood compared to the treatment with PBS and PBS-BMDMs, respectively (FIG. 12*a*), indicating the enhanced ability of MAC-BMDMs to eliminate mixed MDR bacteria. The therapeutic efficacy of MAC-BMDMs was also reflected in the survival rate (83%) which was much higher than that of PBS group ($P<0.01$) and PBS-BMDM group ($P<0.05$) (FIG. 12*b*). In contrast, PBS-BMDMs did not significantly change the survival rate compared to the PBS. (FIG. 12*b*). Finally, normal levels of BW, WBC and LYM were observed in all the survived mice (FIG. 12*c* to 12*f*), and no persistent infections were detected in the blood and major organs (heart, liver, spleen, lung, and kidneys) at 480 h.

What is shown herein are macrophages loaded with antimicrobial peptides/cathepsin B in the lysosomes (MACs) by delivery of mRNA encapsulated in the vitamin C lipid nanoparticles (VcLNPs). The data show that adoptive transfer of MACs beneficially reduced the bacterial burden and improved survival in multidrug resistant (MDR) bacteria induced sepsis mice with immunosuppression by restoring innate immune defense, preventing bacterial immune evasion, and killing MDR bacteria. MACs were efficacious against sepsis induced by mixed strains of MDR bacteria. The superior therapeutic effects of the MACs administrated via i.p.+i.v. injections than i.p. or i.v. injection alone can be due to the infection process of sepsis. In the sepsis mice, bacteria are transported by the lymphatic system to the blood within a short period of time and then distributed to other organs via the blood circulation. The administration of i.v.+i.p. contributes to eliminating the bacteria invaded into the blood or colonized in the peritoneal cavity, leading to reduced bacterial CFUs and improved survival. When sepsis is diagnosed in an early stage, autologous macrophages can be prepared and engineered in approximately seven days. Next, these autologous MACs can be transferred back to patients with immunosuppression, which are the majority of sepsis patients under current treatment guidelines. Additionally, with the advance of induced pluripotent stem cells (iPSCs) technologies, allogeneic "universal" macrophages can be manufactured, enabling the iPSCs-derived MACs to become an off-the-shelf therapy for broad clinical applications including sepsis. Overall, adoptive transfer of MACs provides a curable strategy for patients with sepsis and MDR bacterial infection in the future.

Example 2. Methods and Materials

Chemicals and reagents. The following agents were purchased from Sigma-Aldrich, including cholesterol, gentamicin, cathepsin B (CatB) inhibitor II, cyclophosphamide (CY), and accutase cell detachment solution. The following agents were obtained from Thermo Fisher Scientific, including F4/80 monoclonal antibody, recombinant murine macrophage colony-stimulating factor (M-CSF), and LysoTracker® DND-99. 2-dioleoyl-sn-glycero-3-phosphoethanolamine (DOPE) was purchased from Avanti Polar Lipids. Bright-Glo luciferase substrate was purchased from Promega.

Cells and bacteria. The RAW264.7 cell line was obtained from the American Type Culture Collection (ATCC) and cultured in Dulbecco's modified Eagle's medium (DMEM, ATCC) with 10% fetal bovine serum (Gibco, Invitrogen). Murine bone marrow-derived macrophages (BMDMs) were obtained by adaptation of previous procedures, cultured in DMEM containing 10% fetal bovine serum and 100 ng/ml M-CSF. MDR *Staphylococcus aureus* (MDRSA, ATCC BAA-44) were grown in trypticase soy agar or broth at 37° C. with aeration. According to the data from ATCC, the MDRSA are resistant to the following antibiotic: amoxicillin/clavulanic acid, penicillin, ciprofloxacin, cephalothin, doxycycline, gentamicin, erythromycin, imipenem, methicillin, tetracycline, oxacillin, azithromycin, clindamycin, ceftriaxone, rifampin, amikacin, and tobramycin. Multidrug resistant *Escherichia coli* (MDR *E. coli*, ATCC BAA-2340) was grown in nutrient agar or nutrient broth (BD Biosciences) at 37° C. with aeration. According to the data from ATCC, the MDR *E. coli* are resistant to the following: amoxicillin/clavulanic acid, ticarcillin, piperacillin, ampicillin/sulbactam, cefalotin, cefuroxime, cefotetan, cefpodoxime, cefotaxime, ceftizoxime, cefazolin, cefoxitin, ceftazidime, ceftriaxone, cefepime, doripenem, meropenem, ertapenem, imipenem, nalidixic acid, moxifloxacin, norfloxacin, ciprofloxacin, levofloxacin, tobramycin, aztreonam, and trimethoprim/sulfamethoxazole.

Synthesis of vitamin-derived lipids. Compound 1, vitamin B3 derivative, vitamin C derivative, and vitamin H (also called vitamin B7) derivative, were synthesized according to the methods reported previously.

Preparation and characterization of VLNP. mRNAs used herein were constructed by the mRNA platform based on the reported method. The preparation of mRNA LNPs was reported previously. Briefly, newly synthesized vitamin-derived lipids were formulated with DOPE, Cholesterol as well as firefly luciferase (FLuc) mRNA by pipetting for in vitro screenings or by a microfluidic mixing device for ex vivo studies. The NanoZS Zetasizer (Malvern) was used to measure the size and zeta potential. The entrapment efficiency was measured by the Ribogreen assay. The morphology of VcLNPs was examined on Thermo Scientific™ Glacios™ CryoTEM using the methods described before. In order to effectively deliver mRNA into macrophages, an initial screening was performed using the five vitamin-lipid nanoparticles (VLNPs), Lipofectamine 3000, and electroporation. Newly synthesized vitamin-derived lipids were formulated with DOPE, Cholesterol (Lipid:DOPE:Cholesterol=20:30:40, mole ratio) as well as FLuc mRNA (Lipid:mRNA=10:1, mass ratio) in the initial screening. Delivery efficiency of mRNA was determined by the luciferase expression assay. Next, the dynamics of FLuc expression followed by two rounds of characterization were carried out after the initial screening. Briefly, VcLNPs from A-1 to A-16 were prepared based on the orthogonal array design table $L_{16}(4)^4$ and the top formulation was predicted by the FLuc expression data. After the top formulation was validated, the second round of characterization focused on fine tuning the mass ratio of Vc-Lipid:mRNA. Electroporation for macrophages was performed using Nucleofector kit (Lonza) and the suggested protocols by the Nucleofector 2b Device.

Cellular uptake and endosomal escape. RAW264.7 cells were seeded in a 6-well plate at $10^5$ cells/well and cultured for 24 h. Then, cells were treated by FLuc mRNA and Alexa-Fluor 647-labeled RNA (1:1, weight ratio) using Lipofectamine 3000, VcLNPs, or electroporation. After 3 h incubation, cellular uptake was quantified by a flow cytometer (LSRII, BD). To study endocytosis pathways of VcLNPs, cellular uptake assay was performed in the presence of different endocytotic inhibitors, including 5-(N-methyl-N-isopropyl)amiloride (EIPA), methyl-beta-cyclodextrin (MPCD), and chlorpromazine hydrochloride (CPZ). For the endosomal escape assay, $2\times10^4$ cells were plated in an imaging dish (ibidi) for 24 h, and then 150 μg/mL of calcein was added to the cells with or without VcLNPs containing Alexa-Fluor 647-labeled RNA for 6 h at 37° C. After washing with PBS to remove extracellular calcein and nanoparticles, cells were lively imaged under the Nikon A1R Live Cell Imaging Confocal Microscope via the 487 nm and 647 nm lasers.

Analysis of lysosome co-localization. To test whether AMP-CatB can specifically accumulate in the lysosomes, the eGFP-CatB mRNA were prepared and delivered into the RAW264.7 cells using VcLNPs. Then, lysosomes were stained with LysoTracker® Red DND-99, a well-established lysosome probe. The co-localization of eGFP-CatB and LysoTracker® Red DND-99 was analyzed under the Nikon A1R Live Cell Imaging Confocal Microscope via the 487 nm and 561 nm lasers.

Cytotoxicity of vitamin C lipid nanoparticles in BMDMs. Cytotoxicity of VcLNPs in BMDMs was examined by an MTT assay. $2\times10^4$ BMDMs were seeded into each well of 96-well plates in 100 μL of growth medium. After 12 h of incubation with PBS, free AMP-CatB mRNA, empty VcLNPs, AMP-CatB mRNA VcLNPs/CatB inhibitor II, and AMP-CatB mRNA VcLNPs, MTT solution was added. After additional 4 h incubation, 100 uL of 10% SDS-HCl was added into each well. The purple formazan was dissolved overnight and the absorbance was measured at 570 nm by a plate reader.

In vitro antimicrobial assay. The intracellular antimicrobial assay was conducted according to the reported method. Briefly, after treated by PBS, free AMP-CatB mRNA, empty VcLNPs, AMP-CatB mRNA VcLNPs/CatB inhibitor II, and AMP-CatB mRNA VcLNPs, the RAW264.7 cells or BMDMs were incubated with MDRSA or MDR *E. coli* at multiplicity of infection (MOI) of 25 for 120 min. After washing by PBS, medium containing gentamicin (100 ρg/mL) was supplemented and the cells were incubated for additional 1 h to clear extracellular bacteria. At different time points, cells were washed by PBS and lysed with 0.1% Triton-X 100. Lastly, the lysates were cultured on the nutrient agar or trypticase soy agar for counting bacterial colony forming units (CFUs).

In vivo treatment of MDR induced sepsis mice with immunosuppression. All mouse experiments were performed under the protocols approved by the Institutional Animal Care and Use Committee (IACUC) of the Ohio State University. C57BL/6 mice (6-7 weeks) were purchased from the Jackson Lab. The immunosuppressed model of sepsis was conducted as the method in the literature. Briefly, C57BL/6 mice were intraperitoneally injected cyclophosphamide (CY) at a dosage of 100 mg/kg for 3 consecutive days before bacterial infection. Their immunocompromised states were assessed by monitoring the body weights (BWs), counting white blood cells (WBCs) by a hemocytometer, and counting lymphocytes (LYMs) by the Kwik-Diff stain. Mice were then intraperitoneally inoculated with 0.1 ml of bacterial suspension ($5\times10^8$ CFUs/mouse for MDRSA infections and $2\times10^8$ CFUs/mouse for mixed MDRSA and MDR *E. coli* infections). Afterwards, the mice were administrated by 0.2 mL PBS or 0.2 mL cell suspension (total 2 million cells/mouse). After 24 h infection, the blood was collected from the facial vein to quantify bacterial CFUs. The survival of mice was assessed every 12 h within the first 6 days and then every 24 h for the following 24 days based on 20% loss of BW and the early removal criteria. After 30 days, blood was collected from all survived mice and the number of WBC and LYM were counted. After that, the mice were euthanized and major organs (heart, liver, spleen, lung, and kidneys) were aseptically homogenized to quantify the bacterial CFUs.

Biodistribution of macrophages and bacteria. The biodistribution of macrophages was performed on both healthy and sepsis C57BL/6 mice (6-7 weeks). In this experiment, mRNA encoding firefly luciferase was first delivered into the BMDMs (FLuc-BMDMs) for 12 h. Next, each mouse was administrated 0.2 mL PBS or 0.2 mL cell suspension (total 4 million cells) via the intraperitoneal (i.p.)+intravenous (i.v.) injection. After 6 h, mice were i.p. injected with 150 L of the D-luciferin substrate (30 mg/mL) and then euthanized by $CO_2$ after 8 min of injection. Bioluminescence signals in the blood, peritoneal fluid, and major organs were immediately measured using a Xenogen IVIS imaging system (Caliper, Alameda, CA). The bacterial CFUs in the blood, peritoneal fluid, and major organs of sepsis mice were quantified after 6 h of infection.

REFERENCES

1. Reinhart, K., et al. Recognizing sepsis as a global health priority—a WHO resolution. New England Journal of Medicine 377, 414-417 (2017).
2. van der Poll, T. Immunotherapy of sepsis. The Lancet infectious diseases 1, 165-174 (2001).
3. Huttunen, R. & Aittoniemi, J. New concepts in the pathogenesis, diagnosis and treatment of bacteremia and sepsis. Journal of Infection 63, 407-419 (2011).
4. Hotchkiss, R. S. & Karl, I. E. The pathophysiology and treatment of sepsis. New England Journal of Medicine 348, 138-150 (2003).
5. Otto, G. P., et al. The late phase of sepsis is characterized by an increased microbiological burden and death rate. Critical care 15, R183 (2011).
6. Hotchkiss, R. S., Monneret, G. & Payen, D. Immunosuppression in sepsis: a novel understanding of the disorder and a new therapeutic approach. The Lancet infectious diseases 13, 260-268 (2013).
7. Czermak, B. J., et al. Protective effects of C5a blockade in sepsis. Nature medicine 5, 788 (1999).
8. Ward, P. A. & Fattahi, F. New strategies for treatment of infectious sepsis. Journal of leukocyte biology (2019).
9. Huang, X., et al. PD-1 expression by macrophages plays a pathologic role in altering microbial clearance and the innate inflammatory response to sepsis. Proceedings of the National Academy of Sciences of the United States of America 106, 6303-6308 (2009).
10. Docke, W. D., et al. Monocyte deactivation in septic patients: restoration by IFN-gamma treatment. Nature medicine 3, 678-681 (1997).
11. Presneill, J. J., Harris, T., Stewart, A. G., Cade, J. F. & Wilson, J. W. A randomized phase II trial of granulocyte-macrophage colony-stimulating factor therapy in severe sepsis with respiratory dysfunction. American journal of respiratory and critical care medicine 166, 138-143 (2002).
12. Galbraith, N., Walker, S., Galandiuk, S., Gardner, S. & Polk, H. C., Jr. The Significance and Challenges of Monocyte Impairment: For the Ill Patient and the Surgeon. Surgical infections 17, 303-312 (2016).

13. Cavaillon, J. M., Eisen, D. & Annane, D. Is boosting the immune system in sepsis appropriate? Critical care (London, England) 18, 216 (2014).
14. Foster, T. J. Immune evasion by staphylococci. Nature reviews. Microbiology 3, 948-958 (2005).
15. Garzoni, C. & Kelley, W. L. *Staphylococcus aureus*: new evidence for intracellular persistence. Trends in microbiology 17, 59-65 (2009).
16. Lewis, A. J., Richards, A. C. & Mulvey, M. A. Invasion of Host Cells and Tissues by Uropathogenic Bacteria. Microbiology spectrum 4(2016).
17. Pauwels, A. M., Trost, M., Beyaert, R. & Hoffmann, E. Patterns, Receptors, and Signals: Regulation of Phagosome Maturation. Trends in immunology 38, 407-422 (2017).
18. June, C. H. & Sadelain, M. Chimeric Antigen Receptor Therapy. The New England journal of medicine 379, 64-73 (2018).
19. Csoka, B., et al. Macrophage P2X4 receptors augment bacterial killing and protect against sepsis. JCI insight 3(2018).
20. Saleh, M., et al. Enhanced bacterial clearance and sepsis resistance in caspase-12-deficient mice. Nature 440, 1064-1068 (2006).
21. Giles, F. J., Redman, R., Yazji, S. & Bellm, L. Iseganan HCl: a novel antimicrobial agent. Expert opinion on investigational drugs 11, 1161-1170 (2002).
22. Linke, M., Herzog, V. & Brix, K. Trafficking of lysosomal cathepsin B-green fluorescent protein to the surface of thyroid epithelial cells involves the endosomal/lysosomal compartment. Journal of cell science 115, 4877-4889 (2002).
23. Vasey, P. A., et al. Phase I clinical and pharmacokinetic study of PK1 [N-(2-hydroxypropyl)methacrylamide copolymer doxorubicin]: first member of a new class of chemotherapeutic agents-drug-polymer conjugates. Cancer Research Campaign Phase I/II Committee. Clinical cancer research: an official journal of the American Association for Cancer Research 5, 83-94 (1999).
24. Mora, J. R., Iwata, M. & von Andrian, U. H. Vitamin effects on the immune system: vitamins A and D take centre stage. Nature reviews. Immunology 8, 685-698 (2008).
25. Zhang, C., et al. Chemotherapy drugs derived nanoparticles encapsulating mRNA encoding tumor suppressor proteins to treat triple-negative breast cancer. Nano Research, 1-7.
26. Li, B., et al. An orthogonal array optimization of lipid-like nanoparticles for mRNA delivery in vivo. Nano letters 15, 8099-8107 (2015).
27. Su, X., Fricke, J., Kavanagh, D. G. & Irvine, D. J. In vitro and in vivo mRNA delivery using lipid-enveloped pH-responsive polymer nanoparticles. Molecular pharmaceutics 8, 774-787 (2011).
28. McConnell, R. M., York, J. L., Frizzell, D. & Ezell, C. Inhibition studies of some serine and thiol proteinases by new leupeptin analogs. Journal of medicinal chemistry 36, 1084-1089 (1993).
29. Zhang, L., et al. High-throughput synergy screening identifies microbial metabolites as combination agents for the treatment of fungal infections. Proceedings of the National Academy of Sciences of the United States of America 104, 4606-4611 (2007).
30. Ying, W., Cheruku, P. S., Bazer, F. W., Safe, S. H. & Zhou, B. Investigation of macrophage polarization using bone marrow derived macrophages. JoVE (Journal of Visualized Experiments), e50323 (2013).
31. Frimodt-Møller, N., Knudsen, J. & Espersen, F. The mouse peritonitis/sepsis model. in Handbook of animal models of infection 127-136 (Elsevier, 1999).
32. McVicker, G., et al. Clonal expansion during *Staphylococcus aureus* infection dynamics reveals the effect of antibiotic intervention. PLoS pathogens 10, e1003959 (2014).
33. Crow, D. Could iPSCs Enable "Off-the-Shelf" Cell Therapy? Cell 177, 1667-1669 (2019).

```
SEQUENCES
            SEQ ID NO: 1, amino acid sequence of an
                               antimicrobial peptide
RGGLCYCRGRFCVGR

             SEQ ID NO: 2, nucleotide sequence that
                  encodes an antimicropbial peptide
AGGGGCGGCUUGUGCUACUGUCGCGGAAGGUUUUGUGUAGGCAGA

   SEQ ID NO: 3, amino acid sequence of cathepsin B
MWWSLILLSCLLALTSAHDKPSFHPLSDDLINYINKQNTTWQAGRNFYNV

DISYLKKLCGTVLGGPKLPGRVAFGEDIDLPETFDAREQWSNCPTIGQIR

DQGSCGSCWAFGAVEAISDRTCIHTNGRVNVEVSAEDLLTCCGIQCGDGC

NGGYPSGAWSFWTKKGLVSGGVYNSHVGCLPYTIPPCEHHVNGSRPPCTG

EGDTPRCNKSCEAGYSPSYKEDKHFGYTSYSVSNSVKEIMAEIYKNGPVE

GAFTVFSDFLTYKSGVYKHEAGDMMGGHAIRILGWGVENGVPYWLAANSW

NLDWGDNGFFKILRGENHCGIESEIVAGIPRTDQYWGR

              SEQ ID NO: 4, nucleotide sequence that
                                 encodes cathepsin B
AUGUGGUGGUCCUUGAUCCUUCUUUCUUGCCUGCUGGCACUGACCAGUGC

CCAUGACAAGCCUUCCUUCCACCCGCUGUCGGAUGACCUGAUUAACUAUA

UCAACAAACAGAAUACAACAUGGCAGGCUGGACGCAACUUCUACAAUGUU

GACAUAAGCUAUCUGAAGAAGCUGUGUGGCACUGUCCUGGGUGGACCCAA

ACUGCCAGGAAGGGUUGCGUUCGGUGAGGACAUAGAUCUACCUGAAACCU

UUGAUGCACGGGAACAAUGGUCCAACUGCCCGACCAUUGGACAGAUUAGA

GACCAGGGCUCCUGCGGCUCUUGUUGGGCAUUUGGGGCAGUGGAAGCCAU

UUCUGACCGAACCUGCAUUCACACCAAUGGCCGAGUCAACGUGGAGGUGU

CUGCUGAAGACCUGCUUACUUGCUGUGGUAUCCAGUGUGGGGACGGCUGU

AAUGGUGGCUAUCCCUCUGGAGCAUGGAGCUUCUGGACAAAAAAAGGCCU

GGUUUCAGGUGGAGUCUACAAUUCUCAUGUAGGCUGCUUACCAUACACCA

UCCCUCCCUGCGAGCACCAUGUCAAUGGCUCCCGUCCCCCAUGCACUGGA

GAAGGAGAUACUCCCAGGUGCAACAAGAGCUGUGAAGCUGGCUACUCCCC

AUCCUACAAAGAGGAUAAGCACUUUGGGUACACUUCCUACAGCGUGUCUA

ACAGUGUGAAGGAGAUCAUGGCAGAAAUCUACAAAAAUGGCCCAGUGGAG

GGUGCCUUCACUGUGUUUUCUGACUUCUUGACUUACAAAUCAGGAGUAUA

CAAGCAUGAAGCCGGUGAUAUGAUGGGUGGCCACGCCAUCCGCAUCCUGG

GCUGGGGAGUAGAGAAUGGAGUUCCCUACUGGCUGGCAGCCAACUCUUGG
```

-continued

AACCUUGACUGGGGUGAUAAUGGCUUCUUUAAAAUCCUCAGAGGAGAAAA

CCACUGUGGCAUUGAAUCAGAAAUUGUGGCUGGAAUCCCACGCACUGACC

AGUACUGGGGAAGA

SEQ ID NO: 5, amino acid sequence of a linker
FGFLG

SEQ ID NO: 6, nucleotide sequence that encodes a linker
UUCGGAUUUCUGGGC

SEQ ID NO: 7
MWWSLILLSCLLALTSAHDKPSFHPLSDDLINYINKQNTTWQAGRNFYNV

DISYLKKLCGTVLGGPKLPGRVAFGEDIDLPETFDAREQWSNCPTIGQIR

DQGSCGSCWAFGAVEAISDRTCIHTNGRVNVEVSAEDLLTCCGIQCGDGC

NGGYPSGAWSFWTKKGLVSGGVYNSHVGCLPYTIPPCEHHVNGSRPPCTG

EGDTPRCNKSCEAGYSPSYKEDKHFGYTSYSVSNSVKEIMAEIYKNGPVE

GAFTVFSDFLTYKSGVYKHEAGDMMGGHAIRILGWGVENGVPYWLAANSW

NLDWGDNGFFKILRGENHCGIESEIVAGIPRTDQYWGRFGFLGRGGLCYC

RGRFCVGR

SEQ ID NO: 8
AUGUGGUGGUCCUUGAUCCUUCUUUCUUGCCUGCUGGCACUGACCAGUGC

CCAUGACAAGCCUUCCUUCCACCCGCUGUCGGAUGACCUGAUUAACUAUA

UCAACAAACAGAAUACAACAUGGCAGGCUGGACGCAACUUCUACAAUGUU

GACAUAAGCUAUCUGAAGAAGCUGUGUGGCACUGUCCUGGGUGGACCCAA

ACUGCCAGGAAGGGUUGCGUUCGGUGAGGACAUAGAUCUACCUGAAACCU

UUGAUGCACGGGAACAAUGGUCCAACUGCCCGACCAUUGGACAGAUUAGA

GACCAGGGCUCCUGCGGCUCUUGUUGGGCAUUUGGGGCAGUGGAAGCCAU

UUCUGACCGAACCUGCAUUCACACCAAUGGCCGAGUCAACGUGGAGGUGU

CUGCUGAAGACCUGCUUACUUGCUGUGGUAUCCAGUGUGGGGACGGCUGU

AAUGGUGGCUAUCCCUCUGGAGCAUGGAGCUUCUGGACAAAAAAAGGCCU

GGUUUCAGGUGGAGUCUACAAUUCUCAUGUAGGCUGCUUACCAUACACCA

-continued

UCCCUCCCUGCGAGCACCAUGUCAAUGGCUCCCGUCCCCCAUGCACUGGA

GAAGGAGAUACUCCCAGGUGCAACAAGAGCUGUGAAGCUGGCUACUCCCC

AUCCUACAAAGAGGAUAAGCACUUUGGGUACACUUCCUACAGCGUGUCUA

ACAGUGUGAAGGAGAUCAUGGCAGAAAUCUACAAAAAUGGCCCAGUGGAG

GGUGCCUUCACUGUGUUUUCUGACUUCUUGACUUACAAAUCAGGAGUAUA

CAAGCAUGAAGCCGGUGAUAUGAUGGGUGGCCACGCCAUCCGCAUCCUGG

GCUGGGGAGUAGAGAAUGGAGUUCCCUACUGGCUGGCAGCCAACUCUUGG

AACCUUGACUGGGGUGAUAAUGGCUUCUUUAAAAUCCUCAGAGGAGAAAA

CCACUGUGGCAUUGAAUCAGAAAUUGUGGCUGGAAUCCCACGCACUGACC

AGUACUGGGGAAGAUUCGGAUUUCUGGGCAGGGGCGGCUUGUGCUACUGU

CGCGGAAGGUUUUGUGUAGGCAGA amino acid sequence of a linker
SEQ ID NO: 9
Gly Phe Leu Gly amino acid sequence of a linker
SEQ ID NO: 10
Ala Leu Ala Leu;

amino acid sequence of a linker
SEQ ID NO: 11
Ala Gly Val Phe amino acid sequence of a linker
SEQ ID NO: 12
Val Lys Lys Arg Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

We claim:

1. An antigen presenting cell, comprising:

a lipid-based nanoparticle, comprising:

a recombinant polynucleotide, comprising:

a first nucleic acid encoding an antimicrobial peptide;

a second nucleic acid encoding cathepsin B; and a third nucleic acid encoding a linker; and a vitamin-lipid, wherein the vitamin-lipid comprises a vitamin moiety, and wherein the vitamin moiety comprises vitamin C.

2. The antigen presenting cell of claim 1, wherein the first nucleic acid and the second nucleic acid are linked by the third nucleic acid.

3. The antigen presenting cell of claim 1, wherein the recombinant polynucleotide is encapsulated by the vitamin-lipid.

4. The antigen presenting cell of claim 1, wherein the recombinant polynucleotide comprises an RNA or a DNA.

5. The antigen presenting cell of claim 1, wherein the antimicrobial peptide comprises the sequence SEQ ID NO: 1.

6. The antigen presenting cell of claim 1, wherein the first nucleic acid comprises the sequence SEQ ID NO: 2.

7. The antigen presenting cell of claim 1, wherein the second nucleic acid comprises the sequence SEQ ID NO: 4.

8. The antigen presenting cell of claim 1, wherein the linker comprises a cathepsin B sensitive linker.

9. The antigen presenting cell of claim 1, wherein the third nucleic acid comprises the sequence SEQ ID NO: 6.

10. The antigen presenting cell of claim 1, wherein the recombinant polynucleotide comprises the sequence SEQ ID NO: 8.

11. The antigen presenting cell of claim 1, wherein the vitamin-lipid comprises a compound of Formula A:

Formula A

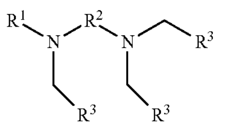

or a salt thereof, wherein:

$R^1$ is an alkyl or ether linker, wherein the alkyl or ether linker is substituted with a vitamin moiety;

$R^2$ is alkyl, cycloalkyl, heterocycloalkyl, alkylheterocycloalkyl, amide, alkylamide, ether, alkylether.

12. The antigen presenting cell of claim 1, wherein the antigen presenting cell comprises a macrophage or a dendritic cell.

13. The antigen presenting cell of claim 12, wherein the macrophage comprises a bone marrow-derived macrophage or a monocyte-derived macrophage.

14. The antigen presenting cell of claim 12, wherein the dendritic cell comprises a bone marrow-derived dendritic cell, a monocyte-derived dendritic cell, a conventional dendritic cell-1, or a conventional dendritic cell-2.

15. An antigen presenting cell, comprising:

a lipid-based nanoparticle, comprising:

a recombinant polynucleotide, comprising:

a first nucleic acid encoding an antimicrobial peptide;

a second nucleic acid encoding cathepsin B; and a third nucleic acid encoding a linker; and a vitamin-lipid, wherein the vitamin-lipid is selected from the group consisting of:

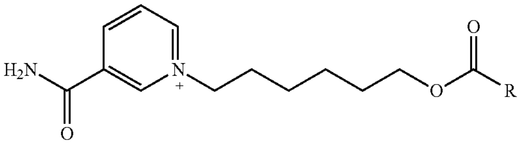

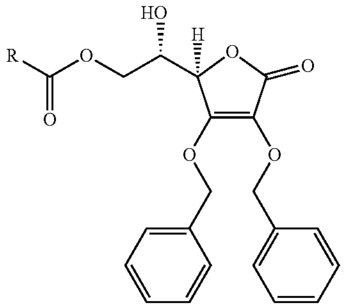

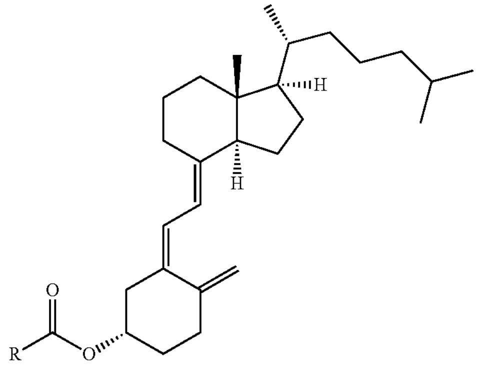

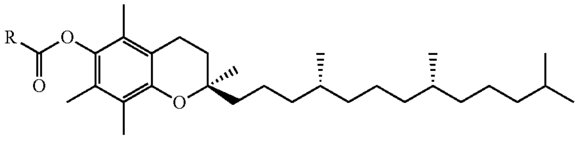

-continued

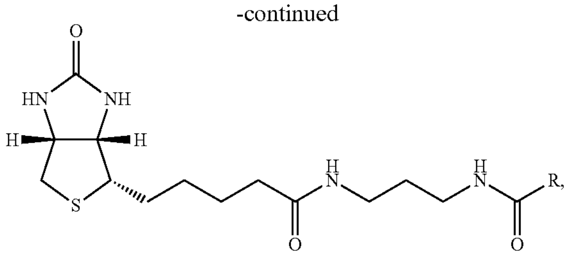

wherein R is

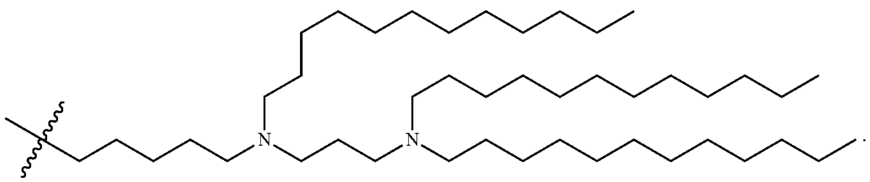 [SMILES: *CCCCCN(CCCCCCCCCCCC)CCCN(CCCCCCCCCCCC)CCCCCCCCCCCC]

16. A method of treating sepsis, comprising administering to a subject one or more antigen presenting cells comprising:

a nanoparticle, comprising:

a recombinant polynucleotide, comprising:

a first nucleic acid encoding an antimicrobial peptide, a second nucleic acid encoding cathepsin B, and a third nucleic acid encoding a linker; and a vitamin-lipid, wherein the vitamin-lipid comprises a vitamin moiety, and wherein the vitamin moiety comprises vitamin C.

17. The method of claim 16, wherein the antigen presenting cell is derived from the subject.

18. The method of claim 16, wherein the subject comprises a human.

* * * * *

SEQUENCE LISTING

```
<160> NUMBER OF SEQ ID NOS: 12

<210> SEQ ID NO 1
<211> LENGTH: 15
<212> TYPE: PRT
<213> ORGANISM: Artificial Sequence
<220> FEATURE:
<223> OTHER INFORMATION: Synthetic Construct

<400> SEQUENCE: 1

Arg Gly Gly Leu Cys Tyr Cys Arg Gly Arg Phe Cys Val Gly Arg
1               5                   10                  15


<210> SEQ ID NO 2
<211> LENGTH: 45
<212> TYPE: RNA
<213> ORGANISM: Artificial Sequence
<220> FEATURE:
<223> OTHER INFORMATION: Synthetic Construct
```

<400> SEQUENCE: 2
aggggcggcu ugugcuacug ucgcggaagg uuuuguguag gcaga 45

<210> SEQ ID NO 3
<211> LENGTH: 338
<212> TYPE: PRT
<213> ORGANISM: Artificial Sequence
<220> FEATURE:
<223> OTHER INFORMATION: Synthetic Construct

<400> SEQUENCE: 3

Met Trp Trp Ser Leu Ile Leu Leu Ser Cys Leu Leu Ala Leu Thr Ser
1 5 10 15

Ala His Asp Lys Pro Ser Phe His Pro Leu Ser Asp Asp Leu Ile Asn
20 25 30

Tyr Ile Asn Lys Gln Asn Thr Thr Trp Gln Ala Gly Arg Asn Phe Tyr
35 40 45

Asn Val Asp Ile Ser Tyr Leu Lys Lys Leu Cys Gly Thr Val Leu Gly
50 55 60

Gly Pro Lys Leu Pro Gly Arg Val Ala Phe Gly Glu Asp Ile Asp Leu
65 70 75 80

Pro Glu Thr Phe Asp Ala Arg Glu Gln Trp Ser Asn Cys Pro Thr Ile
85 90 95

Gly Gln Ile Arg Asp Gln Gly Ser Cys Gly Ser Cys Trp Ala Phe Gly
100 105 110

Ala Val Glu Ala Ile Ser Asp Arg Thr Cys Ile His Thr Asn Gly Arg
115 120 125

Val Asn Val Glu Val Ser Ala Glu Asp Leu Leu Thr Cys Cys Gly Ile
130 135 140

Gln Cys Gly Asp Gly Cys Asn Gly Gly Tyr Pro Ser Gly Ala Trp Ser
145 150 155 160

Phe Trp Thr Lys Lys Gly Leu Val Ser Gly Gly Val Tyr Asn Ser His
165 170 175

Val Gly Cys Leu Pro Tyr Thr Ile Pro Pro Cys Glu His His Val Asn
180 185 190

Gly Ser Arg Pro Pro Cys Thr Gly Glu Gly Asp Thr Pro Arg Cys Asn
195 200 205

Lys Ser Cys Glu Ala Gly Tyr Ser Pro Ser Tyr Lys Glu Asp Lys His
210 215 220

Phe Gly Tyr Thr Ser Tyr Ser Val Ser Asn Ser Val Lys Glu Ile Met
225 230 235 240

Ala Glu Ile Tyr Lys Asn Gly Pro Val Glu Gly Ala Phe Thr Val Phe
245 250 255

Ser Asp Phe Leu Thr Tyr Lys Ser Gly Val Tyr Lys His Glu Ala Gly
260 265 270

Asp Met Met Gly Gly His Ala Ile Arg Ile Leu Gly Trp Gly Val Glu
275 280 285

Asn Gly Val Pro Tyr Trp Leu Ala Ala Asn Ser Trp Asn Leu Asp Trp
290 295 300

Gly Asp Asn Gly Phe Phe Lys Ile Leu Arg Gly Glu Asn His Cys Gly
305 310 315 320

Ile Glu Ser Glu Ile Val Ala Gly Ile Pro Arg Thr Asp Gln Tyr Trp
325 330 335

Gly Arg

<210> SEQ ID NO 4
<211> LENGTH: 1014
<212> TYPE: RNA
<213> ORGANISM: Artificial Sequence
<220> FEATURE:
<223> OTHER INFORMATION: Synthetic Construct

<400> SEQUENCE: 4 auguggugu ccuugauccu ucuuucuugc cugcuggcac ugaccagugc ccaugacaag 60
ccuuccuucc acccgcuguc ggaugaccug auuaacuaua ucaacaaaca gaauacaaca 120
uggcaggcug gacgcaacuu cuacaauguu gacauaagcu aucugaagaa gcuguguggc 180
acuguccugg guggacccaa acugccagga aggguugcgu ucggugagga cauagaucua 240
ccugaaaccu uugaugcacg ggaacaaugg uccaacugcc cgaccauugg acagauuaga 300
gaccagggcu ccugcggcuc uuguugggca uuuggggcag uggaagccau uucugaccga 360
accugcauuc acaccaaugg ccgagucaac guggaggugu cugcugaaga ccugcuuacu 420
ugcuguggua uccagugugg ggacggcugu aaugguggcu aucccucugg agcauggagc 480
uucuggacaa aaaaaggccu gguuucaggu ggagucuaca auucucaugu aggcugcuua 540
ccauacacca ucccucccug cgagcaccau gucaauggcu cccguccccc augcacugga 600
gaaggagaua cucccaggug caacaagagc ugugaagcug gcuacucccc auccuacaaa 660
gaggauaagc acuuugggua cacuuccuac agcgugucua acagugugaa ggagaucaug 720
gcagaaaucu acaaaaaugg cccaguggag ggugccuuca cuguguuuuc ugacuucuug 780
acuuacaaau caggaguaua caagcaugaa gccggugaua ugaugggugg ccacgccauc 840
cgcauccugg gcuggggagu agagaaugga guucccuacu ggcuggcagc caacucuugg 900
aaccuugacu ggggugauaa uggcuucuuu aaaauccuca gaggagaaaa ccacuguggc 960
auugaaucag aaauuguggc uggaauccca cgcacugacc aguacugggg aaga 1014

<210> SEQ ID NO 5
<211> LENGTH: 5
<212> TYPE: PRT
<213> ORGANISM: Artificial Sequence
<220> FEATURE:
<223> OTHER INFORMATION: Synthetic Construct

<400> SEQUENCE: 5

Phe Gly Phe Leu Gly
1 5

<210> SEQ ID NO 6
<211> LENGTH: 15
<212> TYPE: RNA
<213> ORGANISM: Artificial Sequence
<220> FEATURE:
<223> OTHER INFORMATION: Synthetic Construct

<400> SEQUENCE: 6
uucggauuuc ugggc 15

<210> SEQ ID NO 7
<211> LENGTH: 358
<212> TYPE: PRT
<213> ORGANISM: Artificial Sequence
<220> FEATURE:
<223> OTHER INFORMATION: Synthetic Construct

<400> SEQUENCE: 7

-continued

Met Trp Trp Ser Leu Ile Leu Leu Ser Cys Leu Leu Ala Leu Thr Ser
1               5                   10                  15

Ala His Asp Lys Pro Ser Phe His Pro Leu Ser Asp Asp Leu Ile Asn
            20                  25                  30

Tyr Ile Asn Lys Gln Asn Thr Thr Trp Gln Ala Gly Arg Asn Phe Tyr
        35                  40                  45

Asn Val Asp Ile Ser Tyr Leu Lys Lys Leu Cys Gly Thr Val Leu Gly
    50                  55                  60

Gly Pro Lys Leu Pro Gly Arg Val Ala Phe Gly Glu Asp Ile Asp Leu
65                  70                  75                  80

Pro Glu Thr Phe Asp Ala Arg Glu Gln Trp Ser Asn Cys Pro Thr Ile
                85                  90                  95

Gly Gln Ile Arg Asp Gln Gly Ser Cys Gly Ser Cys Trp Ala Phe Gly
            100                 105                 110

Ala Val Glu Ala Ile Ser Asp Arg Thr Cys Ile His Thr Asn Gly Arg
        115                 120                 125

Val Asn Val Glu Val Ser Ala Glu Asp Leu Leu Thr Cys Cys Gly Ile
    130                 135                 140

Gln Cys Gly Asp Gly Cys Asn Gly Gly Tyr Pro Ser Gly Ala Trp Ser
145                 150                 155                 160

Phe Trp Thr Lys Lys Gly Leu Val Ser Gly Gly Val Tyr Asn Ser His
                165                 170                 175

Val Gly Cys Leu Pro Tyr Thr Ile Pro Pro Cys Glu His His Val Asn
            180                 185                 190

Gly Ser Arg Pro Pro Cys Thr Gly Glu Gly Asp Thr Pro Arg Cys Asn
        195                 200                 205

Lys Ser Cys Glu Ala Gly Tyr Ser Pro Ser Tyr Lys Glu Asp Lys His
    210                 215                 220

Phe Gly Tyr Thr Ser Tyr Ser Val Ser Asn Ser Val Lys Glu Ile Met
225                 230                 235                 240

Ala Glu Ile Tyr Lys Asn Gly Pro Val Glu Gly Ala Phe Thr Val Phe
                245                 250                 255

Ser Asp Phe Leu Thr Tyr Lys Ser Gly Val Tyr Lys His Glu Ala Gly
            260                 265                 270

Asp Met Met Gly Gly His Ala Ile Arg Ile Leu Gly Trp Gly Val Glu
        275                 280                 285

Asn Gly Val Pro Tyr Trp Leu Ala Ala Asn Ser Trp Asn Leu Asp Trp
    290                 295                 300

Gly Asp Asn Gly Phe Phe Lys Ile Leu Arg Gly Glu Asn His Cys Gly
305                 310                 315                 320

Ile Glu Ser Glu Ile Val Ala Gly Ile Pro Arg Thr Asp Gln Tyr Trp
                325                 330                 335

Gly Arg Phe Gly Phe Leu Gly Arg Gly Gly Leu Cys Tyr Cys Arg Gly
            340                 345                 350

Arg Phe Cys Val Gly Arg
        355

<210> SEQ ID NO 8
<211> LENGTH: 1074
<212> TYPE: RNA
<213> ORGANISM: Artificial Sequence
<220> FEATURE:
<223> OTHER INFORMATION: Synthetic Construct

<400> SEQUENCE: 8

-continued

```
auguggugu ccuugauccu ucuuucuugc cugcuggcac ugaccagugc ccaugacaag      60

ccuuccuucc acccgcuguc ggaugaccug auuaacuaua ucaacaaaca gaauacaaca     120

uggcaggcug gacgcaacuu cuacaauguu gacauaagcu aucugaagaa gcuguguggc     180

acuguccugg guggacccaa acugccagga aggguugcgu ucggugagga cauagaucua     240

ccugaaaccu uugaugcacg ggaacaaugg uccaacugcc cgaccauugg acagauuaga     300

gaccagggcu ccugcggcuc uuguugggca uuuggggcag uggaagccau uucugaccga     360

accugcauuc acaccaaugg ccgagucaac guggaggugu cugcugaaga ccugcuuacu     420

ugcuguggua uccagugugg ggacggcugu aaugguggcu aucccucugg agcauggagc     480

uucuggacaa aaaaaggccu gguuucaggu ggagucuaca auucucaugu aggcugcuua     540

ccauacacca ucccucccug cgagcaccau gucaauggcu cccguccccc augcacugga     600

gaaggagaua cucccaggug caacaagagc ugugaagcug gcuacucccc auccuacaaa     660

gaggauaagc acuuugggua cacuuccuac agcgugucua acagugugaa ggagaucaug     720

gcagaaaucu acaaaaaugg cccaguggag ggugccuuca cuguguuuuc ugacuucuug     780

acuuacaaau caggaguaua caagcaugaa gccggugaua ugaugggugg ccacgccauc     840

cgcauccugg gcuggggagu agagaaugga guucccuacu ggcuggcagc caacucuugg     900

aaccuugacu ggggugauaa uggcuucuuu aaaauccuca gaggagaaaa ccacuguggc     960

auugaaucag aaauuguggc uggaauccca cgcacugacc aguacugggg aagauucgga    1020

uuucugggca ggggcggcuu gugcuacugu cgcggaaggu uuuguguagg caga          1074
```

<210> SEQ ID NO 9
<211> LENGTH: 4
<212> TYPE: PRT
<213> ORGANISM: Artificial Sequence
<220> FEATURE:
<223> OTHER INFORMATION: Synthetic Construct

<400> SEQUENCE: 9

Gly Phe Leu Gly
1

<210> SEQ ID NO 10
<211> LENGTH: 4
<212> TYPE: PRT
<213> ORGANISM: Artificial Sequence
<220> FEATURE:
<223> OTHER INFORMATION: Synthetic Construct

<400> SEQUENCE: 10

Ala Leu Ala Leu
1

<210> SEQ ID NO 11
<211> LENGTH: 4
<212> TYPE: PRT
<213> ORGANISM: Artificial Sequence
<220> FEATURE:
<223> OTHER INFORMATION: Synthetic Construct

<400> SEQUENCE: 11

Ala Gly Val Phe
1

<210> SEQ ID NO 12
<211> LENGTH: 4

-continued

```
<212> TYPE: PRT
<213> ORGANISM: Artificial Sequence
<220> FEATURE:
<223> OTHER INFORMATION: Synthetic Construct

<400> SEQUENCE: 12

Val Lys Lys Arg
1
```